United States Patent
Shah et al.

(10) Patent No.: US 10,744,083 B2
(45) Date of Patent: *Aug. 18, 2020

(54) SELF-REGULATING OSMOTIC GASTRORETENTIVE DRUG DELIVERY SYSTEMS

(71) Applicant: KASHIV BIOSCIENCES, LLC, Bridgewater, NJ (US)

(72) Inventors: Navnit H. Shah, Clifton, NJ (US); Wantanee Phuapradit, Montville, NJ (US); Dipen Desai, Whippany, NJ (US); Jaydeep Vaghashiya, Woodbridge, NJ (US); Kanji Meghpara, Morris Plains, NJ (US)

(73) Assignee: KASHIV BIOSCIENCES, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/634,792

(22) PCT Filed: Jun. 27, 2019

(86) PCT No.: PCT/US2019/039573
§ 371 (c)(1),
(2) Date: Jan. 28, 2020

(87) PCT Pub. No.: WO2020/006278
PCT Pub. Date: Jan. 2, 2020

(65) Prior Publication Data
US 2020/0155446 A1    May 21, 2020

Related U.S. Application Data

(60) Provisional application No. 62/822,572, filed on Mar. 22, 2019, provisional application No. 62/690,568, filed on Jun. 27, 2018.

(51) Int. Cl.
*A61K 9/00* (2006.01)
*A61K 9/20* (2006.01)
(Continued)

(52) U.S. Cl.
CPC .......... *A61K 9/0004* (2013.01); *A61K 9/0065* (2013.01); *A61K 47/02* (2013.01); *A61K 47/12* (2013.01); *A61K 47/32* (2013.01)

(58) Field of Classification Search
None
See application file for complete search history.

(56) References Cited

U.S. PATENT DOCUMENTS 3,732,865 A * 5/1973 Higuchi .................... A61F 6/14
604/892.1
5,681,584 A   10/1997 Savastano et al.
(Continued)

FOREIGN PATENT DOCUMENTS

CN    103 040 785 A    4/2013

OTHER PUBLICATIONS

U.S. Appl. No. 16/778,439, filed Jan. 31, 2020
International Search Report dated Oct. 14, 2019 in International Application No. PCT/US2019/039573.

*Primary Examiner* — Brian Gulledge
(74) *Attorney, Agent, or Firm* — Kashiv BioSciences, LLC; Vandana Awasthi

(57) ABSTRACT

Self-regulating, osmotic, floating gastroretentive compositions that provide extended release, delayed release, and/or delayed extended release of active pharmaceutical agents, as well as, optionally, immediate release of the same or a different active pharmaceutical agent, are provided here. The gastroretentive compositions of the disclosure comprise a swellable, extended release, multilayer core comprising a push layer and a pull layer; a water-insoluble permeable elastic membrane surrounding the multilayer core; and an
(Continued)

Figure 1:
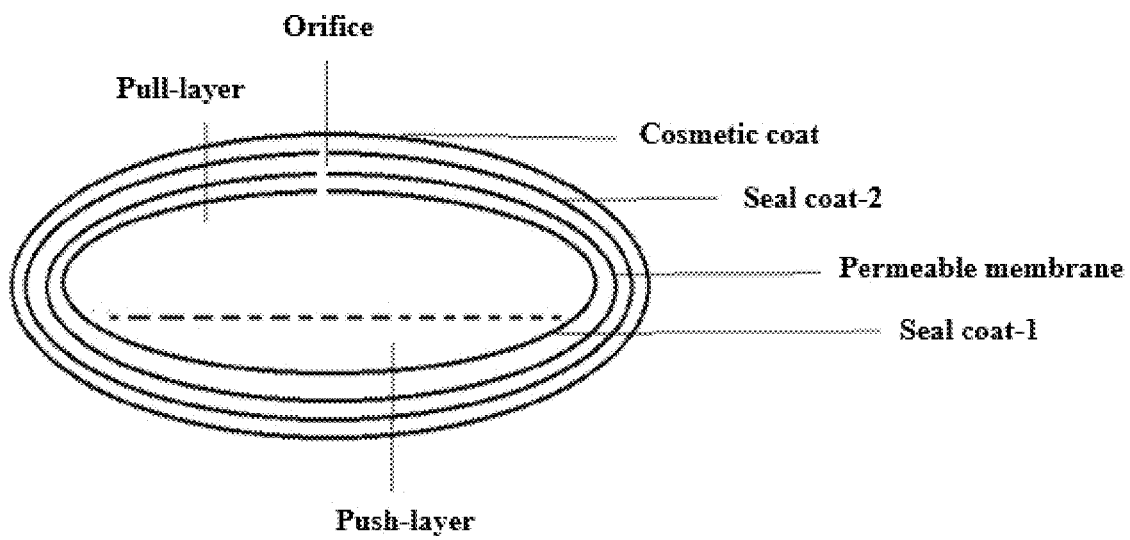

orifice (e.g., a laser-drilled orifice, a manually drilled orifice) on the pull-layer side of the dosage form. The gastric retention of the composition is controlled by rapid floating of the composition and expansion of the membrane. The rapid swelling of the composition to a size greater than the size of the pyloric sphincter is due to the presence of an osmogen. adequate membrane permeability that provides for fast generation of $CO_2$ from a gas-generating agent(s), and adequate membrane elasticity that provides for rapid expansion of the membrane. The hydrated core, especially the polyethylene oxide in the push layer, and the permeable elastic membrane with an orifice (1) provide extended release of the active pharmaceutical agent, and (2) maintain the dosage form at a size suitable for gastric retention. The self-regulating composition collapses, or breaks into pieces, after releasing at least about 80% of the drug from the composition.

13 Claims, 12 Drawing Sheets

(51) Int. Cl.
*A61K 9/28* (2006.01)
*A61K 47/32* (2006.01)
*A61K 47/02* (2006.01)
*A61K 47/12* (2006.01)

(56) References Cited

U.S. PATENT DOCUMENTS

| | | | |
|---|---|---|---|
| 6,881,420 B2 | 4/2005 | Flashner-Barak et al. | |
| 2003/0064101 A1* | 4/2003 | Mehta | A61K 9/0065 424/473 |
| 2008/0299188 A1* | 12/2008 | Appel | A61K 31/496 424/457 |
| 2012/0045485 A1* | 2/2012 | Gan | A61K 31/00 424/400 |
| 2013/0043612 A1 | 2/2013 | Geerke et al. | |
| 2015/0079136 A1 | 3/2015 | Pilgaonkar et al. | |

* cited by examiner

SELF-REGULATING OSMOTIC GASTRORETENTIVE DRUG DELIVERY SYSTEMS

1. RELATED APPLICATIONS

This application is a U.S. National Stage Patent Application under 35 U.S.C. § 371 of International Application No. PCT/US2019/039573, filed on Jun. 27, 2019, which claims priority to U.S. Provisional Patent Application Nos. 62/690,568, filed Jun. 27, 2018, and 62/822,572, filed Mar. 22, 2019, the disclosures of which are hereby incorporated by reference in their entireties.

2. TECHNICAL FIELD

The present disclosure provides compositions comprising a self-regulating, osmotic, floating gastroretentive drug delivery system. The compositions of the disclosure are suitable for providing extended release of drugs that possess a rationale for gastroretentive administration. The compositions extend the release of drug for about 6 hours to about 24 hours, without losing gastroretentive attributes of the system (GRS attributes), and break into fragments, or collapse to allow emptying from the gastrointestinal (GI) tract after complete drug release from the composition. The compositions of the disclosure, when consumed or when in contact with media simulating gastric conditions, float in about 30 minutes or less, expand in about 60 minutes or less to a size that prevents passage through the pyloric sphincter of a human, and remain in an expanded state, while releasing therapeutic concentrations of the drug, for prolonged periods, e.g., about 6-24 hours.

3. BACKGROUND

Despite advances in extended release technology, retention of a drug in an extended release dosage form beyond the duration of a fed mode/gastric emptying can reduce therapeutic efficacy of many drugs. In the absence of food, the dosage form can pass from the stomach into the small intestine, and over a period of two to four hours can pass through the small intestine, reaching the colon with the drug still in the dosage form. This can be problematic for drugs that would normally provide maximum benefit with minimum side effects when absorbed in the upper gastrointestinal (GI) tract and jejunum, rather than, e.g., the colon. For example, most orally administered antibiotics have a potential of altering the normal flora of the GI tract, and particularly the flora of the colon, resulting in release of dangerous toxins causing nausea, diarrhea, and life-threatening or fatal side effects; examples of antibiotics that pose this type of threat are tetracycline, metronidazole, amoxicillin, and clindamycin.

Other challenges exist with certain drugs that are susceptible to degradation by intestinal enzymes. The degradation occurs before the drug can be absorbed through the intestinal wall, leaving only a fraction of the administered dose available for the intended therapeutic action. Examples of such drugs include ranitidine and metformin hydrochloride.

For certain drugs, the pH at a given site within the GI tract is an essential determinant of the bioavailability of the drug, as the solubility of the drug varies with the pH. In certain situations, such drugs are not fully absorbed before reaching the colon because they require an acidic environment for providing effective bioavailability. For example, esters of ampicillin are highly soluble drugs that achieve their highest bioavailability at a low pH. Some drugs that are soluble in an acidic environment, but insoluble in an alkaline environment, lose their efficacy upon reaching the lower portions of the GI tract. For such drugs, the portions of the drug that are undissolved cannot be absorbed, whereas the portions that are dissolved but not yet absorbed can precipitate in the small intestine. Therefore, it is desirable to formulate such active pharmaceutical agents in dosage forms that release and absorb the active agent before reaching the lower GI tract.

Further, retention of a drug within a tablet or other dosage form beyond the duration of a fed mode/gastric emptying can reduce the therapeutic efficacy of drugs with a narrow absorption window (NAW) in the upper GI tract.

Gastroretentive dosage forms are particularly beneficial for active pharmaceutical agents that possess at least one of the following rationales for gastroretentive administration: NAW in the upper GI tract, weakly basic with high pH-dependent solubility, act locally in upper GI tract, and active pharmaceutical agents with any of the above characteristics that degrade in lower GI tract and/or disturb normal colonic microbes.

Various gastroretentive systems known in the art are disclosed in the following documents: U.S. Pat. Nos. 4,101,650; 4,777,033; 4,844,905; PCT Publication Nos. WO 00/015198; WO 01/010419; WO 02/000213; Deshpande et al. (1997) *Pharm. Res.,* 14(6):815-819 ("Deshpande (1997a)"); Deshpande et al. (1997) *Int. J. Pharmaceutics,* 159:255-258 ("Deshpande (1997b)"), the disclosures of which are herein incorporated by reference in their entireties.

Deshpande (1997a) discloses gastroretentive tablets with a swelling core and a coating over the tablet core to provide support needed by the core to remain intact in the face of shear stress and the hydrodynamic environment of the GI tract. The swelling core of the gastroretentive tablets comprises CARBOPOL® (pH-dependent swellable anionic polymer), carbonates/bicarbonates, and a superdisintegrant, e.g., polyvinyl pyrrolidone XL. The tablets were noted to swell due to superdisintegrant-assisted disintegration of the tablet matrix, and gelling/swelling of CARBOPOL® in the presence of carbonates/bicarbonates. Further, the release of $CO_2$ in the acidic pH of GI fluid confers buoyancy to the tablet.

Deshpande (1997b) evaluates membranes with various ratios of EUDRAGIT® RL 30D and EUDRAGIT® NE 30D, used in the development of controlled release systems for gastric retention. The publication teaches that increasing amounts of EUDRAGIT® NE 30D have a normalizing effect on overall permeability of the membrane, while enhancing elasticity and mechanical strength of the membrane. The publication provides an optimum ratio of EUDRAGIT® RL 30D and EUDRAGIT® NE 30D as 70:30 in membranes for coating tablets. At this ratio, the paper reports that the combination provided enough elasticity and strength to withstand pressure of expansion.

The two above-mentioned Deshpande publications fail to describe or suggest any osmotic gastroretentive composition that can provide controlled release of a drug, particularly weakly basic drugs, for extended periods of time, e.g., about 10 hours to about 24 hours. Further, the two publications fail to address the mutual noncompatibility of the two polymers and the effects of polymer noncompatibility on the duration of floating, the floating lag time, and the membrane strength and membrane elasticity to withstand pH and hydrodynamic conditions in the stomach. The publications also fail to discuss the effects of any polymer ratios tested on the extended release profile of active pharmaceutical agents with various solubility levels.

Despite improvements in the gastroretentive technology, there are only a handful of products that can take advantage of the gastroretentive technology due to inherent limitations, either due to solubility of active pharmaceutical agent or suboptimal product design.

Thus, there remains a need in the art for gastroretentive drug delivery systems that extend the gastric residence time and duration of floating for drugs with NAW such that the drug is released in a therapeutic amount, at a controlled rate, into the proximity of its site of absorption (or action) for an extended period or reaches other sites in the GI tract in a uniform manner. There is a need in the art for rapidly expanding gastroretentive drug delivery systems that provide controlled extended release of narrow therapeutic index drugs in a desired therapeutic window. There remains a need to develop rapidly expanding gastroretentive drug delivery systems, suitable for compositions with any drug loading capacity, to provide extended release, or combined immediate and extended release, of drugs that possess at least one of the above mentioned rationales for gastric retention. In particular, there is a need in the art for a gastroretentive drug delivery system that provides compositions, that float, e.g., in about 15-30 minutes or less, and expand, e.g., in about one hour or less (e.g., about 30 minutes), to a size that prevents its passage through the pyloric sphincter of a human when in contact with gastric fluids, remain in an expanded state while providing extended release of the drug for prolonged periods, e.g., about 6 to about 24 hours, and then either break into fragments, or collapse into a state suitable for emptying of the composition from the GI tract. The present disclosure provides self-regulating, osmotic, floating gastroretentive compositions that address the issues of providing uniform drug release with minimal pharmacokinetic variability, improving drug bioavailability, reducing floating lag time, and providing rapid expansion, that is independent of pH and food, to avoid premature transit of the composition through the GI tract.

4. SUMMARY

In certain embodiments, the present disclosure provides for an osmotic, floating gastroretentive dosage form comprising a multilayer core comprising a pull layer containing an active pharmaceutical agent, an acid, and a gas-generating agent; and a push layer, and a permeable elastic membrane surrounding the multilayer core, wherein the permeable elastic membrane contains at least one orifice and comprises at least one ammonium polymethacrylate copolymer.

In certain embodiments, the dosage form of the present disclosure, when in contact with media simulating gastric conditions, can float in about 30 minutes or less, and can swell in about one hour or less to a size that prevents its passage through a pyloric sphincter of a human and avoids premature transit to lower portions of gastrointestinal tract.

In certain embodiments, the dosage form of the present disclosure can provide an extended release of the active pharmaceutical agent, in the stomach of a patient consuming the dosage form, for a period of at least about 10 hours.

In certain embodiments, the dosage form of the present disclosure can remain in the swollen state for at least about 10 hours.

In certain embodiments, the dosage form of the present disclosure can be self-regulating dosage form that, when in contact with media simulating gastric conditions, floats in about 30 minutes or less, and swells in about one hour or less to a size that prevents its passage through a pyloric sphincter of a human, and collapses or breaks apart when at least about 80% of the active pharmaceutical agent is released.

In certain embodiments, the dosage form of the present disclosure can exhibit a volume gain of about 100% in less than about 1 hour in 200 ml of pH 4.5 acetate buffer at 37° C.

In certain embodiments, the dosage form of the present disclosure can exhibit a volume gain of about 100% in about 3 hours in about 200 ml of light meal media at about 37° C. In certain embodiments, the light meal media comprises sodium chloride, potassium chloride, calcium chloride, phosphate salts, citric acid, and sugar.

In certain embodiments, the dosage form of the present disclosure can, upon dissolution in about 900 ml of a dissolution medium comprising about 0.001 N HCl with 10 mM NaCl, exhibit about 40% dissolution of the active pharmaceutical agent in about 120 minutes.

In certain embodiments, the orifice in the permeable elastic membrane of the dosage form of the present disclosure is in fluid communication with the pull layer.

In certain embodiments, both the pull layer and the push layer of the dosage form of the present disclosure can comprise swellable water-soluble hydrophilic polymers. In certain embodiments, the swellable water-soluble hydrophilic polymer in the push layer is a polyethylene oxide having an average molecular weight of greater than or equal to 600,000. In certain embodiments, the swellable water-soluble hydrophilic polymer in the pull layer is a polyethylene oxide having an average molecular weight of less than or equal to 1,000,000. In certain embodiments, the swellable water-soluble hydrophilic polymers are polyethylene oxides. In certain embodiments, the average molecular weights of the polyethylene oxides in the pull layer and the push layer are different to provide a decreasing viscosity gradient from the push layer to the pull layer. In certain embodiments, the viscosity gradient from push layer to pull layer can be sufficient to prevent mixing of the two layers.

In certain embodiments the permeable elastic membrane layer of the dosage form of the present disclosure can further comprises a plasticizer. In certain embodiments, the plasticizer can be present in amount of between about 10 wt % and about 20 wt % of ammonium polymethacrylate copolymer.

In certain embodiments, the gas-generating agent of the dosage form of the present disclosure can be present in an amount of between about 10 wt % and about 50 wt % of the pull layer.

In certain embodiments, the dosage form of the present disclosure can be a horizontally compressed bilayer tablet comprising a long axis and a short axis.

In certain embodiments, the dosage form of the present disclosure can be a horizontally compressed oval, modified oval, or capsule shaped bilayer tablet. In certain embodiments, the long axis can be between about 12 mm and about 22 mm long and the short axis can be between about 8 mm and about 11 mm long.

In certain embodiments, the active pharmaceutical agent of the dosage form of the present disclosure can be a weakly basic drug.

In certain embodiments, the polyethylene oxide of the dosage form of the present disclosure can have an average molecular weight of about 200,000, about 300,000, about 400,000, about 500,000, about 600,000, about 700,000, about 800,000, about 900,000, or intermediate values therein.

In certain embodiments, the polyethylene oxide of the dosage form of the present disclosure can have an average molecular weight of about 700,000, about 800,000, about 900,000, about 1,000,000, about 2,000,000, about 3,000,000, about 4,000,000, about 5,000,000, about 6,000,000, about 7,000,000, or intermediate values therein.

In certain embodiments, the swellable water-soluble hydrophilic polymer in the pull layer of the dosage form of the present disclosure can be a mixture of two polyethylene oxides having average molecular weights of about 7,000,000 and about 200,000 that are present in a ratio of between about 1:99 and about 10:90 respectively.

In certain embodiments, the gas-generating agent of the dosage form of the present disclosure can be a carbonate salt selected from the group consisting of $NaHCO_3$, $CaCO_3$, and a mixture thereof. In certain embodiments, the gas-generating agent can be a mixture of $NaHCO_3$ and $CaCO_3$.

In certain embodiments, the acid of the dosage form of the present disclosure can be selected from the group consisting of succinic acid, citric acid, acetic acid, malic acid, fumaric acid, stearic acid, tartaric acid, boric acid, benzoic acid, and combinations thereof. In certain embodiments, the acid can be succinic acid.

In certain embodiments, the plasticizer of the dosage form of the present disclosure can be selected from the group consisting of triethyl citrate, triacetin, polyethylene glycol, propylene glycol, and dibutyl sebacate. In certain embodiments, the plasticizer can be triethyl citrate.

In certain embodiments, the ammonium polymethacrylate copolymer of the dosage form of the present disclosure can be a copolymer of ethyl acrylate, methyl methacrylate, and trimethylammonioethyl methacrylate chloride in powder form (EUDRAGIT® RL PO).

In certain embodiments, the dosage form of the present disclosure can further comprise a cosmetic coat over the permeable elastic membrane.

In certain embodiments, the dosage form of the present disclosure can further comprise a seal coat between the core and the permeable elastic membrane. In certain embodiments, the seal coat of the dosage form of the present disclosure can comprise a pH-independent water-soluble polymer containing a hypromellose-based polymer or a polyvinyl acetate-based polymer.

In certain embodiments, the gas-generating agent of the dosage form of the present disclosure can generate $CO_2$ independent of a fed or fasted state of an individual.

In certain embodiments, the dosage form of the present disclosure can exhibit a floating lag time of about 15 minutes or less in about 250 ml of pH 4.5 acetate buffer.

In certain embodiments, the push layer of the dosage form of the present disclosure can further comprise an osmogen selected from the group comprising sodium chloride, potassium chloride, potassium sulfate, lithium sulfate, sodium sulfate, lactose and sucrose combination, lactose and dextrose combination, sucrose, dextrose, mannitol, dibasic sodium phosphate, and combinations thereof. In certain embodiments, the osmogen can be sodium chloride.

In certain embodiments, the dosage form of the present disclosure can expand in about 30 minutes or less to a size that prevents its passage through pyloric sphincter.

In certain embodiments, the present disclosure provides for an osmotic, floating gastroretentive dosage form comprising a multilayer core comprising a pull layer containing an active pharmaceutical agent, an acid, and a gas-generating agent; and a push layer, and a permeable elastic membrane containing an orifice and surrounding the multilayer core, wherein the membrane comprises a plasticizer and an ammonium polymethacrylate copolymer, wherein the plasticizer is present in an amount of between about 10 wt % and about 20 wt % of the quaternary ammonium polymethacrylate copolymer, wherein the dosage form, when in contact with media simulating gastric conditions, floats in about 30 minutes or less, and expands in about one hour or less to a size that prevents its passage through a pyloric sphincter of a human, and wherein the membrane maintains the integrity of the dosage form in the expanded state to provide an extended release of the active pharmaceutical agent for a period of at least about 12 hours.

In certain embodiments, the dosage form of the present disclosure can expand in about 30 minutes or less to a size that prevents its passage through pyloric sphincter. In certain embodiments, the dosage form of the present disclosure can exhibit at least about 100% volume gain in about 3 hours in about 200 ml of an aqueous medium comprising sodium chloride, potassium chloride, calcium chloride, citric acid, phosphate salts, and sugar.

In certain embodiments, the medium simulating gastric conditions can be pH 4.5 acetate buffer.

In certain embodiments, the dosage form of the present disclosure can, upon dissolution in about 900 ml of a dissolution medium comprising about 10 mM NaCl in about 0.001 N HCl, exhibit at least about 40% dissolution of the active pharmaceutical agent in about 120 minutes.

In certain embodiments, both, the pull layer and the push layer of the dosage form of the present disclosure can comprise swellable water-soluble hydrophilic polymers.

In certain embodiments the orifice in the permeable elastic membrane of the present disclosure can be in fluid communication with the pull layer.

In certain embodiments, the push layer of the dosage form of the present disclosure can comprise an osmogen, and a swellable water-soluble hydrophilic polymer. In certain embodiments, the swellable water soluble hydrophilic polymer can be a polyethylene oxide having an average molecular weight of greater than or equal to about 600,000.

In certain embodiments, the pull layer of the dosage form of the present disclosure can further comprise a swellable water-soluble hydrophilic polymer.

In certain embodiments, the swellable water soluble hydrophilic polymer of the dosage form of the present disclosure can be a polyethylene oxide having an average molecular weight of less than or equal to about 1,000,000.

In certain embodiments, the swellable water-soluble hydrophilic polymer of the dosage form of the present disclosure can be a polyethylene oxide.

In certain embodiments, the average molecular weights of the polyethylene oxides in the pull layer and the push layer of the dosage forms of the present disclosure can be different to provide a decreasing viscosity gradient from the push layer to the pull layer. In certain embodiments, the viscosity gradient from push layer to pull layer can be sufficient to prevent mixing of the two layers.

In certain embodiments, the gas-generating agent of the dosage form of the present disclosure can comprise a mixture of sodium bicarbonate and calcium carbonate that is present in an amount of about 10 wt % to about 20 wt % of the pull layer.

In certain embodiments, the plasticizer of the dosage form of the present disclosure can be present in an amount of between about 10 wt % and about 15 wt % of quaternary ammonium polymethacrylate copolymer.

In certain embodiments, the dosage form of the present disclosure can be a horizontally compressed oval, modified oval, or capsule shaped bilayer tablet comprising a long axis and a short axis. In certain embodiments, the present disclosure provides for a bilayer tablet wherein the long axis is between about 12 mm to about 22 mm long and the short axis is between about 8 mm to about 11 mm long.

In certain embodiments, the active pharmaceutical agent of the dosage form of the present disclosure can be a weakly basic drug.

In certain embodiments, the dosage form of the present disclosure can exhibit a volume gain of at least about 100% in about 45 minutes in about 200 ml of about 0.01 N HCl.

In certain embodiments, the dosage form of the present disclosure can exhibit a volume gain of at least about 150% in about 120 minutes in about 200 ml of about 0.01 N HCl.

In certain embodiments, the swellable water-soluble hydrophilic polymer in the pull layer of the dosage form of the present disclosure can comprise one or more polyethylene oxides having an average molecular weight of about 200,000, about 300,000, about 400,000, about 500,000, about 600,000, about 700,000, about 800,000, about 900,000, or intermediate values therein.

In certain embodiments, the swellable water-soluble hydrophilic polymer in the push layer of the dosage form of the present disclosure can comprise one or more polyethylene oxides having an average molecular weight of about 700,000, about 800,000, about 900,000, about 1,000,000, about 2,000,000, about 3,000,000, about 4,000,000, about 5,000,000, about 6,000,000, about 7,000,000, or intermediate values therein.

In certain embodiments, the swellable water-soluble hydrophilic polymer in the pull layer of the dosage form of the present disclosure can be a mixture of two polyethylene oxides having average molecular weights of about 7,000,000 and about 200,000, present in a ratio of between about 1:99 and about 10:90 respectively.

In certain embodiments, the acid of the dosage form of the present disclosure can be selected from the group consisting of succinic acid, citric acid, acetic acid, malic acid, fumaric acid, stearic acid, tartaric acid, boric acid, benzoic acid, and combinations thereof. In certain embodiments, the acid can be succinic acid.

In certain embodiments, the plasticizer of the dosage form of the present disclosure can be selected from the group consisting of triethyl citrate, triacetin, polyethylene glycol, propylene glycol, and dibutyl sebacate.

In certain embodiments, the plasticizer of the dosage form of the present disclosure can be triethyl citrate.

In certain embodiments, the ammonium polymethacrylate copolymer of the dosage form of the present disclosure can be a powder copolymer of ethyl acrylate, methyl methacrylate, and trimethylammonioethyl methacrylate chloride (EUDRAGIT® RL PO).

In certain embodiments, the dosage form of the present disclosure can further comprise a cosmetic coat over the permeable elastic membrane.

In certain embodiments, the dosage form of the present disclosure can further comprise a seal coat between the core and the permeable elastic membrane.

In certain embodiments, the seal coat of the present disclosure can comprise a pH-independent water-soluble polymer containing a hypromellose-based polymer or a polyvinyl acetate-based polymer.

In certain embodiments, the present disclosure provides for a horizontally compressed oval-shaped bilayer gastroretentive tablet dosage form containing a long axis and a short axis, wherein the long axis is between about 12 mm and about 22 mm long, the short axis is between about 8 mm and about 11 mm wide, wherein the bilayer tablet, when in contact with media simulating gastric conditions, floats in about 30 minutes or less, and expands in about one hour or less to a size that prevents its passage through a pyloric sphincter of a human.

In certain embodiments, the bilayer gastroretentive dosage form of the present disclosure can further comprise a bilayer core comprising a pull layer containing an active pharmaceutical agent, an acid, and a gas-generating agent; and a push layer, and a permeable elastic membrane containing an orifice and surrounding the multilayer core.

In certain embodiments, the membrane of the bilayer gastroretentive dosage form of the present disclosure can comprise a plasticizer and an ammonium polymethacrylate copolymer.

In certain embodiments, the present disclosure provides for a self-regulating, osmotic, floating gastroretentive dosage form comprising a multilayer core comprising a pull layer containing an active pharmaceutical agent, an acid, and a gas-generating agent; and a push layer, and a permeable elastic membrane containing at least one orifice and surrounding the multilayer core, wherein the permeable elastic membrane comprises at least one ammonium polymethacrylate copolymer; wherein the dosage form, when in contact with media simulating gastric conditions, floats in about 30 minutes or less, and swells in about one hour or less to a size that prevents its passage through a pyloric sphincter of a human, and collapses or breaks apart when at least about 80% of the active pharmaceutical agent is released.

In certain embodiments, the present disclosure provides for a method for improving bioavailability of a weakly basic drug with a narrow absorption window in the upper gastrointestinal tract, the method comprising administering to a subject a self-regulating, osmotic, floating gastroretentive dosage form comprising a multilayer core comprising (1) a pull layer containing the weakly basic drug, an acid, and a gas-generating agent; and a push layer, and (2) a permeable elastic membrane surrounding the multilayer core, wherein the permeable membrane contains at least one orifice and at least one ammonium polymethacrylate copolymer, and wherein the dosage form provides a stable concentration of the weakly basic drug for an extended period of time.

In certain embodiments, the present disclosure provides for a method for treating a condition that requires extended release of an active pharmaceutical agent that is absorbed in the upper gastrointestinal tract, the method comprising administering to a subject a self-regulating, osmotic, floating gastroretentive dosage form comprising (1) a multilayer core comprising a pull layer containing the active pharmaceutical agent, an acid, and a gas-generating agent; and a push layer, and (2) a permeable elastic membrane surrounding the multilayer core, wherein the permeable elastic membrane contains at least one orifice and at least one ammonium polymethacrylate copolymer.

In certain embodiments, the present disclosure provides for a method for treating Parkinson's disease, the method comprising administering to a Parkinson's disease patient a self-regulating, osmotic, floating gastroretentive dosage form comprising (1) a multilayer core comprising a pull layer containing an active pharmaceutical agent(s) suitable for treating Parkinson's disease, an acid, and a gas-generating agent; and a push layer, and (2) a permeable elastic membrane surrounding the multilayer core, wherein the permeable elastic membrane contains at least one orifice and at least one ammonium polymethacrylate copolymer.

In certain embodiments, the present disclosure provides for a method for making a self-regulating, osmotic, floating gastroretentive dosage form, wherein the method comprises making a pull layer blend containing a drug, and a push layer blend; horizontally compressing the pull layer blend and the push layer blend into a bilayered tablet core; coating the bilayered tablet core with a permeable elastic membrane; and drilling an orifice into the permeable elastic membrane to provide fluid communication with the pull layer, wherein making the pull layer blend comprises making intermediate drug granules containing the drug, and mixing the drug granules with extragranular excipients into a pull layer blend; wherein the intermediate drug granules comprise the drug, polyethylene oxide, and an acid, and the extragranular excipients comprise a filler, a glidant, and a lubricant; wherein making the push layer blend comprises mixing an osmogen, polyethylene oxide, a color pigment, and a lubricant into a push layer blend; and wherein the permeable elastic membrane contains at least one ammonium polymethacrylate copolymer and at least one plasticizer.

5. BRIEF DESCRIPTION OF THE DRAWINGS

FIG. 1 depicts a schematic representation of the osmotic gastroretentive dosage form according to certain embodiments. FIG. 1 provides a schematic representation of the gastroretentive dosage form, according to certain embodiments, illustrating a bilayer tablet core, comprising a Push layer and a Pull layer, Seal coat-1 surrounding the tablet core, a Permeable elastic membrane surrounding Seal coat-1, Seal coat-2 surrounding the permeable elastic membrane, a cosmetic coat surrounding Seal coat-2, and an Orifice passing through Seal coat-1, the Permeable membrane, and Seal coat-2, wherein the Orifice is in fluid communication with the Pull layer.

Figure 2:
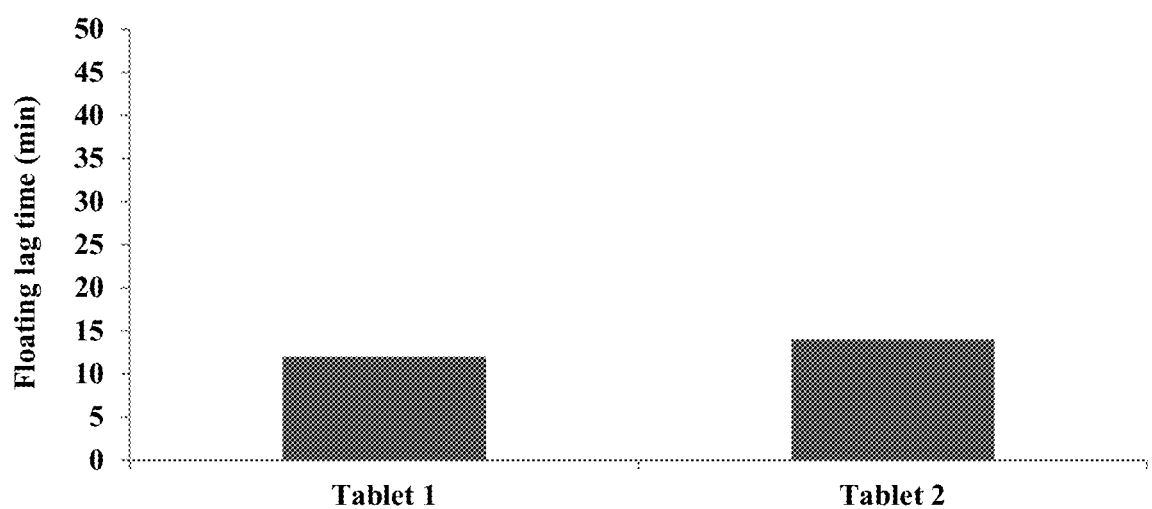

FIG. 2 compares floating lag times of Tablet 1 and Tablet 2 in about 250 ml of pH 4.5 acetate buffer, using USP dissolution apparatus III—Biodis reciprocating cylinder, at about 25 dpm and about 37° C. Tablet 2 contained a higher coating weight gain in its functional coat than Tablet 1. FIG. 2 demonstrates that Tablets 1 and 2 exhibit a floating lag time of about 15 minutes or less.

Figure 3:
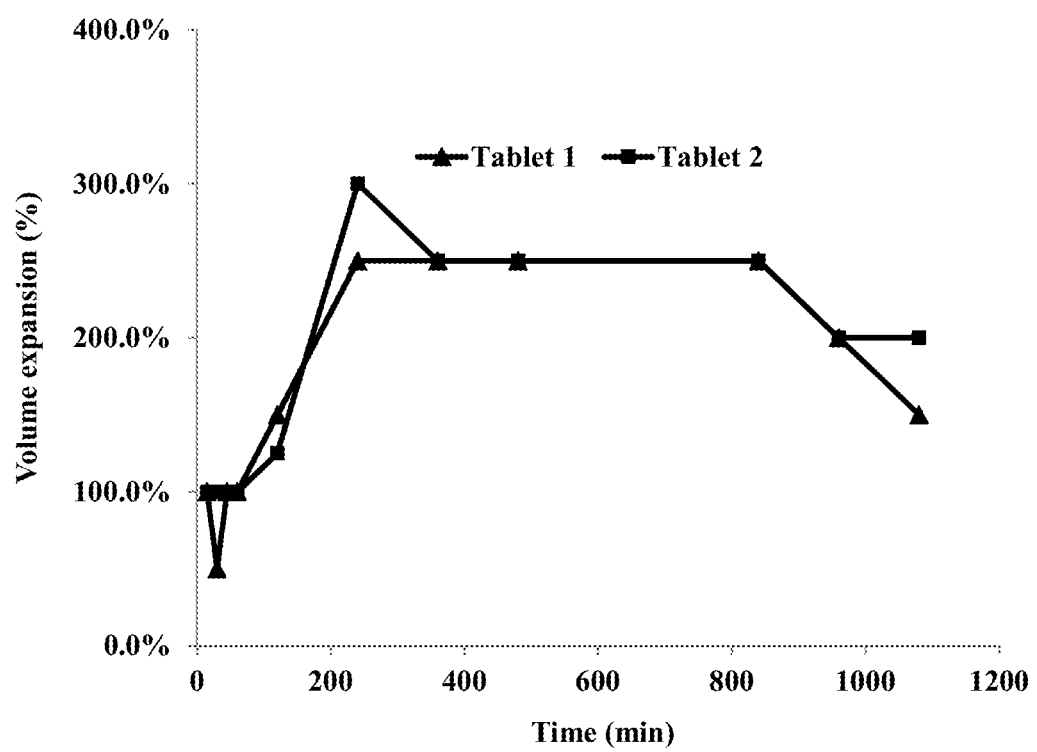

FIG. 3 compares volumetric swelling of Tablets 1 and 2 in about 200 ml of pH 4.5 acetate buffer, using a rotating bottle method, at about 15 rpm and about 37° C. Tablet 2 contained a higher coating weight gain in its functional coat than Tablet 1. FIG. 3 shows volume gains of Tablets 1 and 2 over an 18-hour period. FIG. 3 demonstrates that Tablets 1 and 2 exhibit a volume gain of about 100% in less than 1 hour, e.g., about 45 minutes.

Figure 4:
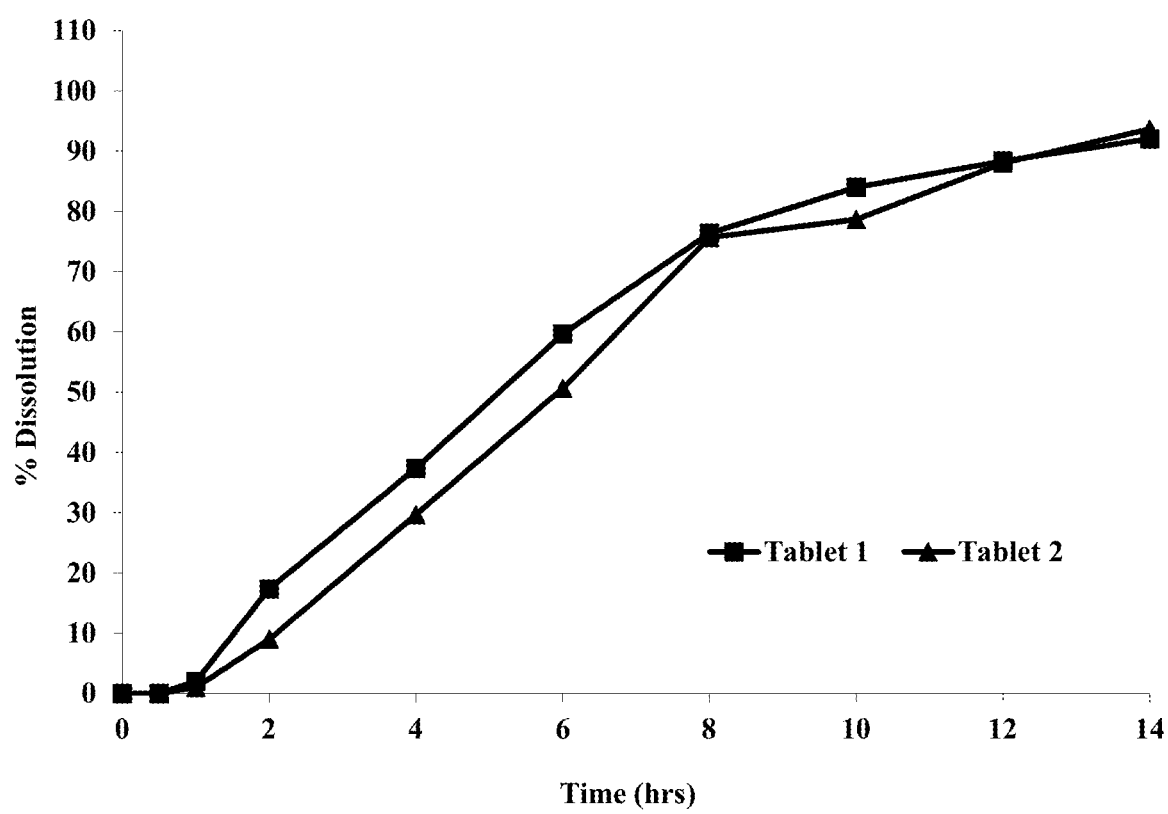

FIG. 4 compares dissolution profiles of levodopa from Tablets 1 and 2, in about 900 ml of pH 4.5 acetate buffer, using USP dissolution apparatus I—Custom Basket, at about 100 rpm and about 37° C. Tablet 2 contained a higher coating weight gain in its functional coat than Tablet 1. FIG. 4 demonstrates that Tablets 1 and 2 exhibit less than about 20% dissolution of levodopa in about 2 hours.

Figure 5:
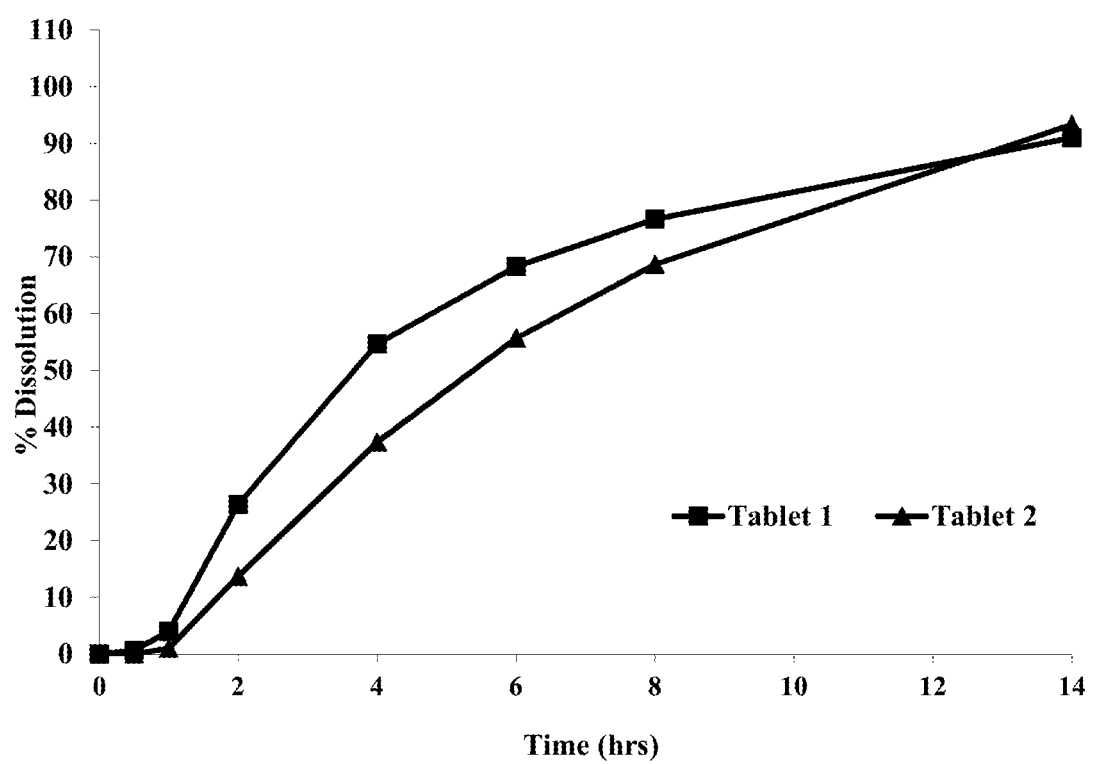

FIG. 5 compares dissolution profiles of levodopa from Tablets 1 and 2, in about 200 ml of pH 4.5 acetate buffer, using a rotating bottle method, at about 15 rpm and about 37° C. Tablet 2 contained a higher coating weight gain in its functional coat than Tablet 1. FIG. 5 demonstrates that Tablets 1 and 2 exhibit less than about 30% dissolution of levodopa in about 2 hours.

Figure 6:
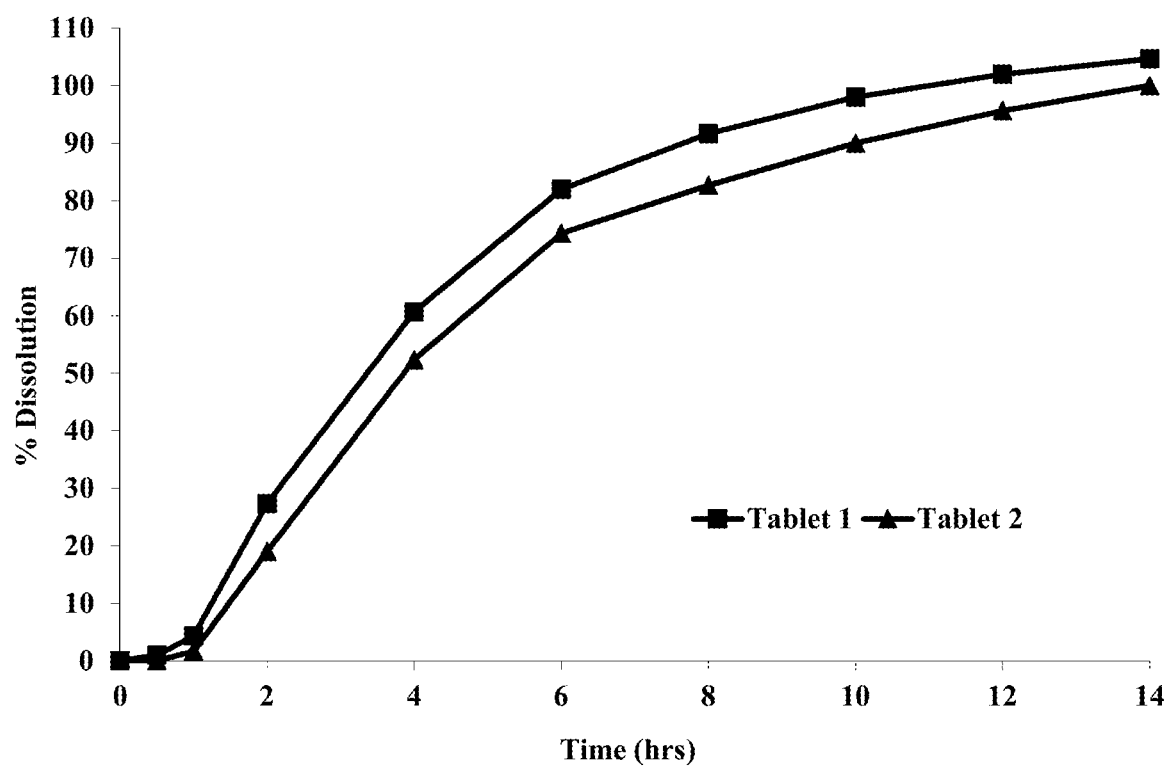

FIG. 6 compares dissolution profiles of levodopa from Tablets 1 and 2, in about in 250 ml of pH 4.5 acetate buffer, using USP III—Biodis reciprocating cylinder, at about 25 dpm and about 37° C. Tablet 2 contained a higher coating weight gain in its functional coat than Tablet 1. FIG. 6 demonstrates that Tablets 1 and 2 exhibit less than about 30% dissolution of levodopa in about 2 hours.

Figure 7:
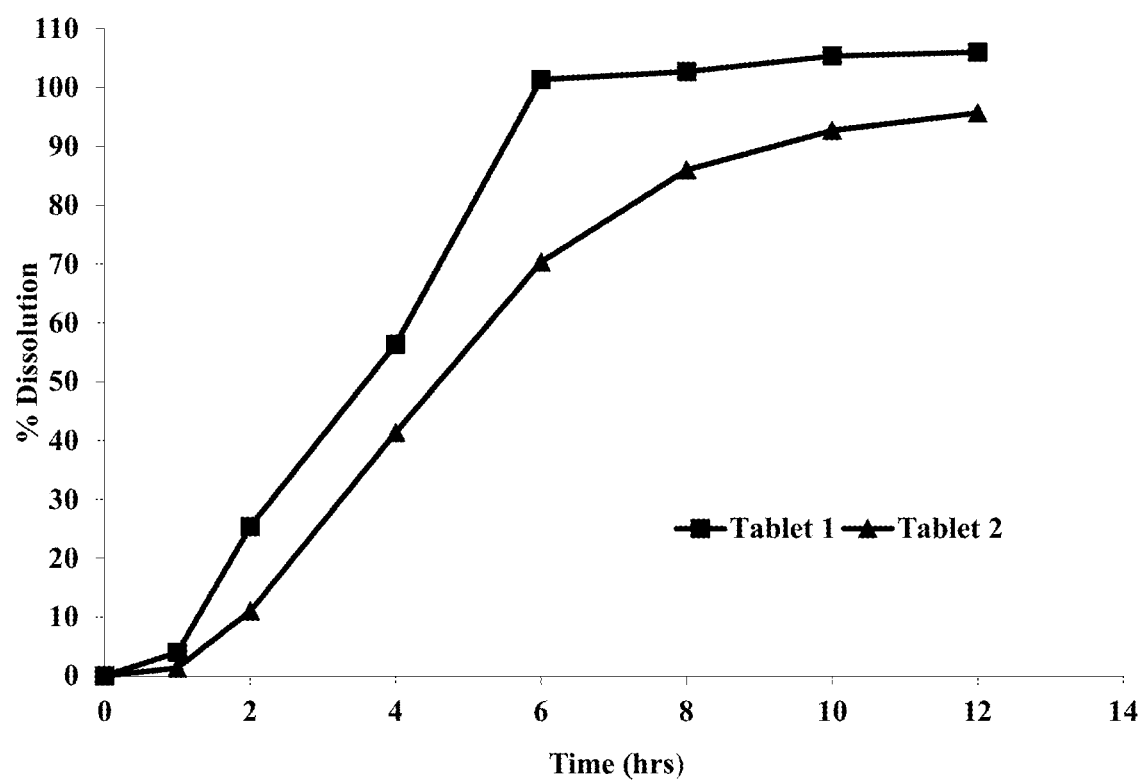

FIG. 7 shows cyclic dissolution profile of levodopa from Tablet 1 and Tablet 2, using USP III—Biodis reciprocating cylinder, at about 25 dpm and about 37° C., with an initial dissolution in about 250 ml pH 4.5 acetate buffer, followed by dissolution in about 250 ml 0.01 N HCl, and final dissolution in about 250 ml pH 4.5 acetate buffer. Tablet 2 contained a higher coating weight gain in its functional coat than Tablet 1. FIG. 7 demonstrates that Tablets 1 and 2 exhibit less than about 30% dissolution of levodopa in about 2 hours.

Figure 8:
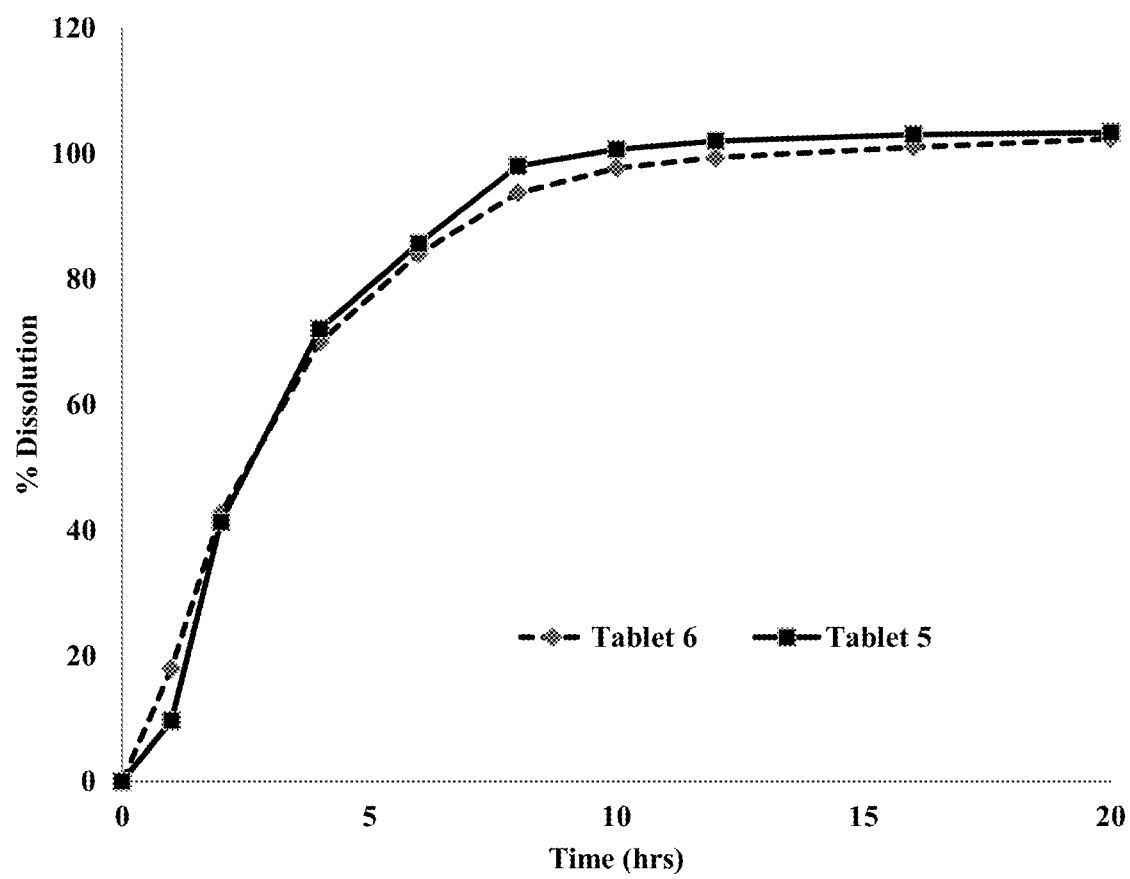

FIG. 8 compares dissolution profiles of levodopa from Tablet 5 (240 mg levodopa) and Tablet 6 (320 mg levodopa), in 900 ml of a dissolution medium comprising about 10 mM NaCl in about 0.001 N HCl, using USP I—Custom Basket, at about 100 rpm and about 37° C. FIG. 8 demonstrates about 40% dissolution of levodopa in about 2 hours.

Figure 9:
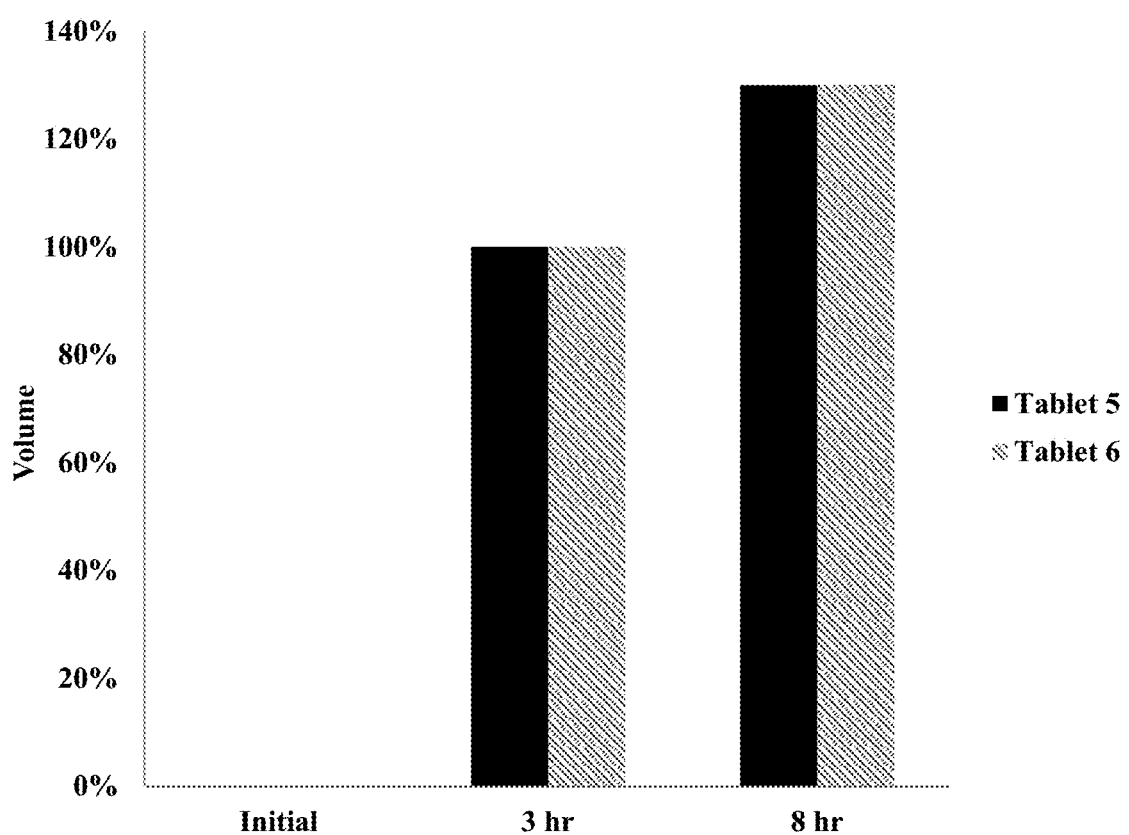

FIG. 9 compares volumetric swelling of Tablet 5 (240 mg levodopa) and Tablet 6 (320 mg levodopa) in about 200 ml of an aqueous medium comprising sodium chloride, potassium chloride, calcium chloride, phosphate salts, citric acid, and sugar (light meal media), using a rotating bottle method, at about 15 rpm and about 37° C. FIG. 9 shows volume gain of Tablet 5 and Tablet 6 over an 8-hour period. The figure demonstrates that Tablets 5 and 6 exhibit a volume gain of about 100% in about 3 hours.

Figure 10:
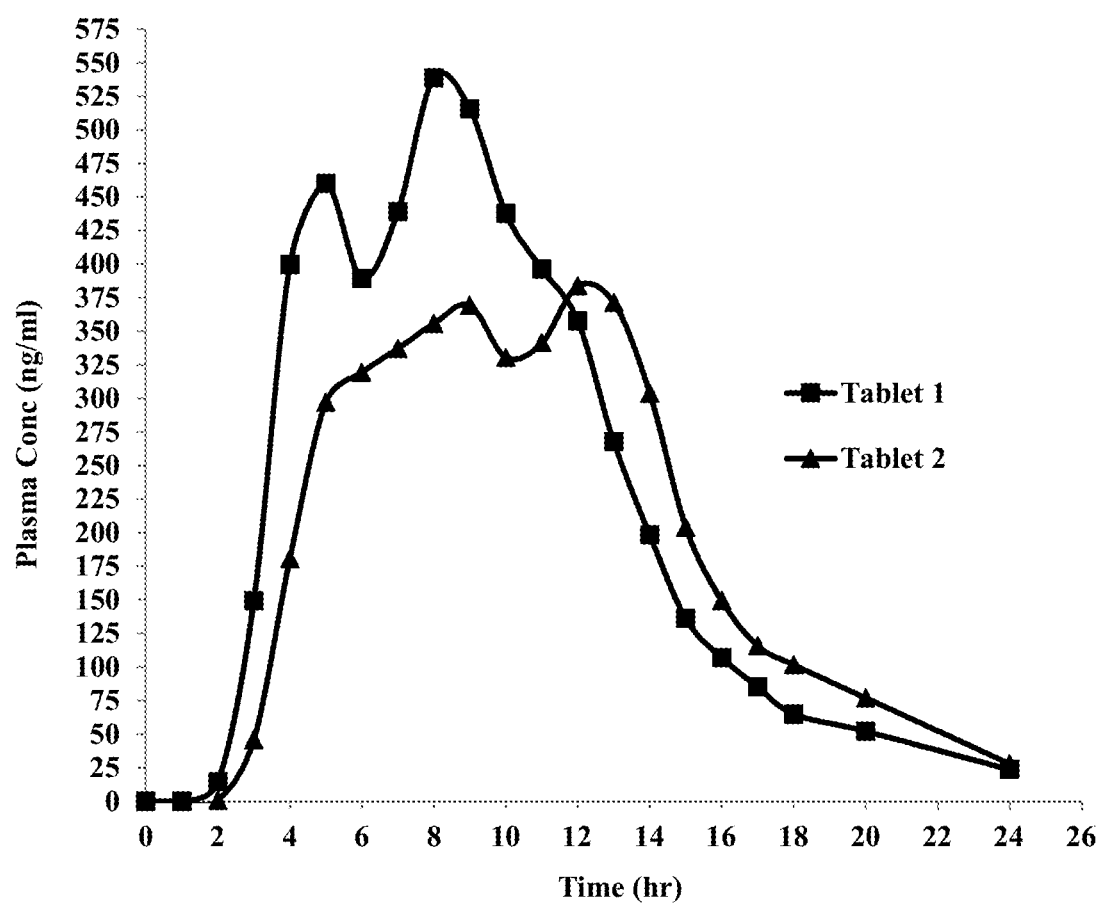

FIG. 10 shows pharmacokinetic profile for levodopa using Tablet 1 and Tablet 2. Tablet 2 contained a higher coating weight gain in its functional coat than Tablet 1. FIG. 10 demonstrates that Tablet 1 and Tablet 2 provide extended release of levodopa for a period of about 12 hours and are suitable for once or twice daily administration.

Figure 11:
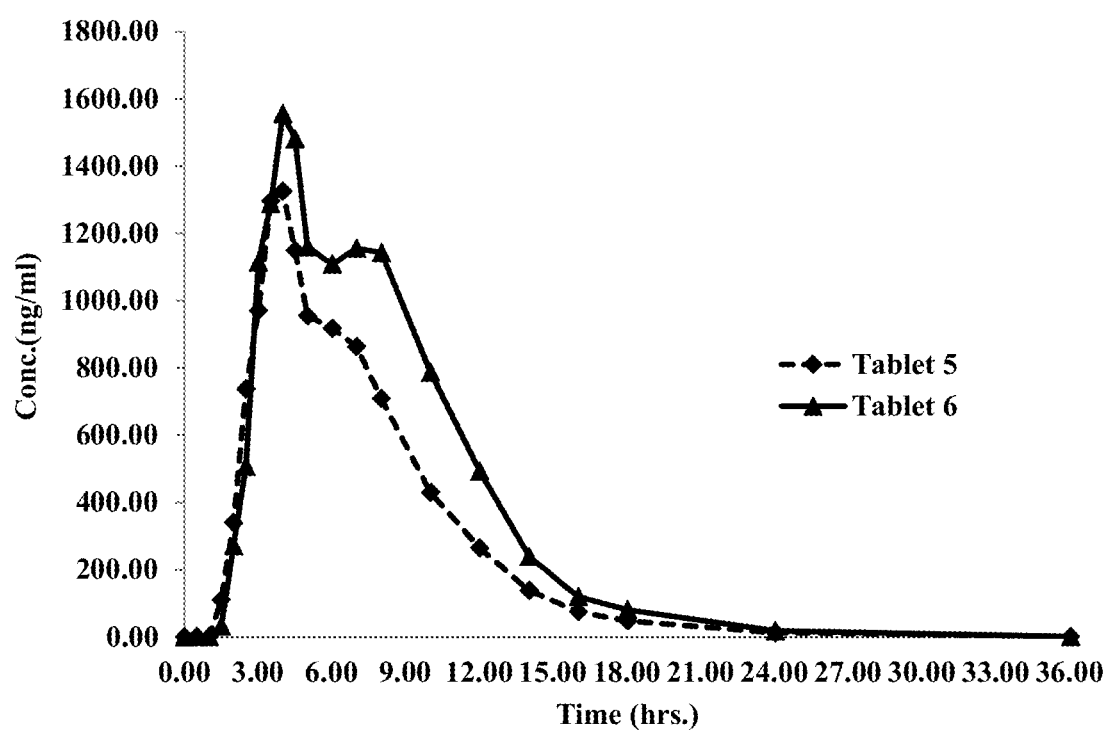

FIG. 11 shows pharmacokinetic profiles for levodopa using Tablet 5 and Tablet 6. Tablet 5 contained 240 mg of levodopa ("LD"), 64.80 mg of carbidopa ("CD"), and 51.50 mg of PARTECK® M200. Tablet 6 contained 320 mg of LD, 86.40 mg of CD, and no PARTECK® M200. FIG. 11 demonstrates that Tablet 5 and Tablet 6 provide about 30% increase in bioavailability compared to Tablet 1 and Tablet 2 (see, e.g., Tablets 1 and 2 in FIG. 10). FIG. 11 further demonstrates dose proportionality between the 240 mg and 320 mg tablet strengths.

Figure 12:
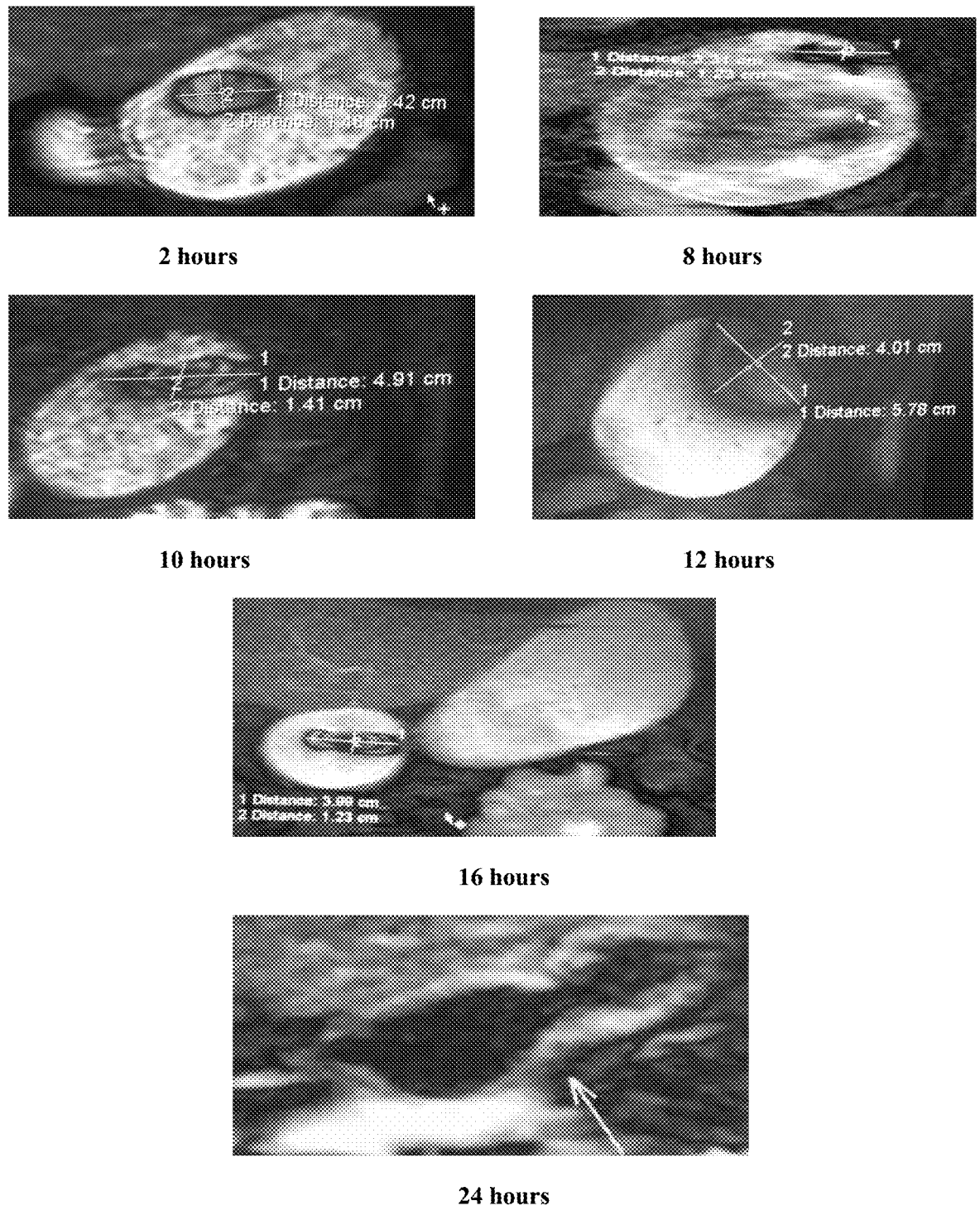

FIG. 12 shows MRI scans in an open label, single-treatment, single period MRI study of Tablet 5 (CD/LD-60/240 mg tablet containing black iron oxide as contrast agent) in a healthy subject under fed conditions. The study was designed to determine the fate of the tablet at 8, 10, 12, 16, and 24 hours (±30 minutes) post dose. FIG. 12 demonstrates that the push layer containing polyethylene oxide with dispersed contrast agent is being released from the tablet between 16 hours and 24 hours post dose.

6. DETAILED DESCRIPTION

The present disclosure provides self-regulating, osmotic gastroretentive compositions that, when in contact with gastric fluids, float in 30 minutes or less, expand rapidly in about one hour or less to a size that prevents their passage through pyloric sphincter, and remain in expanded state for prolonged periods, e.g., about 6-24 hours. The compositions of the disclosure maximize bioavailability of drugs that possess rationales for gastroretentive administration. In particular, the compositions of the disclosure provide for gastroretentive administration of drugs that have variable transit times through various regions of the GI tract, have NAW in the upper GI tract, are susceptible to degradation in alkaline environment, require an acidic environment for maximum solubility, provide maximum benefits with minimum side effects when absorbed in the stomach, duodenum, and proximal small intestine rather than, e.g., the colon, and/or are precipitated in alkaline environment. The compositions of the disclosure improve drug bioavailability by (1) retaining the dosage form in the stomach for a prolonged period, (2) extending the release of the drug in the stomach or upper GI tract, (3) providing uniform release profile for extended periods and (4) minimizing pharmacokinetic variability of the drug. Improved drug bioavailability provided by the gastroretentive compositions of the disclosure reduces side effects, and improves patient compliance.

For clarity and not by way of limitation, this detailed description is divided into the following subportions:

6.1. Definitions;
6.2. Self-regulating, Osmotic, Floating Gastroretentive Dosage Forms;
6.3. Active Agents;
6.4. Methods of Treating;
6.5. Methods of Making; and
6.6. Features of the Dosage Forms.

6.1. Definitions

The terms used in this specification generally have their ordinary meanings in the art, within the context of the disclosed subject matter and in the specific context where each term is used. Certain terms are discussed below, or elsewhere in the specification, to provide additional guidance to the practitioner in describing the compositions and methods of the disclosed subject matter and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

As used herein, "and/or" refers to and encompasses any and all possible combinations of one or more of the associated listed items. The term "about" or "approximately" as used herein means within an acceptable error range for the particular value as determined by one of ordinary skill in the art, which will depend in part on how the value is measured or determined, i.e., the limitations of the measurement system. The term "about" can mean a range of up to 20%, or up to 10%, or up to 5%, or up to 1% of a given value. Alternatively, the term "about," particularly when used with respect to biological systems or processes, can mean within an order of magnitude, or within 5-fold, or within 2-fold, of a value.

The terms "osmotic gastroretentive dosage form," "self-regulating, osmotic, floating gastroretentive dosage form/," or the like, refer to a self-regulating, push-pull osmotic, floating dosage form providing delayed gastric emptying as compared to food (e.g., retention in the stomach beyond the retention of food).

The term "self-regulating" as used herein refers to a gastroretentive dosage form that floats, expands, and finally breaks apart, or changes/collapses to allow emptying of the dosage form from the GI tract and the patient.

The terms "osmotic dosage form" and the like, as used herein, refer to a push-pull osmotic dosage form containing a pull layer and a push layer, wherein the push layer swells to push the pull layer through an orifice, out of the dosage form. In certain embodiments, the pull layer can comprise two or more layers.

The term "osmosis," as used herein, refers to movement of a solvent from a solution of low solute concentration to a solute or a solution of high solute concentration through a semipermeable or permeable membrane. The term "osmotic agent" includes swellable hydrophilic polymers, and osmogens/ionic compounds consisting of inorganic salts.

The terms "active agent," "active ingredient," "active pharmaceutical agent," "active pharmaceutical ingredient," and "drug," as used interchangeably herein, refer to an active pharmaceutical ingredient (API) compound, composition of matter, or mixture thereof that provides a therapeutic or prophylactic effect in the treatment of a disease or abnormal physiological condition. The active agent should be understood to include the neutral form of the drug, as well as pharmaceutically acceptable salts, solvates, esters, and prodrugs thereof.

The term "pharmaceutically acceptable," when used in connection with the pharmaceutical compositions of the disclosed subject matter, refers to molecular entities and compositions that are physiologically tolerable and do not typically produce untoward reactions when administered to a human. As used herein, the term "pharmaceutically acceptable" can also refer to being approved by a regulatory agency of the Federal or a state government or listed in the U.S. Pharmacopeia, National Formulary and Drug Standard Laboratory (NF), or other generally recognized pharmacopeia for use in animals, and more particularly in humans.

The term "bioavailability," as used herein refers to the fraction of an administered drug that reaches the systemic circulation, as measured through various pharmacokinetic metrics such as $C_{max}$, $T_{max}$, $AUC_{0-t}$, and $AUC_{0-inf}$.

The terms "dosage form," "formulation," "composition," and "pharmaceutical composition," as used interchangeably herein, refer to pharmaceutical drug products in the form in which they are marketed for use, with specific mixture of active pharmaceutical ingredients and inactive excipients, in a particular configuration, e.g., tablets, capsules, particles, and apportioned into a particular dose.

The term "simulated gastric fluid," as used herein, refers to fluid medium that is used to mimic chemical environment of gastric medium in vitro.

The term "gastric fluid," as used herein, refers to medium occurring in stomach of an individual.

The terms "dissolution medium" and "medium simulating gastric conditions," as used interchangeably herein, refer to a medium of dissolution that is used to mimic gastric fluid conditions in an individual. In certain embodiments, the dissolution medium comprises pH 4.5 acetate buffer; 0.01N HCl; 0.001N HCl with 10 mM NaCl; or 0.01N HCL with 150 mM NaCl.

The term "light meal medium," as used herein, refers to medium simulating gastric medium of an individual after consumption of a light meal. The term "light meal medium" refers to an aqueous medium comprising sodium chloride, potassium chloride, potassium hydrogen phosphate, calcium chloride, citric acid, and sugar.

The term "degradable," as used herein, refers to capable of being chemically and/or physically modified, dissolved, or broken down, e.g., in the body of a patient, within a relevant time period.

The term "prolonged period" or the like, as used herein, refers to a period that lasts for about an hour to several hours, e.g., about 1 hour to about 24 hours, e.g., about 5 hours to about 18 hours (e.g., between about 12 hours and about 18 hours). A prolonged period (or the like) includes 1, 2, 3, 4, 5, 6, 7, 8, 9, 10, 11, 12, 13, 14, 15, 16, 17, 18, 19, 20, 21, 22, 23, 24, or more hours.

The terms "swellable" and "swelling," as used herein with respect to a polymer, can be used interchangeably and refer to a polymer that swells by imbibing fluid and/or trapping $CO_2$.

The terms "expanding" and "expansion," as used herein with respect to a membrane, can be used interchangeably and refer to stretching or distention of the membrane due to an outward pressure (e.g., gas pressure, or pressure due to swelling of a polymer in the core) on the membrane.

The term "rapidly expanding" as used herein with respect to a membrane, refers to expansion of the membrane being faster than swelling of the core due to imbibition of fluid and generation of $CO_2$. In certain embodiments, the term "rapidly expanding" refers to expansion of the membrane to provide at least 50% volume gain of the dosage form from its initial volume in about 30 minutes or less.

The terms "shear" and "shear effect," as used herein, can be used interchangeably and refer to peristaltic waves moving from the midcorpus of the stomach to the pylorus, particularly in a fed state.

The terms "pore former" and the like, as used herein, refer to water-soluble polymers and/or water-soluble small molecules that will form pores or channels (i.e., behave as a channeling agent) in the functional coat/membrane, thereby increasing the permeability of the membrane.

The term "permeable membrane," as used herein, refers to a polymeric membrane or a film that is substantially permeable to the passage of solutes and passage of fluids/solvents. The "permeable membrane" can contain sparingly soluble polymers with or without a pore former(s), or insoluble polymers with a pore former(s), that will allow particles and fluids to pass through membrane by diffusion.

The term "semipermeable membrane," as used herein, refers to a polymeric membrane or a film that is substantially impermeable to the passage of solutes, including drug and other excipients/ingredients and substantially permeable to passage of fluids/solvents.

The term "substantially free," as used herein, refers to excluding any functional (e.g., noncontaminating) amount, which refers to any amount that contributes or has an effect on release profile or lag time of the composition.

The terms "orifice" and "hole," as used herein, can be used interchangeably and include, but are not limited to, at least one opening/exit means in the coatings of the osmotic gastroretentive composition to provide fluid communication with the pull layer. The opening can be formed via manual or laser drilling of the membrane coat and seal coats, often into the side facing the pull layer.

The term "patient," as used herein, refers to a human or nonhuman mammal that may need to receive an osmotic gastroretentive dosage form of the present disclosure.

The terms "treating" and "treatment," as used herein, can be used interchangeably and refer to obtaining a desired pharmacological and physiological effect. The effect can be prophylactic in terms of preventing or partially preventing a disease, symptom, or pathological condition and/or can be therapeutic in terms of a partial or complete alleviation or cure of a disease, condition, symptom, or adverse effect attributed to a pathological condition. Thus, "treatment" (and the like) covers any treatment of a disease in a mammal, particularly in a human, and includes, but is not limited to: (a) preventing a pathological condition from occurring in an individual who may be predisposed to develop the condition but, e.g., has not yet been diagnosed as having such condition (e.g., causing the clinical symptoms of such condition not to develop); (b) inhibiting, arresting, or reducing the development of the pathological condition or its clinical symptoms; and (c) relieving symptoms associated with the pathological condition.

The term "upper GI tract," as used herein, refers to the stomach, and proximal parts of the small intestine, e.g., the duodenum and jejunum.

The term "lower GI tract," as used herein, refers to distal parts of the small intestine, e.g., the ileum, and all of the large intestine, including the colon, cecum, and rectum.

The term "floating" or the like, and as used herein in conjunction with a "floating gastroretentive dosage form" or the like, refers to a dosage form that has a bulk density less than gastric fluid and simulated gastric fluid (SGF). Such dosage forms are "floating" in that they remain buoyant in the gastric fluids of the stomach or SGF for a targeted period of time.

The term "floating lag time," as used herein, includes the time between the addition of a dosage form to a medium and the time when the dosage form begins to float on the surface of the medium (e.g., in an in vitro setting), or the time between the consumption of a dosage form by a user and the time when the dosage form begins to float on the surface of the gastric fluid (e.g., in an in vivo setting).

The term "dissolution lag time," as used herein, refers to the time between the addition of a dosage form to a medium and the time when the active agent begins to dissolve in the medium.

The term "medium," as used herein, refers to a dissolution medium in an in vitro setting and gastric fluid in an in vivo setting.

The term "viscosity gradient," as used herein, refers to a difference in viscosity between adjacent layers of the multilayered gastroretentive dosage forms of the disclosure. The term "decreasing viscosity gradient," as used herein, refers to a decrease in viscosity from the push layer to the pull layer, wherein the push layer and the pull layer are adjacent to each other, or a decrease in viscosity between adjacent pull layers.

The term "modified release," as used herein, refers to dosage forms or compositions that are formulated to modify drug release and drug availability, after administration, over a desired period of time that is longer than a corresponding immediate release period, thereby allowing a reduction in dosing frequency. Modified release dosage forms or compositions can include, but are not limited to, "extended release," "controlled release," "controlled extended release," "delayed release," and "pulsatile release" dosage forms or compositions.

The terms "extended release," "controlled release," and "controlled extended release," as used herein, can be used interchangeably and refer to modified release dosage forms or compositions that are formulated to maintain targeted concentration of the administered drug, over an extended period of time after administration, as compared to a drug presented as an immediate release dosage form.

The term "delayed release," as used herein, refers to modified release dosage forms or compositions that are formulated to release a discrete portion or portions of drug at a time other than promptly after administration.

The term "pulsatile release" as used herein, refers to modified release dosage forms or compositions that are formulated to release discrete portions of drug in discrete pulses at discrete intervals after administration.

The term "highly soluble," as used herein, refers to drugs/active pharmaceutical agents/active agents with a solubility of greater than about 100 mg/ml of water; the term "moderately soluble," as used herein, refers to drugs/active pharmaceutical agents/active agents with a solubility of between about 100 mg/ml and about 1 mg/ml of water; the term "sparingly soluble" (or "poorly soluble"), as used herein, refers to drugs/active pharmaceutical agents/active agents with a solubility of between about 1 mg/ml and about 0.1 mg/ml of water; and the term "insoluble," as used herein, refers to drugs/active pharmaceutical agents/active agents with a solubility of less than about 0.1 mg/ml of water.

6.2. Self-regulating, Osmotic, Floating Gastroretentive Dosage Forms

The present disclosure provides self-regulating, osmotic gastroretentive compositions that, when in contact with gastric fluid/SGF, float in about 30 minutes or less, expand in about one hour or less to a size that prevents their passage through the pyloric sphincter, and remain in an expanded state for prolonged periods, e.g., about 6-24 hours. In certain embodiments, the compositions can provide extended release of an active pharmaceutical agent, as well as, optionally, immediate release of the same or different active pharmaceutical agent. In certain embodiments, the compositions of the disclosure can provide delayed release or delayed extended release of an active pharmaceutical agent. The compositions of the disclosure include: i) a swellable multilayered tablet core comprising a pull layer and a push layer; and ii) a rapidly expanding permeable (or semipermeable) elastic membrane surrounding the swellable core, wherein the membrane comprises a plasticizer and at least one ammonium polymethacrylate copolymer, e.g., a copolymer of ethyl acrylate, methyl methacrylate, and trimethylammonioethyl methacrylate chloride. In certain embodiments, the membrane can comprise cellulose acetate and a pore former, e.g., polyethylene glycol (PEG).

In certain embodiments of the disclosure, the self-regulating, osmotic gastroretentive composition, which continues to swell and eventually breaks apart, or collapses for emptying from the GI tract, after release of at least about 80% of the drug from the system, comprises: (i) a swellable multilayer tablet core comprising a pull layer comprising an active agent, a gas-generating agent, and at least one swellable water-soluble hydrophilic polymer; and a push layer comprising at least one swellable water-soluble hydrophilic polymer, and at least one osmogen; and (ii) a permeable elastic membrane, containing an orifice/hole in fluid communication with the pull layer, over the bilayer tablet core, and comprising a plasticizer and at least one ammonium polymethacrylate copolymer. In certain embodiments, the multilayered tablet core is a bilayered tablet core.

In certain embodiments, the self-regulating, osmotic gastroretentive compositions of the disclosure can remain in an expanded state in the stomach of a patient, and provide efficient delivery of drugs in the GI tract for prolonged periods, due to the presence of at least one polyethylene oxide, having an average molecular weight of greater than or equal to 600,000, in the push layer, that swells via imbibition of water from gastric fluid to (1) increase the size of the dosage form to promote gastric retention, (2) osmotically control the release of drug by providing a constant pressure on the pull layer comprising the drug dispersion/solution, (3) support the membrane and maintain the integrity of the tablet in a swollen state for prolonged periods, and (4) entrap generated gas (e.g., $CO_2$) to provide buoyancy. In certain embodiments, the oral, osmotic, floating gastroretentive compositions of the disclosure are stable, and provide desired controlled delivery of drug in the GI tract due to the presence of at least one polyethylene oxide, having an average molecular weight of about 200,000, and optionally, a small amount of polyethylene oxide, having an average molecular weight of greater than or equal to 600,000, in the pull layer. In certain embodiments, the tablet core swells to support the membrane, and both the tablet core and the membrane maintain the integrity of the dosage form. In certain embodiments, the tablet core swells and entraps $CO_2$ to provide buoyancy to the dosage form. In certain embodiments, the swelling of the tablet core is due to the swelling of the pull layer and the push layer.

For the purpose of illustration and not limitation, FIG. 1 provides a schematic representation of the gastroretentive dosage form, according to certain embodiments, illustrating a bilayer tablet core, comprising a Push layer and a Pull layer, Seal coat-1 surrounding the tablet core, a Permeable elastic membrane surrounding Seal coat-1, Seal coat-2 surrounding the permeable elastic membrane, a cosmetic coat surrounding Seal coat-2, and an Orifice passing through Seal coat-1, the Permeable membrane, and Seal coat-2, wherein the Orifice is in fluid communication with the Pull layer.

6.2.1. Swellable Multilayered Tablet Core

In certain embodiments, the swellable multilayered tablet core comprises a push layer and a pull layer. In certain embodiments, the pull layer and the push layer are compressed horizontally into a bilayer tablet core. In certain embodiments, the multilayered tablet core can comprise a push layer between two pull layers. In certain embodiments, the ratio of the pull layer and the push layer in the tablet core is between about 1:1 to about 6:1. In certain embodiments, the ratio of the pull layer and the push layer in the tablet core is about 1:1, about 2:1, about 3:1, about 4:1, about 5:1, about 6:1, or any intermediate ratios therein.

6.2.1.1. Pull Layer

In certain embodiments, the pull layer includes an active pharmaceutical agent, a swellable water-soluble hydrophilic polymer, an acid, and a gas-generating agent. In certain embodiments, the swellable water-soluble hydrophilic polymer is a low viscosity hydroxypropyl methylcellulose, hydroxypropyl cellulose, carbomer, or polyethylene oxide, e.g., POLYOX™. In certain embodiments, the pull layer includes a polyethylene oxide having an average molecular weight of less than or equal to 1,000,000. In certain embodiments, the polyethylene oxide has an average molecular weight of about 100,000, about 200,000, about 300,000, about 400,000, about 500,000, about 600,000, about 700,000, about 800,000, about 900,000, about 1,000,000, or intermediate values therein. In certain embodiments, the pull layer further includes a binder, a disintegrant, and a stabilizer to prevent degradation of the polyethylene oxide. In certain embodiments, the presence of disintegrant is optional. In certain embodiments, the pull layer includes a weakly basic drug(s). In certain embodiments, the pull layer includes a drug with any level of solubility, e.g., highly soluble, moderately, and sparingly soluble drug(s). In certain embodiments, the solubility of moderately or sparingly soluble drugs is improved via hot-melt extrusion, milling, nanomilling, or spray drying. In certain embodiments, the pull layer can include drugs with any polymorphic form, e.g., crystalline or amorphous form. In certain embodiments, the pull layer includes intermediate drug granules that contain drug; and extragranular excipients, compressed into a pull layer blend. In certain embodiments, intermediate drug granules are made via dry granulation or wet granulation. In certain embodiments, the drug is blended with excipients via hot-melt extrusion or spray drying to obtain a push layer blend. In certain embodiments, the intermediate drug granules comprise an active agent, a hydrophilic polymer, an acid, a binder, a stabilizer, and (optionally) a disintegrant. In certain embodiments, the extragranular components comprise at least one gas-generating agent(s). In certain embodiments, the gas-generating agent(s) is present in intermediate drug granules and/or an extragranular portion. In certain embodiments, the extragranular excipients can further include a filler, a glidant, and/or a lubricant. In certain embodiments, the acid present in the pull layer blend accelerates generation of $CO_2$ from gas-generating agents and/or stabilizes the drug. In certain embodiments, the acid is present in intermediate drug granules and/or an extragranular portion of the pull layer blend.

In certain embodiments, the polyethylene oxide present in the pull layer is a suspending agent and a release-controlling agent. In certain embodiments, the polyethylene oxide also acts as a binder. In certain embodiments, the average molecular weight of the polyethylene oxide (e.g., POLYOX™) in the pull layer affects drug release from the dosage form, e.g., an increase in the average molecular weight of the polyethylene oxide increases the viscosity of the pull layer and the control on drug release. In certain embodiments, the viscosity of the pull layer can be tailored to provide a desired drug release profile. In certain embodiments, the viscosity of the pull layer can be modified by mixing a small amount of polyethylene oxide with an average molecular weight of greater than or equal to 600,000 with at least one polyethylene oxide with an average molecular weight of less than or equal to 1,000,000, wherein the two polymers do not have the same average molecular weight. In certain embodiments, the pull layer includes a polyethylene oxide with an average molecular weight of about 100,000, about 200,000, about 300,000, about 600,000, or a mixture thereof, and a polyethylene oxide with an average molecular weight of about 2,000,000, about 4,000,000, about 5,000,000, or about 7,000,000. In certain embodiments, the pull layer includes a polyethylene oxide with an average molecular weight of about 200,000 and a polyethylene oxide with an average molecular weight of about 2,000,000, about 4,000,000, about 5,000,000, or about 7,000,000. In certain embodiments, the pull layer includes a polyethylene oxide with an average molecular weight of greater than or equal to 600,000 and a polyethylene oxide with an average molecular weight of less than or equal to 1,000,000 in a ratio of between about 1:99 and about 10:90. In certain embodiments, the total amount of polyethylene oxide in the pull layer ranges from about 5 wt % to about 80 wt %, from about 10 wt % to about 75 wt %, from about 15% to about 70 wt %, from about 20 wt % to about 65 wt % from about 25 wt % to about 60 wt % from about 30 wt % to about 55 wt %, from about 35 wt % to about 50 wt %, about 30 wt %, about 25 wt %, about 20 wt %, about 15 wt %, about 10 wt %, about 5 wt %, or any intermediate values therein, of the pull layer blend.

In certain embodiments, the pull layer includes a binder(s) selected from the group consisting of, but not limited to, povidone K 90, hypromellose, starch, acacia, gellan gum, low viscosity hydroxypropyl cellulose, methylcellulose, sodium methylcellulose, polyvinyl alcohol, polyvinyl acetates (e.g., KOLLICOAT® SR), polyethylene oxide (e.g., POLYOX™), polyethylene glycol, alginates, pegylated polyvinyl alcohol, and any combination thereof. In certain embodiments, the binder is hydroxypropyl cellulose.

In certain embodiments, binders are present in an amount of about 0.5 wt % to about 20 wt % of the pull layer. In certain embodiments, the binders are present in an amount of about 0.5 wt %, about 0.6 wt %, about 0.7 wt %, about 0.8 wt %, about 0.9 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, or any intermediates values therein, of the pull layer.

In certain embodiments, the pull layer includes at least one stabilizer to prevent degradation of polyethylene oxide. In certain embodiments, the stabilizer is an antioxidant selected from the group consisting of, but not limited to, ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, and any combination thereof. In certain embodiments, the antioxidant is BHT. In certain embodiments, the stabilizer is present in an amount of from about 0.01 wt % to about 20 wt % of the pull layer. In certain embodiments, the stabilizer is present in an amount of about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.10 wt %, about 0.2 wt %, about 0.3 wt %, about 0.4 wt %, about 0.5 wt %, about 1 wt %, about 5 wt %, about 10 wt %, about 15 wt %, about 20 wt %, or any intermediate values therein, of the pull layer.

In certain embodiments, the pull layer includes at least one acid that accelerates generation of $CO_2$ from gas-generating agents. In certain embodiments, faster generation of $CO_2$ reduces floating lag time. In certain embodiments, the self-regulating osmotic gastroretentive dosage forms containing swellable polymers and a gas-generating agent(s) can rapidly float on gastric fluids because the gas generated and entrapped within the swellable polymers decreases the density of the system. In certain embodiments, the acid is selected from the group consisting of succinic acid, citric acid, acetic acid, malic acid, fumaric acid, stearic acid, tartaric acid, boric acid, benzoic acid, and combinations thereof. In certain embodiments, the acid is succinic acid or tartaric acid. In certain embodiments, generation of $CO_2$ from the gas-generating agents depends upon the particle size of the acid, e.g., a smaller particle size provides faster generation of $CO_2$. In certain embodiments, the presence of acid stabilizes the active agent. In certain embodiments, the acid is present in an amount of from about 5 wt % to about 50 wt % of pull layer. In certain embodiments, the acid is present in an amount of about 5 wt %, about 10 wt %, about 15 wt %, about 20 wt %, about 25 wt %, about 30 wt %, about 35 wt %, about 40 wt %, about 45 wt %, about 50 wt %, or any intermediate values therein, of pull layer.

In certain embodiments, the pull layer includes a gas-generating agent(s) for rapid expansion and flotation of the dosage form. The gas-generating agent(s) generates $CO_2$ with the imbibition of gastric fluid in the dosage form. In certain embodiments, the presence of acid in the pull layer accelerates generation of $CO_2$ with the imbibition of gastric fluid in the dosage form. In certain embodiments, a gas-generating agent(s) generates $CO_2$ independent of the fed or fasted state of an individual. Examples of gas-generating agents present in the pull layer include, but are not limited to, all organic and inorganic carbonates, e.g., carbonate and bicarbonate salts of alkali and alkaline earth metals, that can interact with acid for in situ gas generation. In certain embodiments, the gas-generating agent is sodium bicarbonate, sodium carbonate, magnesium carbonate, and/or calcium carbonate. In certain embodiments, a mixture of calcium carbonate and sodium bicarbonate provides desired sustained release of $CO_2$. In certain embodiments, the gas-generating agent(s) is present in an amount of from at least about 5 wt % to about 50 wt % of pull layer. In certain embodiments, the gas-generating agent is present in an amount of about 5 wt %, about 10 wt %, about 15 wt %, about 20 wt %, about 25 wt %, about 30 wt %, about 35 wt %, about 40 wt %, about 45 wt %, about 50 wt %, or any intermediate values therein, of pull layer.

In certain embodiments, the pull layer comprises a mixture of sodium bicarbonate and calcium carbonate as the gas-generating agent(s) and an acid, e.g., succinic acid. In certain embodiments, equinormal amounts of acid and gas-generating agent(s) are present in the pull layer.

In certain embodiments, the pull layer can comprise a superdisintegrant including carmellose calcium, carboxymethyl starch sodium, croscarmellose sodium, crospovidone (crosslinked homopolymer of N-vinyl-2-pyrrolidone), low-substituted hydroxypropyl celluloses, sodium starch glycolate, colloidal silicon dioxide, alginic acid and alginates, acrylic acid derivatives, and various starches, or any combinations thereof.

In certain embodiments, the pull layer includes at least one lubricant selected from the group comprising magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combinations thereof. In certain embodiments, the lubricant is magnesium stearate. In certain embodiments, the lubricant is present in an amount of from about 0.5 wt % to about 5 wt % of the pull layer. In certain embodiments, the lubricant is present in an amount of about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.5 wt %, about 3 wt %, about 3.5 wt %, about 4 wt %, about 4.5 wt %, about 5 wt %, or any intermediate values therein, of the pull layer.

In certain embodiments, the pull layer includes at least one glidant selected from the group comprising talc, colloidal silicon dioxide, magnesium trisilicate, powdered cellulose, starch, tribasic calcium phosphate, and any combination thereof. In certain embodiments, the glidant is colloidal silicon dioxide. In certain embodiments, the glidant is present in an amount of from about 0.1 wt % to about 5 wt % of the pull layer. In certain embodiments, the glidant is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.5 wt %, about 2 wt %, about 2.5 wt %, about 3 wt %, about 3.5 wt %, about 4 wt %, about 4.5 wt %, about 5 wt %, or any intermediate valued therein, of the pull layer.

In certain embodiments, the pull layer further comprises mannitol. In certain embodiments, mannitol is used as a filler and/or as a compression aid. In certain embodiments, mannitol is used as a secondary osmotic agent. In certain embodiments, mannitol is present in an amount of from about 1 wt % to about 20 wt % of the pull layer.

In certain embodiments, the pull layer can include a placebo layer, and an active layer containing at least one active pharmaceutical agent. In certain embodiments, the placebo layer includes at least one polyethylene oxide having an average molecular weight of less than or equal to 1,000,000. In certain embodiments, the pull layer includes multiple active layers containing same drug to provide drug release with increasing drug concentration. In certain embodiments, the multiple active layers contain different drugs.

6.2.1.2. Push Layer

In certain embodiments, the push layer includes a swellable water-soluble hydrophilic polymer, an osmogen, a lubricant, and a color pigment. In certain embodiments, the swellable water-soluble hydrophilic polymer is polyethylene oxide, e.g., POLYOX™. In certain embodiments, polyethylene oxide in the push layer has an average molecular weight of greater than or equal to 600,000. In certain embodiments, average molecular weight of the polyethylene oxide in the push layer is about 600,000, about 700,000, about 800,000, about 900,000, about 1,000,000, about 2,000,000, about 3,000,000, about 4,000,000, about 5,000, 000, about 6,000,000, about 7,000,000, or any intermediate values thereof. In certain embodiments, the amount of polyethylene oxide in the push layer is sufficient to provide complete drug recovery (i.e., the pull layer is totally expelled); the remaining dosage form, with push layer only, breaks apart, or collapses/shrinks for complete emptying of the composition from the GI tract and the patient. In certain embodiments, polyethylene oxide is present in an amount of amount 50 wt % to about 95 wt % of the push layer. In certain embodiments, the polyethylene oxide is present in an amount of about 50 wt %, about 55 wt %, about 60 wt %, about 65 wt %, about 70 wt %, about 75 wt %, about 80 wt %, about 85 wt %, about 90 wt %, about 95 wt %, or any intermediate values therein, of the push layer. In certain embodiments, the polyethylene oxide is present in an amount of amount 10 wt % to about 30 wt % of the coated tablet composition. In certain embodiments, the polyethylene oxide is present in an amount of about 11 wt %, about 12 wt %, about 13 wt %, about 14 wt %, about 15 wt %, about 16 wt %, about 17 wt %, about 18 wt %, about 19 wt %, about 20 wt %, about 25 w %, about 30 wt %, or any intermediate values therein, of the coated tablet composition.

In certain embodiments, the amount and the average molecular weight of the polyethylene oxide in the push layer affects the drug release profile. In certain embodiments, the average molecular weight of the polyethylene oxide in the push layer is selected to provide enough expansion of the push layer for complete drug recovery in a desired time period. In certain embodiments, the average molecular weight of polyethylene oxide in the push layer provides complete drug recovery, while keeping the dosage form intact.

In certain embodiments, the push layer includes a lubricant selected from the group comprising magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, stearic acid, and any combinations thereof. In certain embodiments, the lubricant is magnesium stearate. In certain embodiments, the lubricant is present in an amount of from about 0.5 wt % to about 2 wt % of the push layer. In certain embodiments, the lubricant is present in an amount of about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, or any intermediate values therein, of the push layer.

In certain embodiments, the push layer comprises at least one osmogen. In certain embodiments, the osmogen includes ionic compounds of inorganic salts that provide a concentration differential for osmotic flow of liquid into the composition. The rate at which the water-soluble polymer in the push layer absorbs water depends on the osmotic pressure generated by the push layer and the permeability of the membrane coating. As the water-soluble polymer in the push layer absorbs water, it expands in volume, which pushes the drug solution or suspension present in the pull layer out of the tablet core through an orifice in the membrane. In certain embodiments, the presence of the orifice in the membrane prevents membrane tearing and keeps the dosage form intact. In certain embodiments, the orifice releases excess pressure built up during swelling of the dosage form, e.g., the push layer, and allows the membrane to remain intact under the hydrodynamic conditions of the GI tract. In certain embodiments, the presence of orifice in the membrane allows the composition to provide extended release of drug for about 6 hours to about 24 hours, without losing gastroretentive attributes of the system (GRS attributes), and break apart, or collapse for emptying from the GI tract and the patient. In certain embodiments, the osmogen is an ionic compound selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, and combinations thereof. In certain embodiments, the osmogen is sodium chloride. In certain embodiments, the osmogen is present in an amount of from about 5 wt % to about 30 wt % of the push layer. In certain embodiments, the osmogen is present in an amount of about 5 wt %, about 6 wt %, about 7 wt %, about 8 wt %, about 9 wt %, about 10 wt %, about 15 wt %, about 20 wt %, about 25 wt %, about 30 wt %, or any intermediate values therein, of the push layer.

In certain embodiments, the push layer includes at least one pigment for identifying the push layer in the multilayered tablet core. In certain embodiments, the pigment in the push layer is useful for identifying the push-layer side while drilling an orifice on the drug-layer side (pull-layer side) of the coated multilayered tablets. In certain embodiments, the push layer includes at least one pigment comprising iron oxide or lake-based colors. In certain embodiments, the pigment is a lake-based color. In certain embodiments, the pigment is an iron oxide pigment, e.g., oxide pigment black or Red blend. In certain embodiments, the pigment is present in an amount of from about 0.5 wt % to about 2 wt % of the push layer.

6.2.2. Membrane/Functional Coat

The compositions of the disclosure comprise a membrane that is a water-insoluble, permeable or semipermeable elastic membrane surrounding the multilayer tablet core. The membrane allows the flow of gastric fluid into the composition and initiates gas generation from gas-generating agents, and the membrane flexibility allows for rapid expansion and flotation of the composition. In certain embodiments, the membrane comprises a plasticizer and at least one copolymer of ethyl acrylate, methyl methacrylate, and trimethylammonioethyl methacrylate chloride (ammonium polymethacrylate copolymer).

The ammonium polymethacrylate copolymer provides permeability to the membrane and the plasticizer provides elasticity and mechanical strength to the membrane. The plasticizers provide elasticity to the membrane, ensuring that the membrane does not rupture upon expanding and that the osmotic gastroretentive drug delivery system provides the desired characteristics for drug release, hydrodynamic balance, and mechanical strength to withstand variations in pH and shear in the stomach during fed and fasted conditions. In certain embodiments, as dissolution of the drug in the tablet core proceeds, the plasticizer leaches out of the membrane. In certain embodiments, leaching of the plasticizer makes the membrane brittle, such that the membrane does not remain intact and the dosage form breaks into pieces by the end of drug release. Hydrophilic plasticizers suitable for the disclosure include, but are not limited to, glycerin, polyethylene glycols, polyethylene glycol monomethyl ether, propylene glycol, and sorbitol sorbitan solution. Hydrophobic plasticizers suitable for the disclosure include, but are not limited to, acetyl tributyl citrate, acetyl triethyl citrate, castor oil, diacetylated monoglycerides, dibutyl sebacate, diethyl phthalate, triacetin, tributyl citrate, triethyl citrate, gelucire 39/01, and gelucire 43/01. In certain embodiments, the plasticizers include various polyethylene glycols, glycerin, and/or triethyl citrate. In a preferred embodiment of the disclosure, the plasticizer is triethyl citrate.

In certain embodiments of the disclosure, the permeable elastic membrane comprises two (or more) polymers: at least one of EUDRAGIT® RL 30D (copolymer dispersion of ethyl acrylate, methyl methacrylate, and trimethylammonioethyl methacrylate chloride, 1:2:0.2), EUDRAGIT® RS 30D (copolymer dispersion of ethyl acrylate, methyl methacrylate, and trimethylammonioethyl methacrylate chloride, 1:2:0.1), EUDRAGIT® RL PO (copolymer solution of ethyl acrylate, methyl methacrylate, and trimethylammonioethyl methacrylate chloride, 1:2:0.2 in powder form), and EUDRAGIT® RS PO (copolymer solution of ethyl acrylate, methyl methacrylate, and trimethylammonioethyl methacrylate chloride, 1:2:0.1 in powder form) to improve permeability, and at least one of KOLLICOAT® SR 30D (dispersion of polyvinyl acetate, polyvinyl pyrolidone, and a sodium lauryl sulfate), EUDRAGIT® NE 30D (copolymer dispersion of ethyl acrylate and methyl methacrylate), and EUDRAGIT® NM 30D (copolymer dispersion of ethyl acrylate and methyl methacrylate), to improve mechanical strength (tensile strength). The membrane can further include a hydrophilic polymer and/or a water-soluble nonionic polymer that act(s) as a pore former, to modify its elasticity, permeability, and tensile strength.

In certain embodiments, the permeable elastic membrane provides desired characteristics for drug release and tensile strength to withstand peristalsis and mechanical contractility of the stomach (shear). The combination of (1) a water-soluble hydrophilic polymer in the tablet core, and (2) the unique permeable elastic membrane formed over the tablet core by the coating of a homogeneous dispersion of (a) at least one of EUDRAGIT® RL 30D, EUDRAGIT® RS 30D, EUDRAGIT® RL PO, and EUDRAGIT® RS PO (collectively "ammonium polymethacrylate copolymers") to improve permeability, and (b) at least one of KOLLICOAT® SR 30D, EUDRAGIT® NE 30D, and EUDRAGIT® NM 30D (collectively "neutral polymethacrylate copolymer dispersions") to improve mechanical strength (tensile strength), provides the desired extended drug release while maintaining the integrity of the tablet core in an expanded state, thus extending the gastric residence time and preventing the dosage form from being emptied from the stomach until substantial or complete release of the drug, usually after a prolonged period. In certain embodiments, at least one of EUDRAGIT® RL 30D/EUDRAGIT® RS 30D/EUDRAGIT® RL PO/EUDRAGIT® RS PO is present in a ratio with at least one of KOLLICOAT® SR 30D/EUDRAGIT® NE 30D/EUDRAGIT® NM 30D (i.e., RL/RS:SR/NE/NM) of between 0:100 and 100:0. In certain embodiments, at least one of EUDRAGIT® RL 30D/EUDRAGIT® RS 30D/EUDRAGIT® RL PO/EUDRAGIT® RS PO and at least one of KOLLICOAT® SR 30D/EUDRAGIT® NE 30D/EUDRAGIT® NM 30D are present in a ratio of between about 0.5:99.5 to about 99.5:0.5, including, but not limited to: 1:99, 2:98, 3:97, 4:96, 5:95, 6:94, 7:93, 8:92, 9:91, 10:90, 11:89, 12:88, 13:87, 14:86, 15:85, 16:84, 17:83, 18:82, 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:56, 45:55, 46:54, 47:53, 48:52, 49:51, 50:50, 51:49, 52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, 99:1, or any intermediate values thereof.

In certain embodiments, the permeable elastic membrane comprises at least one of EUDRAGIT® RL PO and/or EUDRAGIT® RS PO (i.e., a powder copolymer of ethyl acrylate, methyl methacrylate, and trimethylammonioethyl methacrylate chloride). In certain embodiments, the permeable elastic membrane is formed over the multilayer tablet core by coating the core with a solution of EUDRAGIT® RL PO (powder copolymer of ethyl acrylate, methyl methacrylate, and trimethylammonioethyl methacrylate chloride (1:2:0.2)) and/or EUDRAGIT® RS PO (copolymer of ethyl acrylate, methyl methacrylate, and trimethylammonioethyl methacrylate chloride (1:2:0.1)), a plasticizer, and talc.

In certain embodiments, the membrane includes a water-insoluble polymer, a plasticizer, and at least one pore former comprising a water-soluble nonionic polymer. In certain embodiments, the pore formers and plasticizers modify membrane elasticity, permeability, and tensile strength. In certain embodiments, the membrane does not include any pore former. In certain embodiments, examples of insoluble permeable components of the permeable elastic membrane include, but are not limited to, copolymers of ethyl acrylate, methyl methacrylate, and trimethylammonioethyl methacrylate chlorides (e.g., EUDRAGIT® RL 30D or EUDRAGIT® RS 30D, EUDRAGIT® RS PO, EUDRAGIT® RL PO)); cellulose acetate phthalate; ethyl cellulose; and hypromellose acetate succinate.

In certain embodiments, examples of insoluble components of the permeable elastic membrane that provide elasticity to the membrane include, but are not limited to, copolymers of ethyl acrylate and methyl methacrylate (e.g., EUDRAGIT® NE 30D, EUDRAGIT® NM 30D), a dispersion of polyvinyl pyrolidone and polyvinyl acetate (e.g., KOLLICOAT® SR 30D), thermoplastic polyurethanes, ethylene-vinyl acetate, and polydimethylsiloxane.

In certain embodiments, the permeable elastic membrane is a coating of a homogeneous dispersion of EUDRAGIT® RL 30D/EUDRAGIT® RS 30D and EUDRAGIT® NE 30D/EUDRAGIT® NM 30D. In certain embodiments, the coating dispersion does not include any neutral polymethacrylate copolymer. In certain embodiments, the permeable elastic membrane is a coating of a homogeneous dispersion of EUDRAGIT® RL 30D/EUDRAGIT® RS 30D and KOLLICOAT® SR 30D. In certain embodiments, the strength of the membrane depends upon compatibility/homogeneity of the water-insoluble polymers present in the coating dispersion. In certain embodiments, compatibility of the water-insoluble polymers present in the coating dispersion is improved in the presence of a surfactant. In certain embodiments, the compatibility of water-insoluble polymers present in the coating dispersion is improved by forming the dispersion at a pH of between about 2 and about 7. In certain embodiments, the homogeneous dispersion is formed by mixing EUDRAGIT® RL 30D/EUDRAGIT® RS 30D and EUDRAGIT NE 30D/EUDRAGIT® NM 30D, or EUDRAGIT® RL 30D/EUDRAGIT® RS 30D and KOLLICOAT® SR 30D, in presence of a surfactant and a water-soluble polymer, e.g., polyvinyl pyrrolidone. In certain embodiments, the homogeneous dispersion is formed by mixing EUDRAGIT® RL 30D/EUDRAGIT® RS 30D, EUDRAGIT NE 30D/EUDRAGIT® NM 30D, and polyvinyl pyrrolidone, or EUDRAGIT® RL 30D/EUDRAGIT® RS 30D, KOLLICOAT® SR 30D, and polyvinyl pyrrolidone, in a pH-controlled environment, e.g., at a pH of between about 2 and about 7. In certain embodiments, the homogeneous dispersion is formed by mixing EUDRAGIT® RL 30D/EUDRAGIT® RS 30D and EUDRAGIT NE 30D/EUDRAGIT® NM 30D, or EUDRAGIT® RL 30D/EUDRAGIT® RS 30D and KOLLICOAT® SR 30D, in the absence of a surfactant or a water-soluble polymer, or in the absence of both.

In certain embodiments, the permeable elastic membrane is a coating of a solution of EUDRAGIT® RL PO and/or EUDRAGIT® RS PO. In certain embodiments, the tablet core is coated with a solution of EUDRAGIT® RL PO and/or EUDRAGIT® RS PO in a suitable solvent. In certain embodiments, the solvent used for coating comprises acetone, water, ethanol, isopropyl alcohol, or a mixture thereof. In certain embodiments, the solvent is a mixture of acetone and water, a mixture of ethanol and isopropyl alcohol, a mixture of acetone and isopropyl alcohol, a mixture of isopropyl alcohol and water, or a mixture of water, ethanol, and isopropyl alcohol. In certain embodiments, the solvent is a mixture of acetone and water. In certain embodiments, the ratio of solvent and water ranges from about 80:20 to about 99:1. In certain embodiments, the ratio of acetone and water is about 80:20, about 85:15, about 90:10, or about 95:5.

In certain embodiments, the coating dispersion includes at least one of EUDRAGIT® RL PO and EUDRAGIT® RS PO (collectively "ammonium polymethacrylate copolymers") to improve permeability, and at least one plasticizer to improve mechanical strength (tensile strength). In certain embodiments, powder forms of EUDRAGIT®, e.g., EUDRAGIT® RL PO and EUDRAGIT® RS PO, are preferred over EUDRAGIT® dispersions, e.g., EUDRAGIT® RS 30D and EUDRAGIT® RL 30D. It was unexpectedly observed that a membrane comprising EUDRAGIT® RL PO and/or EUDRAGIT® RS PO and a plasticizer, provided superior membrane properties, e.g., membrane strength, permeability, and elasticity, in comparison to a membrane comprising a polymer to enhance permeability (e.g., EUDRAGIT® RL 30D, EUDRAGIT® RS 30D) and a polymer to enhance elasticity (e.g., EUDRAGIT NE 30D, EUDRAGIT NM 30D, KOLLICOAT® SR 30D). In certain embodiments, permeability, elasticity, and tensile strength of the membrane determines the floating lag time and floating time (duration of floating) of the osmotic gastroretentive delivery system of the disclosure. In certain embodiments, the membrane permeability, elasticity, and tensile strength is determined by permeability and elasticity of the polymers present in the membrane. In certain embodiments, the compositions of the disclosure exhibit increase in floating time and decrease in floating lag time with increasing membrane permeability. In certain embodiments, permeability of copolymer of ethyl acrylate, methyl methacrylate, and trimethylammonioethyl methacrylate chloride is enhanced on exchange of chloride anion with other anions. In certain embodiments, the chloride anion is exchanged with nitrate ions, sulfate ions, succinate ions, or acetate ions. In certain embodiments, exchange of chloride anions with anions of higher hydrated anion radius improves membrane permeability.

In certain embodiments, permeability of the permeable elastic membrane is tailored to provide a floating lag time of less than or equal to 30 minutes and floating time of from about 1 hour to about 24 hours (e.g., about 1 hour to about 18 hours). In certain embodiments, the oral, osmotic, controlled release, floating gastroretentive dosage form of the disclosure comprises a membrane containing a copolymer(s) of ethyl acrylate, methyl methacrylate, and trimethylammonioethyl methacrylate chloride, e.g., EUDRAGIT® RL PO or EUDRAGIT® RS PO, and exhibits a floating lag time of less than or equal to 15 minutes and a floating time of from about 1 hour to about 18 hours. In certain embodiments, the copolymer of ethyl acrylate, methyl methacrylate, and trimethylammonioethyl methacrylate chloride is present in an amount of between about 70% and about 90% w/w of the combined weight of the plasticizer and the copolymer to provide desired tensile strength, and elasticity for rapid expansion of the membrane. In certain embodiments, the plasticizer is present in an amount of between about 10 wt % and about 25 wt %, between about 10 wt % and about 20 wt %, between about 10 wt % and about 15 wt %, and any intermediate ranges therein, of the copolymer of ethyl acrylate, methyl methacrylate, and trimethylammonioethyl methacrylate chloride (ammonium polymethacrylate copolymer) to provide desired tensile strength, and elasticity for rapid expansion of the membrane. In certain embodiments, the plasticizer is present in an amount of at least about 10 wt %, at least about 11 wt %, at least about 12 wt %, at least about 13 wt %, at least about 14 wt %, at least about 15 wt %, at least about 16 wt %, at least about 17 wt %, at least about 18 wt %, at least about 19 wt %, at least about 20 wt %, at least about 21 wt %, at least about 22 wt %, at least about 23 wt %, at least about 24 wt %, and at least about 25 wt % of the ammonium polymethacrylate copolymer.

In certain embodiments, the membrane further includes an anti-tacking agent, selected from the group consisting of talc, colloidal silicon dioxide, magnesium trisilicate, powdered cellulose, starch, and tribasic calcium phosphate. In certain embodiments, the anti-tacking agent is colloidal silicon dioxide. In certain embodiments, the anti-tacking is present in an amount of from about 5 wt % to about 30 wt % of the ammonium polymethacrylate copolymer. In certain embodiments, the glidant is present in an amount of about 5 wt %, about 10 wt %, about 15 wt %, about 20 wt %, about 25 wt %, about 30 wt %, or any intermediate values therein, of the ammonium polymethacrylate copolymer.

In certain embodiments, the compositions of the disclosure comprise a membrane that is a water-insoluble, semipermeable elastic membrane surrounding the multilayer tablet core. In certain embodiments, the semipermeable membrane is inert and maintains its integrity to provide constant osmotic pressure during drug delivery. In certain embodiments, the semipermeable membrane comprises one or more pH-independent water-insoluble polymers that are permeable to water and substantially impermeable to solutes, e.g., drugs and excipients. Polymers suitable for inclusion in the semipermeable membrane comprise, but are not limited to, cellulose esters, e.g., cellulose acetate, cellulose acetate butyrate, and cellulose triacetate. In certain embodiments, the semipermeable membrane comprises cellulose acetate. In certain embodiments, the permeability of the semipermeable membrane can be enhanced by increasing the acetyl content in cellulose acetate.

In certain embodiments, the membrane includes an orifice in fluid communication with the pull layer. In certain embodiments, the drug is released through the orifice, at a desired release rate, based on the average molecular weight of the polyethylene oxide in the push and the pull layers. In certain embodiments, the swelling rate of polyethylene oxide in the push layer depends upon the amount of osmogen, and the average molecular weight of polyethylene oxide present in the push layer. In certain embodiments, the size of the orifice in the membrane and average molecular weight of polyethylene oxide in the pull layer controls the release of the drug from the dosage form. In certain embodiments, the multilayer tablet core comprises a push layer between two pull layers, and a semipermeable membrane surrounds the core. In certain embodiments, the semipermeable membrane includes two orifices, one each in fluid communication with each of the two pull layers. In certain embodiments, the semipermeable membrane includes multiple orifices.

6.2.3. Immediate Release Drug Layer

In certain embodiments, the self-regulating, osmotic, floating gastroretentive compositions of the disclosure provide a biphasic drug release comprising an immediate release and an extended release of same or different drugs. In certain embodiments, the compositions of the disclosure provide a biphasic drug release comprising an immediate release and an extended release of same drug to cover lag time associated with the extended release of the drug. In certain embodiments, the compositions providing a biphasic drug release contain one or more immediate release drug layers over the permeable elastic membrane containing an orifice. In certain embodiments, the immediate release drug layer comprises an active agent/drug for immediate release, a film-forming polymer and, optionally, other excipients known in the art. In certain embodiments, the immediate release drug layer is further coated with an additional layer, e.g., an over coat/cosmetic coat comprising a powder or a film that prevents adherence of the dosage form to itself during manufacturing and storage. In certain embodiments, the immediate release drug layer is present immediately below the cosmetic coat. In certain embodiments, the active agent in the immediate release drug layer and the active agent in the core are different. In certain embodiments, a cosmetic coat surrounds the permeable or semipermeable membrane or the immediate release drug layer. In certain embodiments, the immediate release drug layer is surrounded by a seal coat, a cosmetic coat over the seal coat, and a final coat/clear coat over the cosmetic coat, wherein the final coat/clear coat is the outermost layer. In certain embodiments, the immediate release drug layer is surrounded by a seal coat, and a cosmetic coat, wherein the cosmetic coat is the outermost layer.

Examples of soluble film-forming polymers that can be used in the immediate release drug layer include, but are not limited to, soluble cellulose derivatives, e.g., methyl cellulose; hydroxypropyl cellulose; hydroxyethyl cellulose; hypromellose; various grades of povidone; polyvinyl alcohol-polyethylene glycol copolymer, e.g., KOLLICOAT® IR; soluble gums; and others. The films can further comprise antioxidants, surface-active agents, plasticizers and humectants, such as PEGs, various grades of polysorbates, and sodium lauryl sulfate.

6.2.4. Seal Coat, Over Coat/Cosmetic Coat, and Final Coat/Clear Coat

In certain embodiments, the permeable or semipermeable elastic membrane is coated with a cosmetic coat comprising OPADRY® II, Pink (mixture of titanium dioxide, talc, guar gum, partially hydrolyzed poly vinyl alcohol, maltodextrin, HPMC, medium chain glyceride, iron oxide red, and iron oxide blue), OPADRY® II, green (mixture of titanium dioxide, talc, guar gum, partially hydrolyzed polyvinyl alcohol, maltodextrin, HPMC, medium chain glyceride, FD&C Blue/Brilliant Blue, Aluminum Lake, and FD&C Yellow/Tartrazine Aluminum Lake, Aluminum Lake), or OPADRY® II, Blue (mixture of titanium dioxide, talc, guar gum, partially hydrolyzed poly vinyl alcohol, maltodextrin, HPMC, medium chain glyceride, FD&C Blue/Indigo Carmine Aluminum Lake blue). In certain embodiments, cosmetic coat helps in easy swallowing of the tablets, especially in pediatric and geriatric populations. In certain embodiments, the cosmetic coat makes the tablet slippery when in contact with saliva. In certain embodiments, the cosmetic coat makes the tablet look smaller than its actual size.

In certain embodiments, the cosmetic coat is surrounded by a clear coat. One skilled in the art can readily appreciate that clear coats are known in the art and commercially available. Accordingly, any commercially available clear coat can be used in the presently disclosed embodiments. One nonlimiting example of a clear coat is OPADRY® EZ clear (mixture of talc, guar gum, maltodextrin, HPMC, and medium chain glyceride).

In certain embodiments, the composition comprises a seal coat (Seal Coat-1) between the multilayered tablet core and the permeable or semipermeable elastic membrane. In certain embodiments, the composition includes a seal coat (Seal Coat-2) between the permeable or semipermeable elastic membrane and the cosmetic coat. In certain embodiments, the compositions include a cosmetic coat over the permeable elastic membrane. In certain embodiments, the composition includes a multilayer tablet core coated with a seal coat (Seal Coat-1), a permeable elastic membrane over Seal Coat-1, an additional seal coat (Seal Coat-2) over the permeable elastic membrane, and a cosmetic coat over Seal Coat-2. In certain embodiments, the compositions with an IR drug layer comprise an IR drug layer over Seal Coat-2, Seal Coat-3 over the IR drug layer, and a cosmetic coat over Seal Coat-3.

In certain embodiments, the seal coat(s) comprises a pH-independent, water-soluble polymer containing a hypromellose-based polymer or a polyvinyl acetate-based polymer. In certain embodiments, the hypromellose-based polymer(s) comprises hydroxypropyl methylcellulose (HPMC), hydroxypropyl cellulose (HPC), hydroxyethyl cellulose (HEC), or combinations thereof. In certain embodiments, the seal coat(s) comprises povidone. In certain embodiments, the seal coat (Seal Coat-1, Seal Coat-2, and/or Seal Coat-3) comprises a mixture of guar gum, maltodextrin, HPMC, and medium chain triglycerides (OPADRY® II, clear). In certain embodiments, Seal Coats are present in an amount of from about 0.1 wt % to about 5 wt % of the uncoated core, membrane-coated core, or core with drug layer. In certain embodiments, Seal Coat-1 is present in an amount of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.5 wt %, about 2 wt %, about 2.5 wt %, about 3 wt %, about 3.5 wt %, about 4 wt %, about 4.5 wt %, about 5 wt %, or any intermediate values therein, of the uncoated core, membrane-coated core, or core with drug layer.

In certain embodiments, the composition includes a multilayer tablet core coated with Seal Coat-1, a semipermeable elastic membrane over Seal Coat-1, Seal Coat-2 over the semipermeable elastic membrane, and a cosmetic coat over Seal Coat-2. In certain embodiments, the compositions with IR layer comprise an IR drug layer over Seal Coat-2, Seal Coat-3 over the IR drug layer, and a cosmetic coat over Seal Coat-3.

6.2.5. Gastroretentive Dosage Compositions

In certain embodiments, the gastroretentive dosage forms of the disclosure comprise a multilayered core coated with a permeable membrane containing an orifice. In certain embodiments, the multilayered core comprises a pull layer and a push layer. In certain embodiments, the pull layer can comprise from about 100 mg, to about 400 mg, from about 150 mg to about 350 mg, from about 200 mg to about 350 mg, from about 240 mg to about 320 mg, about 200 mg, about 240 mg, about 315 mg, or about 320 mg of levodopa. In certain embodiments, the pull layer can further comprise from about 50 mg to about 100 mg, from about 55 mg to about 95 mg, from about 60 mg to about 90 mg, from about 75 mg to about 85 mg, from about 70 mg to about 80 mg, about 55 mg, about 65 mg, and about 85 mg of carbidopa. In certain embodiments, the pull layer can further comprise from about 140 mg to about 200 mg, from about 145 mg to about 195 mg, from about 150 mg to about 190 mg, from about 155 mg to about 185 mg, from about 160 mg to about 180 mg, about 141 mg, about 148 mg, about 190 mg, about 193 mg, about 200 mg of POLYOX™ N80. In certain embodiments, the pull layer can further comprise from about 1 mg to about 10 mg, or about 5 mg of POLYOX™ N303. In certain embodiments, the pull layer can further comprise from about 5 mg to about 10 mg, or about 8 mg of hydroxypropyl cellulose. In certain embodiments, the pull layer can further comprise from about 50 mg to about 125 mg, from about 60 mg to about 100 mg, about 50 mg, about 75 mg, about 100 mg, or about 125 mg of succinic acid. In certain embodiments, the pull layer can further comprise from about 25 mg to about 125 mg, about 50 mg, or about 100 mg of sodium bicarbonate. In certain embodiments, the pull layer can further comprise from about 20 mg to about 80 mg, about 25 mg, or about 75 mg of calcium carbonate. In certain embodiments, the pull layer can further comprise from about 0.1 mg to about 1 mg, or about 0.5 mg of α-tocopherol. In certain embodiments, the pull layer can further comprise from about 1 mg to about 5 mg, or about 3.5 mg of Cab-O-Sil®. In certain embodiments, the pull layer can further comprise from about 40 mg to about 55 mg, about 44 mg, or about 52 mg of mannitol. In certain embodiments, the pull layer can further comprise from about 1 mg to about 5 mg, or about 3 mg of magnesium stearate. In certain embodiments, the push layer can comprise from about 200 mg to about 250 mg, about 220 mg, or about 218 mg of POLYOX™ N60. In certain embodiments, the push layer can further comprise from about 20 mg to about 30 mg, or about 25 mg of sodium chloride. In certain embodiments, the push layer can further comprise from about 1 mg to about 5 mg, or about 3 mg of magnesium stearate. In certain embodiments, the push layer can further comprise from about 1 mg to about 5 mg, about 2 mg, or about 4 mg of color pigment. In certain embodiments, the coating system can comprise from about 30 mg to about 50 mg, about 35 mg, or about 40 mg of a hydroxypropyl cellulose based polymer (OPADRY® EZ clear). In certain embodiments, the coating system can further comprise from about 100 mg to about 200 mg, from about 125 mg to about 175 mg, from about 145 mg to about 150 mg, about 112 mg, or about 148 mg of ammonio methacrylate copolymer (EUDRAGIT® RL PO). In certain embodiments, the coating system can further comprise from about 10 mg to about 60 mg, from about 15 mg to about 50 mg, from about 20 mg to about 40 mg, about 16 mg, or about 22 mg, of triethyl citrate. In certain embodiments, the coating system can further comprise from about 20 mg to about 40 mg, about 22 mg, or about 29 mg of talc. In certain embodiments, the gastroretentive tablets can comprise an immediate release (IR) drug layer comprising carbidopa, levodopa, hydroxypropyl cellulose, α-tocopherol, and succinic acid. In certain embodiments, the IR drug layer can comprise from about 15 mg to about 20 mg, or about 17.5 mg of carbidopa. In certain embodiments, the IR drug layer can comprise from about 50 mg to about 75 mg, or about 65 mg of levodopa. In certain embodiments, the IR drug layer can further comprise from about 10 mg to about 20 mg, or about 15 mg of hydroxypropyl cellulose. In certain embodiments, the IR drug layer can further comprise from about 0.1 mg to about 1 mg, or about 0.5 mg of α-tocopherol. In certain embodiments, the IR drug layer can further comprise from about 1 mg to about 5 mg, or about 3.5 mg of succinic acid.

6.3. Active Agents

As noted above, the self-regulating, osmotic, floating gastroretentive drug delivery compositions of the disclosure are particularly beneficial for drugs that have at least one of the following characteristics: a variable transit time through various regions of the GI tract, a narrow absorption windows (NAW) in particular regions of GI tract, susceptibility to degradation in an alkaline environment, a requirement for an acidic environment for maximum solubility, and a propensity to precipitate in alkaline environments. The osmotic gastroretentive drug delivery systems of the present disclosure are useful in providing improved drug delivery, independent of drug solubility. Drugs that can be used in the osmotic gastroretentive drug delivery systems of the present disclosure include, but are not limited to, the following groups of agents: alcohol abuse preparations, drugs used for Alzheimer's disease, anesthetics, acromegaly agents, analgesics, anti-asthmatics, anticancer agents, anticoagulant and antithrombotic agents, anticonvulsants, antidiabetic agents, antiemetics, antiglaucoma agents, antihistamines, anti-infective agents, anti-Parkinson's agents, antiplatelet agents, antirheumatic agents, antispasmodics and anticholinergic agents, antitussives, carbonic anhydrase inhibitors, cardiovascular agents, cholinesterase inhibitors, treatment of CNS disorders, CNS stimulants, contraceptives, cystic fibrosis management, dopamine receptor agonists, endometriosis management, erectile dysfunction therapy, fertility agents, gastrointestinal agents, immunomodulators and immunosuppressives, memory enhancers, migraine preparations, muscle relaxants, nucleoside analogues, osteoporosis management, parasympathomimetics, prostaglandins, psychotherapeutic agents, sedatives, hypnotics and tranquilizers, drugs used for skin ailments, steroids, and hormones.

In certain embodiments, the osmotic gastroretentive drug delivery system of the disclosure can be used for all classes of drugs/active pharmaceutical agents that can take advantage of the gastroretentive dosage forms for improved local or systemic delivery. Examples of such drugs include drugs producing a local effect the in stomach, weakly basic drugs, drugs with reduced bioavailability, drugs with higher stability in gastric region, drugs with NAW, and drugs interfering with normal gut flora in the colon.

Examples of drugs producing a local effect in the stomach include, but are not limited to, $H_1$ receptor agonists, antacids, agents for treatment of *Helicobacter pylori* (*H. pylori*), gastritis, gastric ulcers/cancer including misoprostol, amoxicillin, tetracycline, metronidazole, rebamipide, sulfasalazine, and their salts. In addition, active pharmaceutical agents that act locally include, but are not limited to, drugs for the treatment of local infections, drugs for the treatment of various GI diseases and symptoms (e.g., misoprostol for gastric ulcers), or drugs for the treatment of metabolic disorders, for the treatment of local cancers, or for the treatment of cancer-related diseases.

Weakly basic drugs that can be included in the osmotic gastroretentive drug delivery system of the disclosure include, but are not limited to, acetaminophen, forecoxa, celecoxib, morphine, codeine, oxycodone, hydrocodone, diamorphine, pethidine, tramadol, buprenorphine, prazosin, nifedipine, lercanidipine, amlodipine besylate, trimazosin, doxazosin, hydroxyzine hydrochloride, lorazepam, buspirone hydrochloride, pazepam, chlordiazepoxide, meprobamate, oxazepam, trifluoperazine hydrochloride, clorazepate dipotassium, diazepam, abciximab, eptifibatide, tirofiban, lamifiban, clopidogrel, ticlopidine, dicumarol, heparin, warfarin, phenobarbital, methylphenobarbital, clobazam, clonazepam, clorezepate, diazepam, midazolam, lorazepam, felbamate, carbamazepine, oxcarbezepine, vigabatrin, progabide, tiagabine, topiramate, gabapentin, pregabalin, ethotoin, phenytoin, mephenytoin, fosphenytoin, paramethadione, trimethadione, ethadione, beclamide, primidone, brivaracetam, levetiracetam, seletracetam, ethosuximide, phensuximide, mesuximide, acetazolamide, sulthiame, methazolamide, zonisamide, lamotrigine, pheneturide, phenacemide, valpromide, valnoctamide, repaglinide, nateglinide, metformin, phenformin, rosiglitazone, pioglitazone, troglitazone, miglitol, acarbose, exanatide, vildagliptin, sitagliptin, tolbutamide, acetohexamide, tolazamide, glyburide, glimepiride, gliclazide, glipizide, chlorpropamide, pseudoephedrine, phenylephrine, oxymetazoline, mepyramine, antazoline, diphenhydramine, carbinoxamine, doxylamine, clemastine, dimenhydrinate, pheniramine, chlorpheniramine, dexchlorpheniramine, brompheniramine, tripolidine, cyclizine, chlorcyclizine, hydroxyzine, meclizine, promethazine, trimeprazine, cyproheptadine, azatadine, ketotifen, dextromethorphan, noscapine, ethyl morphine, codeine, chlorambucil, lomustine, tubulazole, echinomycin, betamethasone, prednisolone, aspirin, piroxicam, valdecoxib, carprofen, celecoxib, flurbiprofen, (+)-N-{4-[3-(4-fluorophenoxy)phenoxy]-2-cyclopenten-1-yl}-N-hyroxyurea, timolol, nadolol, dextromethorphan, noscapine, ethyl morphine, theobromine, codeine, actinomycin, dactinomycin, doxorubicin, daunorubicin, epirurubicin, bleomycin, plicamycin, mitomycin, alprenolol, carteolol, levobunolol, mepindolol, metipranolol, nadolol, oxprenolol, penbutolol, pindolol, propranolol, sotalol, timolol, acebutolol, atenolol, betaxolol, bisoprolol, esmolol, metoprolol, nebivolol, carvedilol, celiprolol, labetalol, butaxemine, adalimumab, azathioprine, chloroquine, hydroxychloroquine, D-penicillamine, etanercept, sodium aurothiomalate, auranofin, infliximab, leflunomide, minocycline, sulfasalazine, hydrocortisone, prednisone, prednisolone, methylprednisolone, dexamethasone, betamethasone, triamcinolone, beclomethasone, aldosterone, acetaminophen, amoxiprin, benorilate, diflunisal, faislamine, diclofenac, aceclofenac, acemetacin, bromfenac, etodolac, indomethacin, nabumetone, sulindac, tolmetin, carprofen, ketorolac, mefenamic acid, matamizole, oxyphenbutazone, sulfinprazone, piroxicam, lornoxicam, meloxicam, tenoxicam, celecoxib, etoricoxib, lumiricoxib, parecoxib, rofecoxib, valdecoxib, numesulide, iloperidone, ziprasidone, olanzepine, thiothixene hydrochloride, fluspirilene, risperidone, penfluridole, ampakine, atorvastatin calcium, cerivastatin, fluvastatin, lovastatin, mevastatin, pitavastatin, pravastatin, rosuvastatin, simvastatin, dexadrine, dexfenfluramine, fenfluramine, phentermine, orlistat, acarbose, rimonabant, sildenafil citrate, carbenicillin indanylsodium, bacampicillin hydrochloride, troleandomycin, doxycyline hyclate, ampicillin, penicillin G, oxytetracycline, minocycline, erythromycin, spiramycin, acyclovir, nelfinavir, virazole, benzalkonium chloride, chlorhexidine, econazole, terconazole, fluconazole, voriconazole, metronidazole, thiabendazole, oxiendazole, morantel, cotrimoxazole, alfaxalone, etomidate, levodopa, bromocriptine, pramipexole, ropinirole, pergolide, selegiline, trihexyphenidyl, benztropine mesylate, procyclidine, biperiden, ethopropazine, diphenhydramine, dolphenadrine, amantadine, donepezil, pyridostigmine, rivastigmine, galantamine, tacrine, minocycline, rifampin, erythromycin, nafcillin, cefazolin, imipenem, aztreonam, gentamicin, sulfamethoxazole, vancomycin, ciprofloxacin, trimethoprim, metronidazole, clindamycin, telcoplanin, mupirocin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin, isocarboxazid, phenelzine, tranylcypromine, azidovudine (AZT), didanosine (dideoxyinosine, ddI), d4T, zalcitabine (dideoxycytosine, ddC), nevirapine, lamivudine (epivir, 3TC), saquinavir, ritonavir, indinavir delavirdine, [R—(R*S*)]-5-chloro-N-[2-hydroxy-3-{methoxymethylamino}-3-oxo-1-(phenylmethyl)propy]-1H-indole-2-carboxamide, 5-chloro-1H-indole-2-carboxylic acid [(1S)-benzyl-(2R)-hydroxy-3-((3R,4S)-dihydroxy-pyrrolidin-1-yl)-3-o-xypropyl]amide, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]4-[(3,5-Bis-trifluoromethyl-benzyl)-methoxycarbonyl-amino]-2-eth-yl-6-trifluoromethyl-3,4-dihydro-2H-quinoline-1-carboxylic acid isopropyl ester, caffeine, methylphenidate, cabergoline, pramipexole, dolasetron, granisetron, ondansetron, tropisetron, palonosetron, domperidone, droperidol, dimenhydrinate, haloperidol, chlorpromezine, promethazine, prochlorperizine, metoclopramide, alizapride, loperamide, cisapride, chlorpromazine, thioridazine, prochlorperizine, haloperidol, alprazolam, amitriptyline, bupropion, buspirone, chlordiazepoxide, citalopram, clozapine, diazepam, fluoxetine, fluphenazine, fluvoxamine, hydroxyzine, lorezapam, loxapine, mirtazepine, molindone, nefazodone, nortriptyline, olanzepine, paroxetine, phenelzine, quetiapine, risperidone, sertraline, thiothixene, tranylcypromine, trazodone, venlafaxine, ziprasidone, hydromorphone, fentanyl, methadone, morphine, oxycodone, oxymorphone, naltrexone, sodium valproate, nitrazepam, phenytoin, famonizatidine, cimetidine, ranitidine, albuterol, montelukast sodium, nicorandil, iloperidone, clonazepam, diazepam, lorazepam, baclofen, carisoprodol, chlorzoxazone, cyclobenzaprine, dantrolene, metaxalone, orphenadrine, pancuronium, tizanidine, dicyclomine, clonidine, gabapentin, and salbutamol.

Examples of suitable drugs with greater stability in the gastric region are liothyronine ($T_3$), levothyroxine ($T_4$), $T_3/T_4$ combinations, captopril, ranitidine HCL, metformin, tetracycline, and metronidazole.

Examples of suitable drugs with NAW are aspirin, levodopa, p-aminobenzoic acid, metronidazole, amoxicillin, sulfonamides, quinolones, penicillins, cephalosporins, aminoglycosides, liothyronine ($T_3$), levothyroxine ($T_4$), $T_3/T_4$ combinations, and tetracyclines.

Examples of suitable drugs that interfere with normal gut flora in the colon include orally active antibiotics such as ampicillin and amoxicillin.

Each named drug, here and throughout the specification, should be understood to include the neutral form of the drug, as well as pharmaceutically acceptable salts, solvates, esters, and prodrugs thereof.

6.4. Methods of Treating

In certain embodiments, the disclosure provides methods for treating conditions that require active pharmaceutical agents to produce maximum benefit with minimum side effects when absorbed in upper GI tract, rather than, e.g., the colon. For example, the disclosure provides oral, osmotic controlled, floating gastroretentive dosage forms containing orally administered antibiotics, e.g., tetracycline, metronidazole, amoxicillin, and/or clindamycin, that possess a potential for altering the normal flora of GI tract, and particularly, the flora of colon, resulting in release of various toxins causing nausea, diarrhea, and life-threatening side effects.

In certain embodiments, the disclosure provides methods for improving the bioavailability of drugs that are susceptible to degradation by intestinal enzymes, e.g., ranitidine and metformin hydrochloride. The method comprises preventing degradation of such drugs from intestinal enzymes by administering the drugs in the gastroretentive dosage forms of the disclosure.

In certain embodiments, as a nonlimiting example, the disclosure provides methods for treating Parkinson's disease (PD), comprising administering self-regulating, oral, osmotic, floating gastroretentive compositions of carbidopa (CD) and levodopa (LD). The gastroretentive CD/LD compositions of the disclosure provide and maintain stable plasma CD and LD concentrations and are superior to the marketed extended release compositions containing CD and LD, e.g., SINEMET® ER and RYTARY®, that have been approved by the FDA for treating PD. PD patients on such dosage forms wake up in the morning having little or no mobility due to the wearing off of the dose taken the day/evening before ("off-time"). Once the previous dose has worn off, the patients are usually unwilling, or even unable, to wait for the extended period of time required for an extended release dosage form to deliver the necessary plasma levels of LD. While the use of an immediate release formulation of LD can reduce this "wait time," the use of an immediate release formulation of LD requires more frequent dosing and is associated with more fluctuating plasma LD concentrations. The gastroretentive CD/LD compositions of the disclosure provide extended release with reduced lag time and stable plasma LD concentrations for extended period, thus reducing off-time.

In certain embodiments, the disclosure provides methods for improving patient compliance comprising providing oral, osmotic controlled, floating gastroretentive compositions suitable for once- or twice-daily administration. In certain embodiments, the disclosure provides methods for improving patient compliance in PD patients. The method comprises providing once-a-day or twice-a-day administration of self-regulating, oral, osmotic, floating gastroretentive compositions of CD and LD in patients with PD. The CD/LD compositions of the disclosure provide extended release with steady plasma concentrations of CD and LD for at least about 8 hours, e.g., between about 8 hours and about 14 hours, or between about 10 hours and about 14 hours. The gastroretentive CD/LD compositions of the disclosure reduce off-time, increase "on" time without disabling dyskinesia, and reduce the severity of dyskinesia in comparison to the standard oral extended release formulations.

In certain embodiments, the disclosure provides minimizing lag time and improving patient compliance in PD patients. The method comprises administering, to a PD patient, an oral, osmotic controlled, floating gastroretentive composition of the disclosure containing an IR drug layer that provides immediate release of CD/LD to minimize lag time/wait time for the period of time required for an extended release dosage form to deliver the necessary plasma levels of LD.

In certain embodiments, the disclosure provides methods for improving compliance in PD patients by administering gastroretentive CD/LD compositions of the disclosure that reduce off-time, increase "on" time without disabling dyskinesia, and reduce the severity of dyskinesia in comparison to the standard oral extended release formulations In certain embodiments, the disclosure provides methods of improving the bioavailability of a weakly basic drug. The method comprises administering to the patient, an oral, osmotically controlled, floating gastroretentive composition containing a weakly basic drug to provide extended release with enhanced pharmacokinetic attributes of the drug, e.g., reduced lag time, avoidance of low trough levels, and reduced peak-to-trough ratios ($C_{max}/C_{min}$). The composition enhances drug solubility by releasing the weakly basic drug in the acidic microenvironment of the stomach, and enhances drug absorption by releasing the drug near its site of absorption. The composition enhances drug solubility, provides extended release of the drug for at least about 8 hours, e.g., between about 8 hours and about 14 hours, or between about 10 hours and about 14 hours, without losing gastroretentive attributes of the system (GRS attributes), and breaks into fragments, or collapses after complete release of the drug from the system.

In certain embodiments, the disclosure provides oral, self-regulating, osmotic controlled, floating gastroretentive compositions that reduce side effects and improve patient compliance by releasing drug near the absorption site, rather than in a distal region (e.g., the colon, where the drug can potentially alter normal gut flora and release dangerous toxins causing nausea, vomiting, and other life-threatening side effects).

In a specific embodiment, the present disclosure provides a method for treating a condition that requires extended release of an active pharmaceutical agent that is absorbed in the upper gastrointestinal tract, the method includes administering to a subject a self-regulating, osmotic, floating gastroretentive dosage form. The dosage form includes a) a multilayer core comprising a pull layer containing the active pharmaceutical agent, an acid, and a gas-generating agent; and a push layer, and b) a permeable elastic membrane surrounding the multilayer core, wherein the permeable elastic membrane contains at least one orifice and at least one ammonium polymethacrylate copolymer.

In a specific embodiment, the present disclosure provides a method for treating Parkinson's disease, the method includes administering to a Parkinson's disease patient a self-regulating, osmotic, floating gastroretentive dosage form. The dosage form includes a) a multilayer core comprising a pull layer containing an active pharmaceutical agent(s) suitable for treating Parkinson's disease, an acid, and a gas-generating agent; and a push layer, and b) a permeable elastic membrane surrounding the multilayer core, wherein the permeable elastic membrane contains at least one orifice and at least one ammonium polymethacrylate copolymer.

6.5. Methods of Making

In certain embodiments, the disclosure provides methods for preparing oral, osmotic controlled, floating gastroretentive compositions. The methods comprise making a pull layer blend and a push layer blend; horizontally pressing the pull layer blend and the push layer blend into bilayered tablet cores; coating the bilayered tablet cores with a coating system comprising a seal coat(s), a functional coat/membrane, a cosmetic coat/over coat, and a clear coat.

In certain embodiments. the coating system can further contain an IR drug layer. In certain embodiments, the compositions comprise a bilayered tablet core coated with a coating system containing various coats in the following order: bilayered tablet core coated with Seal coat-1, Permeable Membrane/Functional coat over Seal coat-1, Seal coat-2 over Permeable Membrane/Functional coat; IR drug layer over Seal coat-2; Seal coat-3 over IR drug layer; Cosmetic coat over Seal coat-3, and Clear coat over Cosmetic coat.

In certain embodiments, the pull layer blend comprises drug, at least one polyethylene oxide, a stabilizer, a binder, an acid, a gas-generating agent, a filler, a glidant, and at least one lubricant. In certain embodiments, the at least one polyethylene oxide has an average molecular weight of less than about 1,000,000, for example, an average molecular weight of about 100,000, about 200,000, about 300,000, about 400,000, about 500,000, about 600,000, about 700,000, about 800,000, about 900,000, about 1,000,000, or intermediate values therein.

In certain embodiments, the push layer can comprise at least one polyethylene oxide, an osmogen, a pigment, and a lubricant. In certain embodiments, the at least one polyethylene oxide can have an average molecular weight of about 600,000, about 700,000, about 800,000, about 900,000, about 1,000,000, about 2,000,000, about 3,000,000, about 4,000,000, about 5,000,000, about 6,000,000, about 7,000,000, or any intermediate values therein.

In certain embodiments, the seal coat(s) can comprise OPADRY® II, clear; the functional coat can comprise EUDRAGIT® RL PO; the cosmetic coat can comprise OPADRY® II, Pink/Green/Blue; and the final coat can comprise OPADRY® EZ, clear.

In certain embodiments, the IR drug layer can comprise a drug(s) for IR and a binder. In certain embodiments, the coating system can include an orifice. In certain embodiments, the orifice is drilled manually or is drilled with a laser. In certain embodiments, the cosmetic coat and the clear coat do not include any orifice. In certain embodiments, the orifice in the coating system can be in fluid communication with the pull layer.

In certain embodiments, the pull layer includes a weakly basic drug(s). In certain embodiments, the pull layer includes a drug with any level of solubility, e.g., a highly soluble, moderately soluble, sparingly soluble, or insoluble drug(s). In certain embodiments, the solubility of moderately or sparingly soluble drugs is improved via hot-melt extrusion, milling, nanomilling, or spray drying. In certain embodiments, the pull layer can include drugs with any polymorphic form, e.g., crystalline or amorphous form. In certain embodiments, the pull layer includes intermediate drug granules (which contain drug) and extragranular excipients, compressed into a pull layer blend. In certain embodiments, intermediate drug granules are made via dry granulation or wet granulation. In certain embodiments, the drug is blended with excipients via hot-melt extrusion or spray drying to obtain a pull layer blend. In certain embodiments, the intermediate drug granules comprise an active agent, a hydrophilic polymer, an acid, a binder, a stabilizer, and (optionally) a disintegrant. In certain embodiments, the extragranular components comprise at least one gas-generating agent(s). In certain embodiments, the gas-generating agent(s) is present in intermediate drug granules and/or an extragranular portion. In certain embodiments, the extragranular excipients can further include a filler, a glidant, and/or a lubricant.

In a specific embodiment, the present disclosure includes a method for making a self-regulating, osmotic, floating gastroretentive dosage form, wherein the method includes making a pull layer blend containing a drug, and a push layer blend; horizontally compressing the pull layer blend and the push layer blend into a bilayered tablet core; coating the bilayered tablet core with a permeable elastic membrane; and drilling an orifice into the permeable elastic membrane to provide fluid communication with the pull layer. Specifically, making the pull layer blend includes making intermediate drug granules containing the drug, and mixing the drug granules with extragranular excipients into a pull layer blend. The intermediate drug granules include the drug, polyethylene oxide, and an acid, and the extragranular excipients include a filler, a glidant, and a lubricant. Making the push layer blend includes mixing an osmogen, polyethylene oxide, a color pigment, and a lubricant into a push layer blend; and wherein the permeable elastic membrane contains at least one ammonium polymethacrylate copolymer and at least one plasticizer.

6.6. Features of the Dosage Forms

Those skilled in the art will recognize that gastroretentive dosage forms should be designed not only with a control on the release rate of the drug (temporal control) but also a control on the location of the drug delivery (spatial control). Spatial control for delivery of a drug involves increasing gastric retention time by using a composition containing swellable polymers in admixture with a gas-generating agent(s) to form systems that are large enough in size to prevent their passage through the pyloric sphincter, as well as capable of floating on gastric fluids. Those skilled in the art will recognize that systems containing swellable polymers and gas-generating agents can rapidly float on gastric fluids because the gas generated and entrapped within the swellable polymers decreases the density of the system. Further swelling of the floating system to a size that prevents its passage through the pyloric sphincter is an important factor in gastric retention of the system. Floating drug delivery systems that do not exhibit sufficient swelling (e.g., having a size less than about 5-7 mm) show delayed gastric emptying in fed conditions but can still be emptied from the stomach because their size is smaller than the pyloric sphincter; this can be more likely if the patient is in the supine position. It has been reported that dosage forms with a size of approximately 12-18 mm diameter in their expanded state are generally excluded from passage through the pyloric sphincter (see, e.g., U.S. Patent Application Publication No. 2010/0305208). The system should also be capable of retaining this size in gastric fluid for a prolonged period under hydrodynamic conditions created by gastric motility (e.g., shear effect). Thus, the combination of rapid flotation, a rapid increase in size to prevent passage through the pyloric sphincter, and retaining the expanded size under hydrodynamic conditions of the stomach in fed and fasted states, results in increased gastric retention of a gastroretentive system.

The self-regulating, osmotic, floating gastroretentive compositions of the disclosure contain an acid(s) and a gas-generating agent(s) to initiate rapid flotation and swelling of the compositions. In certain embodiments, the gas-generating agent(s) include carbonate and bicarbonate salts. In certain embodiments, the acid is succinic acid and gas-generating agent(s) include sodium bicarbonate and calcium carbonate. It was observed that the amount and molecular weight of polyethylene oxide in the push layer is critical to the gastric retention time and duration of extended release from the dosage form. Compositions of the present disclosure provide extended release or combined immediate release and extended release gastroretentive systems satisfying the following four important attributes of gastroretentive systems: rapid flotation, rapid increase in size to prevent passage through the pyloric sphincter, retention of the expanded size under hydrodynamic conditions of the stomach in fed and fasted states, and collapsing or breaking of the dosage form after the drug is released, thereby allowing the system, and any remaining contents, to be expelled from the stomach at an appropriate time.

The present disclosure addresses several of the needs in the art for oral controlled release compositions that can provide extended release, or combined immediate and extended release of drugs with NAW in the upper GI tract, weakly basic drugs with high pH-dependent solubility, drugs that act locally in upper GI tract, and drugs with any of the above characteristics that degrade in lower GI tract and/or disturb normal colonic microbes. The compositions of the disclosure can improve pharmacokinetic and pharmacodynamic properties of drugs with NAW, drugs that degrade in lower GI tract, and/or are stable in stomach.

The present disclosure provides extended release or combined immediate and extended release gastroretentive systems, with high or low drug loading capacity, to provide targeted extended release of drugs, independent of drug solubility, in the proximal GI tract for maximum therapeutic benefit.

The self-regulating, osmotic, floating gastroretentive compositions of the disclosure provide extended release of the drug, with uniform release profile and minimal pharmacokinetic variability.

In certain embodiments, the self-regulating gastroretentive compositions of the disclosure, in light-meal or heavy-meal conditions, swell to a size that prevents their passage through the pyloric sphincter, and the membrane of these compositions maintains the integrity of the system in a swollen state for a prolonged period of time under hydrodynamic conditions created by gastric motility (shear effect)

and pH variations. In certain embodiments, the gastroretentive compositions of the disclosure remain in the swollen state for at least about 6 hours, e.g., from about 10 hours to about 24 hours. Furthermore, as the pull layer containing the active pharmaceutical agent is released from the orifice and the push layer continues to swell, the dosage form becomes sufficiently empty (e.g., when at least about 80% of the active pharmaceutical agent is released), and finally collapses or breaks apart, for complete emptying from the GI system and the patient (i.e., the remainder of the composition passes through the pyloric sphincter and exits after passage through the rest of the GI tract). In certain embodiments, the dosage form becomes sufficiently empty after at least about 70% to about 100%, e.g., at least about 80%, of the drug is released. In certain embodiments, the oral, osmotic, controlled release, floating gastroretentive compositions of the disclosure regulate core swelling and membrane elasticity as a function of time to enable emptying of the gastroretentive composition from the GI tract.

In certain embodiments, the drug release from the oral, osmotic, controlled release, floating gastroretentive compositions of the disclosure is independent of various physiological factors within the GI tract, and the release characteristics of the composition can be predicted from the properties of the active pharmaceutical agent and the compositions. The compositions expand rapidly, predominantly independent of the physiological factors in the GI tract, and can be retained in the stomach for extended periods of time, e.g., at least about 10 hours to about 24 hours, regardless of stomach pH, by maintaining the tablet integrity in a swollen state, thus providing extended release of the drug under varying hydrodynamic and pH conditions.

In certain embodiments, each of the pull layer and the push layer contain at least one swellable hydrophilic water-soluble polymer to provide controlled drug release and prevent dose dumping. In certain embodiments, the pull layer comprises an active layer and a placebo layer. In certain embodiments, the pull layer comprises two active layers or multiple active layers. In certain embodiments, both the active layer and the placebo layer include at least one swellable hydrophilic water-soluble polymer (e.g., polyethylene oxide with an average molecular weight of less than or equal to 1,000,000).

In certain embodiments, the swellable water-soluble hydrophilic polymers, e.g., polyethylene oxide, in the push layer and the pull layer control drug release under varying hydrodynamic and pH conditions. In certain embodiments, controlled release of drug from the composition depends upon the grade/average molecular weight of polyethylene oxide in the pull layer, e.g., an increase in the molecular weight of polyethylene oxide in the pull layer reduces the release rate of the drug. In certain embodiments, the push layer comprises at least one polyethylene oxide having an average molecular weight of greater than or equal to 600,000. In certain embodiments, the average molecular weight of polyethylene oxide in the push layer determines the release rate of the drug. In certain embodiments, an increase in the average molecular weight of polyethylene oxide in the push layer increases the swelling volume of the polyethylene oxide that results from imbibition of gastric fluids. In certain embodiments, an increase in the average molecular weight of polyethylene oxide in the push layer increases drug recovery from the dosage form. In certain embodiments, the push layer contains polyethylene oxide with an average molecular weight of about 2,000,000 (POLYOX™ N60) and the pull layer contains polyethylene oxide with an average molecular weight of about 200,000 (POLYOX™ N80). In certain embodiments, the pull layer includes a mixture of polyethylene oxides having an average molecular weight of about 7,000,000 and about 200,000 that are present in a ratio of between about 1:99 and 10:90 respectively. In certain embodiments, the average molecular weights of the polyethylene oxides in the push layer and the pull layer are different enough to prevent mixing of the two layers, and provide a decreasing viscosity gradient from the push layer to the pull layer.

In certain embodiments, swellable water-soluble hydrophilic polymers in the pull layer and the push layer of the tablet core, and a permeable or semipermeable elastic membrane over the tablet core, containing an orifice in fluid communication with the pull layer, control the release of the drug for extended periods of time.

In certain embodiments, the gastroretentive composition includes at least one osmogen that provides a concentration gradient to facilitate osmotic flow of gastric fluid into the composition. In certain embodiments, the osmogen is present in the push layer. In certain embodiments, the osmogen is present in the pull layer and the push layer.

In certain embodiments, the oral, osmotic, controlled release, floating gastroretentive compositions of the disclosure exhibit a floating lag time of less than about 60 minutes, less than about 55 minutes, less than about 50 minutes, less than about 45 minutes, less than about 40 minutes, less than about 35 minutes, less than about 30 minutes, less than about 25 minutes, less than about 20 minutes, less than about 15 minutes, or any intermediate time periods therein, in 250 ml dissolution medium comprising 10 mM of NaCl in 0.001N HCl, at 15 rpm, measured using a rotating bottle method.

In certain embodiments, the oral, osmotic, controlled release, floating gastroretentive compositions of the disclosure exhibit a floating lag time of less than about 30 minutes, less than about 20 minutes, less than about 15 minutes, or any intermediate time periods therein, in 250 ml of pH 4.5 acetate buffer, buffer, at 15 rpm, measured using a rotating bottle method. In certain embodiments, the oral, osmotic, controlled release, floating gastroretentive compositions of the disclosure exhibit a floating lag time of between about 60 minutes and about 30 minutes or less in GI fluids. In certain embodiments, the floating lag time is independent of the pH of the dissolution medium.

The oral, osmotic, floating gastroretentive compositions of the disclosure markedly improve absorption and bioavailability of active pharmaceutical agents and, in particular, improve the absorption and bioavailability of drugs having a NAW in the proximal GI tract, due to the ability of the compositions to withstand peristalsis and mechanical contractility of the stomach (shear, or shear effect). Consequently, the compositions release the drug in an extended manner in the vicinity of absorption site(s), without premature transit into nonabsorbing regions of the GI tract. Unlike other formulations in the art that require a high calorie and/or high fat diet for maintaining gastric retention for up to 8-12 hours, the gastroretentive compositions of the disclosure provide gastric retention of the active pharmaceutical agents with NAW, for up to 24 hours, without premature transit in nonabsorbing regions of the GI tract, even in low or medium calorie diet conditions. In certain embodiments, presence of an orifice in the membrane prevents membrane tearing and keeps the dosage form intact for extended periods. The orifice releases excess pressure built up during swelling of the dosage form, e.g., swelling of the push layer, and allows the membrane to remain intact. In certain embodiments, the gastroretentive composition of the disclosure provides gastric retention of an active pharmaceutical agent for up to 1, 2, 3, 4, 5, 6, 7, 8, 9, 10, 11, 12, 13, 14, 15, 16, 17, 18, 19, 20, 21, 22, 23, 24 hours, or any intermediate periods therein. In certain embodiments, the gastroretentive composition of the disclosure provides gastric retention of an active pharmaceutical agent for between, e.g., about 1-24, about 10-20, about 12-18, and about 14-16 hours. In certain embodiments, the gastroretentive compositions of the disclosure provide gastric retention of an active pharmaceutical agent for at least about 10 hours.

In certain embodiments, the presently disclosed subject matter provides for a method of improving bioavailability of a weakly basic drug with a narrow absorption window in the upper gastrointestinal tract. Specifically, the method includes administering to a subject a self-regulating, osmotic, floating gastroretentive dosage form. This dosage form includes a) a multilayer core comprising a pull layer containing the weakly basic drug, an acid, and a gas-generating agent; and a push layer, and b) a permeable elastic membrane surrounding the multilayer core. The permeable elastic membrane contains at least one orifice and at least one ammonium polymethacrylate copolymer; and the dosage form provides a stable plasma concentration of the weakly basic drug for an extended period of time.

In certain embodiments, membrane permeability affects floating lag time and floating time of the composition. In certain embodiments, permeation of gastric fluid into the dosage form, and generation of $CO_2$ from the gas-generating agent, increases with increasing membrane permeability. In certain embodiments, floating lag time decreases with increasing membrane permeability. In certain embodiments, floating time increases with increasing membrane permeability. In certain embodiments the membrane comprises ammonium polymethacrylate copolymers. In certain embodiments, the membrane comprises ammonium acetate salts of polymethacrylate copolymers. In certain embodiments, chloride anions from ammonium chloride salts of polymethacrylate copolymers are replaced with acetate anions to enhance membrane permeability.

Without intending to be bound by any particular theory of operation, it is believed that the presence of a swellable, water-soluble hydrophilic polyethylene oxide (e.g., POLYOX™), a gas-generating agent, and an acid in the multilayered tablet core, and a water-insoluble permeable elastic membrane comprising EUDRAGIT® RL PO and/or EUDRAGIT® RS PO provides a rapidly expanding extended release gastroretentive composition with desired characteristics for drug release, hydrodynamic balance, and mechanical strength to withstand pH variations and shear effect in the stomach during fed and fasted conditions.

In certain embodiments, the gastroretentive compositions of the disclosure expand within 10-15 minutes, reaching a size that prevents their passage through the pyloric sphincter in 30 minutes or less. In certain embodiments, the gastroretentive compositions of the disclosure expand up to a 50% increase in volume (i.e., about 50% volume gain) over a period of about 30 minutes.

In certain embodiments, the dosage forms of the disclosure comprise multilayered tablets that are compressed horizontally into oval, modified oval, or capsule shapes for easy swallowing. In certain embodiments, the tablets are compressed using oval, modified oval, capsule shaped or any other shaping tool. In certain embodiments, the horizontally compressed multilayered tablets comprise a long axis having a length of between about 12 mm and about 22 mm, and a short axis having a length of between about 8 mm and about 11 mm. In certain embodiments, the multilayered tablets have a long axis of about 12 mm, about 13 mm, about 14 mm, about 15 mm, about 16 mm, about 17 mm, about 18 mm, about 19 mm, about 20 mm, about 21 mm, about 22 mm, or any intermediate lengths therein. In certain embodiments, the multilayered tablets have a short axis of about 8 mm, about 9 mm, about 10 mm, about 11 mm, or any intermediate lengths therein. In certain embodiments, the horizontally compressed multilayered tablets comprise a long axis having a length of about 20±2 mm, and a short axis having a length of between about 10±2 mm. In certain embodiments, the initial tablet size (10 mm×19 mm) is reasonably small for swallowability, and once swallowed, the tablet is designed for rapid generation of carbon dioxide ($CO_2$) within the core to increase its buoyancy. In certain embodiments, the tablet, during in vitro dissolution, floats within 30 minutes of coming into contact with dissolution medium, and transforms into an oblong shape with major and minor axes having lengths of about 26 mm and 18 mm respectively, which is maintained for more than 12 hours. Once the dosage form achieves the constant size, the push-pull system gets activated and drug is released at constant rate for about 6-24 hours of duration.

In certain embodiments, the gastroretentive compositions of the disclosure, when in contact with gastric fluid, or with media that simulate gastric conditions, expand within about 30-60 minutes to a size that prevents their passage through the pyloric sphincter of a human, and exhibit a floating lag time of less than about 30 minutes, e.g., less than about 29 minutes, less than about 28 minutes, less than about 27 minutes, less than about 26 minutes, less than about 25 minutes, less than about 24 minutes, less than about 23 minutes, less than about 22 minutes, less than about 21 minutes, less than about 20 minutes, less than about 19 minutes, less than about 18 minutes, less than about 17 minutes, less than about 16 minutes, less than about 15 minutes, less than about 14 minutes, less than about 13 minutes, less than about 12 minutes, less than about 11 minutes, less than about 10 minutes, or less than about 9 minutes. In certain embodiments, the shape and size of the tablet, e.g., oval-shaped horizontally compressed tablet comprising a long axis having a length of about 20±2 mm, and a short axis having a length of about 10±2 mm, prevents its passage through the pyloric sphincter of a human, with just a 50% increase in volume of the tablet in gastric fluid.

In certain embodiments, the gastroretentive compositions of the disclosure exhibit a breaking strength of greater than or equal to 15N.

In certain embodiments, the gastroretentive compositions of the disclosure exhibit a hardness of from about 5 kp to about 20 kp. In certain embodiments, hardness of the bilayered tablet core is about 5 kp, about 6 kp, about 7 kp, about 8 kp, about 9 kp, about 10 kp, about 11 kp, about 12 kp, about 13 kp, about 14 kp, about 15 kp, about 16 kp, about 17 kp, about 18 kp, about 19 kp, about 20 kp, or any intermediate value therein.

In certain embodiments, the gastroretentive compositions of the disclosure are suitable for once- or twice-daily administration. In certain embodiments, the gastroretentive compositions of the disclosure provide extended release of active pharmaceutical agents for a period of about 12-24 hours, under fed and/or fasted conditions.

In certain embodiments, the gastroretentive dosage form of the disclosure includes a rapidly expanding membrane with high tensile strength and elasticity that expands the dosage form in about 30 minutes (or less) to a size that prevents its passage through the pyloric sphincter of a human, and a multilayer tablet core, comprising at least one water-soluble hydrophilic polymer, surrounded by the membrane, that swells with imbibition and absorption of fluid and provides a controlled sustain release of the drug.

As noted above, in certain embodiments, the multilayer tablet core comprises gas-generating agent(s), e.g., carbonate and bicarbonate salts, that generate $CO_2$ in an acidic environment, e.g., gastric fluid. In certain embodiments, the multilayer tablet core further comprises organic and/or inorganic acids that react with carbonate/bicarbonate salts in an aqueous environment, e.g., independent of stomach pH, and generate $CO_2$ gas. In certain embodiments, the gas-generating agent generates $CO_2$ independent of a fed or fasted state of an individual. In certain embodiments, the membrane is highly elastic/flexible, due to the presence of at least one plasticizer, and expands rapidly with an outward pressure on the membrane from the generated $CO_2$ gas. In certain embodiments, the dosage form of the disclosure exhibits at least about 50% volume gain in about 30 minutes, at least about 150% volume gain in about 2 hours, and at least about 250% volume gain in about 4 hours, in about 200 ml of pH 4.5 acetate buffer, at 15 rpm, measured using a rotating bottle method. In certain embodiments, the dosage form exhibits 250% volume gain from about 4 hours to about 14 hours. In certain embodiments, the rate of swelling of the multilayer tablet core is synchronized with the rate of expansion of the membrane, such that the multilayer tablet core swells along with the expanding membrane. In certain embodiments, the tablet core swells at a rate such that the pull layer in the swollen core is facing the orifice in the expanded membrane and provides drug release through the orifice. In certain embodiments, the membrane expansion is responsible for an initial rapid expansion of the dosage form and the swellable multilayer tablet core within the membrane supports the expanded membrane.

In certain embodiments, the expanded dosage form collapses back to about 200% volume gain in about 16 hours or less, and about 150% volume gain in about 18 hours or less. In certain embodiments, the dosage form can squeeze due to release of drug and excipients from the tablet core, and effusion of $CO_2$ through the membrane into the surrounding environment.

In certain embodiments, the multilayer tablet core swells to a size that can support the expanded permeable or semipermeable elastic membrane. In certain embodiments, the permeable or semipermeable elastic membrane containing an orifice keeps the multilayer tablet core intact in a swollen condition for prolonged time periods and the dosage provides extended release of the drug for the prolonged time periods, e.g., 10-24 hours. In certain embodiments, the rate of generation of $CO_2$ and rate of expansion of membrane is enhanced with increasing membrane permeability. In certain embodiments, the expansion of the membrane is faster than the swelling of the tablet core. Such time differential in swelling of the membrane and the tablet core results in empty space between the tablet core and the membrane to accommodate generated $CO_2$, which keeps the dosage form in a swollen state for long time periods and enhances its gastric residence time.

In certain embodiments, the gastroretentive dosage forms of the disclosure provide extended release of moderately soluble and/or sparingly soluble drugs that exhibit site-specific absorption in the upper GI tract. In certain embodiments, the gastroretentive dosage forms of the disclosure provide extended release of highly soluble drugs that exhibit site-specific absorption in the upper GI tract, e.g., pyridostigmine. In certain embodiments, the gastroretentive dosage forms of the disclosure include moderately soluble drugs that exhibit site-specific absorption in the GI tract, e.g., carbidopa and levodopa. In certain embodiments, the gastroretentive dosage forms of the disclosure improve bioavailability of moderately and sparingly soluble drugs by extending their gastric residence time such that the drugs are released for extended periods of time, at a controlled rate, into the proximity of their site of absorption (or action), without the dosage form reaching the lower part of the GI tract with the drugs still in the dosage form.

The present disclosure provides extended release, or combined immediate release and extended release, floating gastroretentive drug formulations, with high, medium, or low drug-loading capacity, containing drugs, with any level of solubility, that require targeted drug release in the proximal GI tract for maximum therapeutic benefit. The present disclosure provides rapidly expanding gastroretentive dosage forms comprising a permeable or semipermeable membrane with high elasticity and tensile strength, a multilayered tablet core surrounded by the permeable or semipermeable membrane, wherein the tablet core comprises at least one gas-generating agent and a swellable hydrophilic polymer to provide flotation of the dosage form with a floating lag time of less than about 30 minutes, prevent dose dumping, and ensure the emptying of the dosage form after complete drug recovery. The present disclosure provides self-regulating, oral, osmotic, controlled release, floating gastroretentive dosage forms that are suitable for providing controlled release from about 10 hours to about 24 hours.

The gastroretentive compositions of the disclosure can conveniently release active pharmaceutical agents in an extended release profile, or in a combined immediate and extended release profile, over a prolonged period, without losing bioavailability of the active pharmaceutical agent for the extended release period. Because the gastric retention depends primarily on swelling and floating mechanisms, the swelling behavior was evaluated in terms of gravimetric swelling (water uptake) and volumetric swelling (size increase). FIG. 3 shows swelling kinetics (volumetric) of test formulations. As the entrapment of in situ-generated carbon dioxide produced by the reaction between sodium bicarbonate and/or calcium carbonate with the included acid and/or the SGF, floating lag time was also measured (FIG. 2). In addition, multiple tests of the ability of a tablet to withstand shear forces, offering higher discrimination of the effects of such forces, were also utilized: a custom basket method at 100 rpm (FIG. 4), a rotating bottle method at 15 rpm (FIG. 5), and a Biodis reciprocating cylinder method at 25 dpm (FIGS. 6 and 7).

The test procedures to measure these properties are described in the Examples below. The present disclosure is not to be limited in scope by the specific embodiments described herein. Indeed, various modifications of the disclosure in addition to those described herein will become apparent to those skilled in the art from the foregoing description. Such modifications are intended to fall within the scope of the appended claims.

7. EXAMPLES

The detailed description of the present disclosure is further illustrated by the following Examples, which are illustrative only and are not to be construed as limiting the scope of the disclosure. Variations and equivalents of these Examples will be apparent to those skilled in the art in light of the present disclosure, the drawings, and the claims herein.

Example 1: Preparation of Extended Release Levodopa/Carbidopa Tablets

The present example provides various formulations of extended release levodopa/carbidopa tablets as outlined in Table 1 and Table 2. Eleven different tablets were prepared.

TABLE 1

Formulations of Levodopa/Carbidopa Tablets

| Ingredients | Tablet 1 mg/dose | Tablet 2 mg/dose | Tablet 3 mg/dose | Tablet 4 mg/dose | Tablet 5 mg/dose | Tablet 6 mg/dose |
|---|---|---|---|---|---|---|
| Pull Layer Blend | | | | | | |
| Levodopa | 200.0 | 200.0 | 240.0 | 320.0 | 240.0 | 320.0 |
| Carbidopa | 54.0 | 54.0 | 64.80 | 86.40 | 64.80 | 86.40 |
| POLYOX™ N80 | 200.0 | 200.0 | 193.26 | 141.56 | 190.7 | 190.6 |
| POLYOX™ N303 | 5.00 | 5.0 | 5.0 | 5.014 | 5.0 | 5.0 |
| Hydroxypropyl cellulose | 8.00 | 8.0 | 8.0 | 8.0 | 8.0 | 8.0 |
| Succinic acid | 50.0 | 50.0 | 50.0 | 50.0 | 125.0 | 125.0 |
| α-tocopherol | 0.50 | 0.50 | 0.5 | 0.5 | 0.5 | 0.5 |
| Sodium bicarbonate | 100.0 | 100.0 | 100.0 | 100.0 | 50.0 | 50.0 |
| Calcium carbonate | 25.0 | 25.0 | 25.0 | 25.0 | 75.0 | 75.0 |
| PARTECK® M200 | 44.00 | 44.0 | — | — | 51.50 | 0.0 |
| Cab-O-Sil® | 3.5 | 3.5 | 3.5 | 3.5 | 3.5 | 3.5 |
| Magnesium stearate | 10.0 | 10.0 | 10.0 | 10.0 | 10.0 | 10.0 |
| Push Layer Blend | | | | | | |
| POLYOX™ N60 | 220.0 | 220.0 | 220.0 | 220.0 | 220.0 | 220.0 |
| Sodium chloride | 25.0 | 25.0 | 25.0 | 25.0 | 25.0 | 25.0 |
| Red pigment blend (PB1595) | 2.0 | 2.0 | 2.0 | 2.0 | — | — |
| Oxide Pigment Black (PB-177003) | — | — | — | — | 4.0 | 4.0 |
| Magnesium stearate | 3.0 | 3.0 | 3.0 | 3.0 | 3.0 | 3.0 |
| Tablet Core Weight | 950.0 | 950.0 | 950.0 | 1000.0 | 1076.0 | 1126.0 |
| Tablet Core with Coating System | | | | | | |
| OPADRY® II clear | 40.0 | 40.0 | 40.0 | 40.0 | 40.0 | 40.0 |
| EUDRAGIT® RL PO | 111.15 | 148.2 | 111.2 | 111.2 | 111.2 | 111.2 |
| Triethyl citrate | 16.65 | 22.50 | 16.65 | 16.65 | 16.65 | 16.65 |
| Talc | 22.20 | 29.60 | 22.20 | 22.20 | 22.20 | 22.20 |
| OPADRY® II, Pink | 15.0 | 15.0 | 15.0 | 15.0 | — | 15.0 |
| OPADRY® II, Green | | | | | — | — |
| OPADRY® II, Blue | | | | | 15.0 | — |
| Opadry EZ Clear | — | 10.0 | 10.0 | 10.0 | 10.0 | 10.0 |
| Total Weight | 1155.0 | 1205.0 | 1165.0 | 1215.0 | 1291.0 | 1341.0 |

TABLE 2

Formulations of Levodopa/Carbidopa Tablets

| Ingredients | Tablet 7 mg/dose | Tablet 8 mg/dose | Tablet 9 mg/dose | Tablet 10 mg/dose | Tablet 11 mg/dose | Tablet 12 mg/dose |
|---|---|---|---|---|---|---|
| Pull Layer Blend | | | | | | |
| Levodopa | 240.0 | 320.0 | 240.0 | 320.0 | 320.0 | 315.0 |
| Carbidopa | 64.80 | 86.40 | 64.80 | 86.40 | 86.40 | 85.0 |
| POLYOX™ N80 | 190.7 | 190.6 | 190.7 | 190.6 | 190.6 | 148.0 |
| POLYOX™ N303 | 5.0 | 5.0 | 5.0 | 5.0 | 5.0 | 5.0 |
| Hydroxypropyl cellulose | 8.0 | 8.0 | 8.0 | 8.0 | 8.0 | 8.0 |
| Succinic acid | 75.0 | 75.0 | 100.0 | 100.0 | 125.0 | 50.0 |
| Sodium Chloride | — | — | — | — | 50 | — |
| α-tocopherol | 0.50 | 0.50 | 0.50 | 0.50 | 0.50 | 0.50 |
| Sodium bicarbonate | 50.0 | 50.0 | 50.0 | 50.0 | 50.0 | 100.0 |
| Calcium carbonate | 75.0 | 75.0 | 75.0 | 75.0 | 75.0 | 25.0 |
| PARTECK™ M200 | — | — | — | — | — | — |
| Cab-O-Sil | 3.5 | 3.5 | 3.5 | 3.5 | 3.5 | 3.5 |
| Magnesium stearate | 10.0 | 10.0 | 10.0 | 10.0 | 10.0 | 10.0 |
| Push Layer Blend | | | | | | |
| POLYOX™ N60 | 220.0 | 220.0 | 220.0 | 220.0 | 220.0 | 220.0 |
| Sodium chloride | 25.0 | 25.0 | 25.0 | 25.0 | 25.0 | 25.0 |
| Oxide Pigment Black (PB-177003) | 4.0 | 4.0 | 4.0 | 4.0 | 4.0 | — |
| Iron oxide (Red Blend) | — | — | — | — | — | 2.0 |
| Magnesium stearate | 3.0 | 3.0 | 3.0 | 3.0 | 3.0 | 3.0 |
| Tablet Core Weight | 974.5 | 1076.0 | 999.5 | 1101.0 | 1176.0 | 1000.0 |
| Tablet Core with Coating System | | | | | | |
| Levodopa/carbidopa tablet core | 974.5 | 1076.0 | 999.5 | 1101.0 | 1176.0 | 1000.0 |
| OPADRY® II clear | 40.0 | 40.0 | 40.0 | 40.0 | 40.0 | 40.0 |
| EUDRAGIT®RL PO | 111.2 | 111.2 | 111.2 | 111.2 | 111.2 | 111.15 |
| Triethyl citrate | 16.65 | 16.65 | 16.65 | 16.65 | 16.65 | 16.65 |
| Talc | 22.20 | 22.20 | 22.20 | 22.20 | 22.20 | 22.20 |
| OPADRY® II, Pink | — | 15.0 | — | 15.0 | 15.0 | 15.0 |
| OPADRY® II, Blue | 15.0 | | 15.0 | | — | — |
| Opadry EZ Clear | 10.0 | 10.0 | 10.0 | 10.0 | 10.0 | — |
| IR Drug Layer | | | | | | |
| Carbidopa | — | — | — | — | — | 17.55 |
| Levodopa | — | — | — | — | — | 65.0 |
| HPC | — | — | — | — | — | 15.0 |
| α-tocopherol | — | — | — | — | — | 0.52 |
| Succinic acid | — | — | — | — | — | 3.25 |
| Total Weight | 1189.55 | 1291.0 | 1214.5 | 1316.0 | 1391.0 | 1306.32 |

Tablets 1-4 and Tablet 12 contain 100 mg of sodium bicarbonate and 25 mg of calcium carbonate, and Tablets 5-11 contain 50 mg of sodium bicarbonate and 75 mg of calcium carbonate. Further, Tablets 1-4 and Tablet 12 contain 50 mg of succinic acid, Tablets 5, 6, and 11 contain 125 mg of succinic acid, Tablets 7 and 8 contain 75 mg of succinic acid, and Tablets 9 and 10 contain 100 mg of succinic acid. The tablets were made according to the following general procedure.

Manufacturing Procedure:
  A. Pull Layer Blend:
    Levodopa, carbidopa, POLYOX™ N80, POLYOX™ N303, succinic acid, α-tocopherol, and hydroxypropyl cellulose were wet granulated into CD/LD granulates, the resulting granules were dried, milled, and blended with sodium bicarbonate, calcium carbonate, PARTECK® M200, Cab-O-Sil®, and magnesium stearate to obtain a uniform pull layer blend.
  B. Push Layer Blend:
    POLYOX™ N60, sodium chloride, red pigment blend, and magnesium stearate were blended to obtain a uniform push layer blend.
  C. Bilayered Tablet Core:
    The pull layer blend from step A and push layer blend from step B were pressed horizontally, using a suitable tablet press, into a bilayered tablet core.
  D. Coating System:
    Bilayered tablet cores from step C were coated, using a perforated pan coater, with a seal coat comprising OPADRY® II, clear; and a functional coat comprising triethyl citrate, EUDRAGIT® RL PO, and talc.
  E. Laser Hole Drilling:
    A laser hole in fluid communication with the pull layer was drilled into the coating system from step D (excluding the cosmetic coat and the final coat, i.e., before those coats were applied).
  F. IR Drug Layer:
    Laser hole-drilled bilayered tablets from step E were coated, using a perforated pan coater, with an IR drug layer comprising carbidopa, levodopa, hydroxypropyl cellulose (HPC), α-tocopherol, and succinic acid.
  G. Over Coat and Final Coat:
    Laser hole-drilled tablets from step E were further coated with a cosmetic coat comprising OPADRY® II, Pink/Green/Blue; and a final coat comprising OPADRY® EZ, Clear. Tablets with an IR drug layer from step F were further coated with a seal coat comprising OPADRY® II clear, cosmetic coat comprising OPADRY® II, Pink/Green/Blue; and a final coat comprising OPADRY® EZ clear. All coatings were performed using a perforated pan coater.

Example 2: Measurement of Volumetric Swelling

The tablet volume was determined to calculate the volumetric expansion. To calculate the volume, the swollen tablet was placed in a graduated measuring cylinder filled with fixed volume of dissolution medium, and the rise in dissolution medium level was noted over a 14-hour period. The percent volumetric expansion was calculated using the following equation:

$$\text{Volumetric Gain (\%)} = \frac{V_s - V_d}{V_d} \times 100$$

$V_s$ is the volume of swollen tablet (at specific time point), and $V_d$ is the volume of dry tablet (initial).

FIG. 3 compares volumetric swelling of Tablet 1 and Tablet 2 in about 200 ml of about pH 4.5 acetate buffer, using rotating bottle dissolution method, at 15 rpm and temperature of 37° C. Tablet 2 contained a higher coating weight gain (about 15 wt % of the uncoated tablet core) of functional coat, than Tablet 1 (about 12 wt % of the uncoated tablet core). FIG. 3 shows tablet volume gains of Tablet 1 and Tablet 2 over a 20-hour period. The figure demonstrates that the tablets exhibited a volume gain of about 100% in less than 1 hour, e.g., about 45 minutes.

FIG. 9 compares volumetric swelling of Tablet 5 (240 mg levodopa) and Tablet 6 (320 mg levodopa) in a light meal medium comprising about 200 ml of an aqueous medium comprising sodium chloride, calcium chloride, phosphate salts, citric acid, and sugar, using rotating bottle dissolution method, at 15 rpm and temperature of 37° C. FIG. 9 shows tablet volume gains of Tablet 5 and Tablet 6 over an 8-hour period. The figure demonstrates that the tablets exhibited a volume gain of about 100% in about 3 hours.

Example 3: Measurement of Floating Lag Time

The time required for the tablet to float in a gastric medium is an important measure of the gastric retention, as a rapid progression to floating reduces the chance of accidental emptying (escape) of the dosage form from the stomach. The final coated tablets from Example 1 (Tablets 1 and 2) were placed in about 250 mL of pH 4.5 acetate buffer in a USP dissolution apparatus III—Biodis at 25 dpm. The tablets were carefully observed until they began to float on the surface of the medium. The elapsed time was recorded and reported as floating lag time.

FIG. 2 compares floating lag times of Tablet 1 and Tablet 2 in about 250 ml of pH 4.5 acetate buffer, using USP dissolution apparatus III—Biodis reciprocating cylinder, at about 25 dpm and about 37° C. Tablet 2 contained a higher coating weight gain (about 15 wt % of the uncoated tablet core) in its functional coat, as compared with Tablet 1 (about 12 wt % of the uncoated tablet core). FIG. 2 demonstrates that the tablets exhibited a floating lag time of about 15 minutes or less.

Example 4: Measurement of Dissolution Profile

Dissolution of drug from the dosage form is an important measure to achieve controlled and extended delivery of the drug. Dissolution studies were performed using different conditions to assess the effect of different physiological and hydrodynamic conditions with regards to pH, buffer, and shear forces. The United States Pharmacopeia (USP) has established a standardized dissolution apparatus to measure the in vitro performance of a drug product for development and quality control purposes. These standard procedures use in vitro solubility as a surrogate for in vivo absorption. Because of the floating nature of the tablet, USP dissolution apparatus I, which uses a basket as sample holder, was used to evaluate the release of drug from these tablets as a function of time. In addition, to simulate the effect of shear conditions in fasting and fed states, dissolution studies were also performed using rotating bottle dissolution method, and USP dissolution apparatus III—Biodis reciprocating cylinder method. Different dissolution methods used for this purpose are described below.

USP Dissolution Apparatus I (Custom Basket):
A Distek Automatic Dissolution Apparatus equipped with custom size basket was used. The dissolution test was performed in about 900 mL of pH 4.5 acetate buffer to simulate fed conditions. A rotation speed of about 100 rpm was used. In the case of a combination product such as carbidopa/levodopa, the drug release was measured using high performance liquid chromatography (HPLC). Drug sample (5 ml) was withdrawn at specified time intervals of 2, 4, 6, 8, 10, 12, and 14 hours, and the drug content was measured by HPLC. FIG. 4 shows dissolution profiles of Tablet 1 and Tablet 2 using USP dissolution apparatus I—custom basket in about 900 ml of pH 4.5 acetate buffer, at about 100 rpm. FIG. 4 demonstrates at least about 10% dissolution of levodopa, in a dissolution medium simulating fed state of an individual, in 2 hours.

Rotating Bottle Method:

A rotating bottle method was used to simulate high shear conditions in stomach. Tablet 1 and Tablet 2 were placed in about 200 ml of dissolution medium in a glass bottle containing about 10 g of glass beads (3 mm). The bottle was secured in the rotating arm of an apparatus placed inside a constant temperature water bath maintained at about 37° C. The bottle was rotated at speeds of about 15 rpm or about 30 rpm to simulate the effect of different shear conditions in the stomach in fed state. Drug sample (about 5-10 ml) was withdrawn at specified time intervals of 2, 4, 6, 8, and 14 hours, and the drug content released was measured using HPLC. FIG. 5 shows dissolution profiles of Tablet 1 and Tablet 2 using the rotating bottle method, in about 200 ml of pH 4.5 acetate buffer, at about 15 rpm. FIG. 5 demonstrates at least about 10% dissolution of levodopa, in a dissolution medium simulating fed state of an individual, in about 2 hours.

USP III (Biodis Reciprocating Cylinder Method):

A reciprocating cylinder method, associating the hydrodynamics of a rotating bottle method with the facility for exposing the dosage form to different dissolution media and agitation speeds, was used to simulate high shear conditions in stomach. The dosage unit was inserted into an internal cylinder, consisting of a glass tube closed at both ends with plastic caps containing a screen. The internal cylinder was connected to a metallic rod that undertook immersion and emersion movements (reciprocating action) within the dissolution vessel/external cylinder. An anti-evaporation system was deployed over the vessels in order to avoid alteration in the volume of the dissolution medium during the assay. FIG. 6 compares dissolution profiles of levodopa from Tablet 1 and Tablet 2, in about in 250 ml of pH 4.5 acetate buffer, using USP III—Biodis reciprocating cylinder, at about 5 dpm and about 37° C. The drug samples were withdrawn at specified time intervals of 2, 4, 6, 8, and 14 hours, and drug concentration was measured using HPLC. Tablet 2 contained a higher coating weight gain (about 15 wt % of the uncoated tablet core) in its functional coat than Tablet 1 (about 12 wt % of the uncoated tablet core). FIG. 6 demonstrates at least about 15% dissolution of levodopa, in a dissolution medium simulating a fed state of an individual, in about 120 minutes.

FIG. 7 shows cyclic dissolution profiles of levodopa from Tablet 1 and Tablet 2 using USP dissolution apparatus III—Biodis, simulating gastric conditions during a 12-hour period, e.g., fed state, fasted state, followed by a subsequent fed state (each state for four hours). FIG. 7 shows cyclic dissolution profiles with an initial dissolution in 250 ml pH 4.5 acetate buffer, followed by dissolution in 250 ml 0.01 N HCl, and final dissolution in 250 ml pH 4.5 acetate buffer (each dissolution period of about 4 hours). Tablet 2 contained a higher coating weight gain (about 15 wt % of the uncoated tablet core) in its functional coat than Tablet 1 (about 12 wt % of the uncoated tablet core).

Example 5: Measurement of Dissolution Profile in a Dissolution Medium Comprising 0.001 N HCL and 10 mM NaCl Dissolution of drug from the dosage form is an important measure to achieve controlled and extended delivery of the drug. Dissolution studies were performed using a dissolution medium comprising 0.001 N HCL with 10 mM NaCl. FIG. 8 compares dissolution profiles of levodopa from Tablet 5 (240 mg levodopa) and Tablet 6 (320 mg levodopa), in 900 ml of a dissolution medium comprising 10 mM NaCl in 0.001 N HCl, using USP I—Custom basket, at about 100 rpm and about 37° C. Samples for drug measurement were withdrawn at specified time intervals of 1, 2, 4, 6, 8, 10, 12, 16, and 20 hours and drug concentrations were measured using HPLC. FIG. 8 demonstrates about 40% dissolution of levodopa in about 120 minutes.

Example 6: Oral Bioavailability of Carbidopa and Levodopa for Tablet 1 and Tablet 2

A single dose pharmacokinetic (PK) study was conducted in healthy volunteers under fed conditions to evaluate the PK performance of self-regulating, osmotic, floating gastroretentive dosage forms of the disclosure using Tablet 1 and Tablet 2. An open-label, single dose, cross-over comparative bioavailability study was conducted in 24 normal, healthy, adult, human subjects under high-fat, high-calorie breakfast condition.

FIG. 10 provides mean (n=24) plasma concentration curves for levodopa. An extended release providing therapeutic concentration, from about 300 ng/ml to about 500 ng/ml, of levodopa for a period of about 9 hours was observed in all 24 volunteers dosed with Tablets 1 and 2. Pharmacokinetic parameters for carbidopa and levodopa are summarized in Tables 3 and 4, respectively.

TABLE 3

Pharmacokinetics Results of Carbidopa

| Pharmacokinetic parameters (units) | Mean ± SD (CV %) (N = 24) | |
|---|---|---|
| | Tablet 1 | Tablet 2 |
| $C_{max}$ (ng/mL) | 43.38 ± 14.89 (34.33) | 37.76 ± 17.73 (46.95) |
| $AUC_{0-t}$ (ng · hr/mL) | 340.70 ± 87.83 (25.78) | 300.21 ± 119.25 (39.72) |
| $AUC_{0-inf}$ (ng · hr/mL) | 373.33 ± 85.69 (22.95) | 421.03 ± 426.59 (101.32) |
| $T_{max}$ (hr)* | 5.00 (4.00-14.00) | 11.53 (5.00-15.00) |
| $K_{el}$ (hr − 1) | 0.21 ± 0.09 (42.17) | 0.20 ± 0.10 (49.58) |
| $t_{1/2}$ (hr) | 4.38 ±3.08 (70.33) | 10.47 ± 27.59 (263.60) |
| AUC Extrapolated (%) | 8.94 ± 9.22 (103.19) | 13.90 ± 21.40 (154.01) |

TABLE 4

Pharmacokinetics Results of Levodopa

| Pharmacokinetic parameters (units) | Mean ± SD (CV %) (N = 24) | |
|---|---|---|
| | Tablet 1 | Tablet 2 |
| $C_{max}$ (ng/mL) | 730.36 ± 202.07 (27.67) | 618.20 ± 201.33 (32.57) |
| $AUC_{0-t}$ (ng · hr/mL) | 5164.54 ± 957.55 (18.54) | 4505.34 ± 1481.74 (32.89) |
| AUC0-inf (ng · hr/mL) | 5372.20 ± 978.34 (18.21) | 4987.96 ± 2415.12 (48.42) |
| $T_{max}$ (hr)* | 8.00 (4.00-13.00) | 9.00 (5.00-14.00) |
| $K_{el}$ (hr − 1) | 0.31 ± 0.13 (41.49) | 0.29 ± 0.11 (36.09) |
| $t_{1/2}$ (hr) | 2.87 ± 1.87 (64.98) | 3.65 ± 5.57 (152.39) |
| AUC Extrapolated (%) | 3.54 ± 7.64 (215.87) | 4.81 ± 13.79 (286.68) |

The data from this study (Tables 3 and 4/FIG. 10) demonstrate that self-regulating, osmotic, floating gastroretentive compositions of the disclosure (Tablets 1 and 2) provide extended release of the drug for a period of about 12 hours and are suitable for once- or twice-daily administration. Tablets 1 and 2, based on a dosing regimen of twice a day and an extended release profile of over 12 hours, will have key advantages over other nongastroretentive formulations to reduce the percentage of "off" time from baseline, as well as increase the percentage of "on" time without troublesome dyskinesia during waking.

Example 7: Oral Bioavailability of Carbidopa and Levodopa for Tablets 5 and 6

A single-dose pharmacokinetic (PK) study was conducted in healthy volunteers under the fed condition to evaluate the PK performance of oral, osmotic, controlled release floating gastroretentive dosage forms of the disclosure using Tablets 5 and 6. An open-label, nonrandomized, single-dose, two-treatment, one-way crossover, comparative bioavailability study was conducted in 24 normal, healthy, adult human subjects under high-fat, high-calorie breakfast conditions.
PK parameters for levodopa are summarized in Table 5.

TABLE 5

Pharmacokinetics Results of Levodopa

| Pharmacokinetic parameters (units) | Mean ± SD (CV %) (N = 24) | |
|---|---|---|
| | Tablet 5 (240 mg) | Tablet 6 (320 mg) |
| $C_{max}$ (ng/mL) | 1566.50 ± 350.75 (22.39) | 2068.05 ± 500.17 (24.19) |
| $AUC_{0-t}$ (ng · hr/mL) | 8549.60 ± 981.76 (11.48) | 11628.01 ± 2430.91 (20.91) |
| AUC0-inf (ng · hr/mL) | 8612.11 ± 981.40 (11.40) | 11702.07 ± 2457.26 (21.00) |
| $T_{max}$ (hr)* | 4.41 ± 1.32 (29.91) | 4.78 ± 1.53 (39.96) |
| $K_{el}$ (hr − 1) | 0.28 ± 0.07 (25.33) | 0.28 ± 0.07 (25.15) |
| $t_{1/2}$ (hr) | 2.63 ± 0.62 (23.68) | 2.60 ± 0.57 (21.97) |
| AUC Extrapolated (%) | 0.73 ± 0.52 (70.78) | 0.62 ± 0.38 (60.85) |

The data from this study (Table 5/FIG. 11) demonstrates that oral, osmotic, controlled release, floating gastroretentive compositions of the disclosure (Tablets 5 and 6) provide about 30% more bioavailability compared to Tablets 1 and 2. FIG. 11 provides mean (n=24) plasma concentration curves for levodopa. FIG. 11 demonstrates that Tablets 5 and 6 provide extended release of at least about 400 ng/ml of levodopa for a period of about 7 hours and about 10 hours, respectively. Table 5 further demonstrates dose proportionality between the 240 mg and 320 mg tablet strengths.

Example 8: MRI Study Showing Self-regulation of Gastroretentive Dosage Forms

An open-label, single-treatment, single-period, magnetic resonance imaging (MRI) study of Tablet 5 (CD/LD—60 mg/240 mg extended release tablet containing black iron oxide as MRI-contrasting agent) was conducted using Siemens Magnetom Symphony 1.5 Tesla system. The study was conducted in healthy adult subjects under fed conditions. Abdominal MRI scans of stomach and intestine of the subjects were performed to see the presence of the tablet in the subjects at 8, 10, 12, 16, and 24 hours (±30 minutes) post-dose period. The tablets were visible as black spots/holes in the stomach due to the presence of black iron oxide. FIG. 12 shows post-dose MRI scans of stomach and intestine of one of the subject consuming the dosage form. FIG. 12 shows that the black spot spreads in the entire stomach at 24 hours, indicating the tablet falls apart at some time between 16 hours and 24 hours post-dose.

Example 9: Preparation of Extended Release Liothyronine Tablets, 50 mcg

The present example provides formulation of extended release liothyronine tablets as outlined in Table 6.

TABLE 6

Formulation of Liothyronine Tablets

| Ingredients | Tablet 13 (mg/dose) | Tablet 14 (mg/dose) |
|---|---|---|
| Pull Layer Blend | | |
| Liothyronine sodium* | 0.052 | 0.052 |
| Calcium sulfate | 239.45 | 239.45 |
| Hydroxypropyl cellulose | 5.0 | 5.0 |
| α-tocopherol, | 0.5 | 0.5 |
| POLYOX ™ N80 | 261.5 | 261.5 |
| POLYOX ™ N303 | 5.0 | 5.0 |

TABLE 6-continued

Formulation of Liothyronine Tablets

| Ingredients | Tablet 13 (mg/dose) | Tablet 14 (mg/dose) |
|---|---|---|
| Sodium bicarbonate | 100.0 | 100.0 |
| Calcium carbonate | 25.0 | 25.0 |
| Succinic acid | 50.0 | 50.0 |
| Cab-O-Sil | 3.5 | 3.5 |
| Magnesium stearate | 10.0 | 10.0 |
| Push Layer Blend | | |
| POLYOX ™ N60 | 220.0 | 220.0 |
| Sodium chloride | 25.0 | 25.0 |
| Red pigment blend (PB1595) | 2.0 | 2.0 |
| Magnesium stearate | 3.0 | 3.0 |
| Tablet Core Weight | 950.0 | 950.0 |
| Tablet Core with Coating System | | |
| OPADRY ® II, clear | 40.0 | 40.0 |
| EUDRAGIT ® RL PO | 111.15 | 148.20 |
| Triethyl citrate | 16.65 | 22.50 |
| Talc | 22.20 | 29.60 |
| OPADRY ® II, Pink | 15.0 | 15.0 |
| Opadry EZ, Clear | 10.0 | 10.0 |
| Tablet Weight | 1165.0 | 1215.0 |

*0.052 mg of liothyronine sodium is equivalent to 0.050 mg of liothyronine

Tablet 13 contains about 15% coating weight gain of the functional coat, and Tablet 14 contains about 20% coating weight gain of the functional coat. The tablets are made according to the following manufacturing procedure.

Manufacturing Procedure:

A. Pull layer blend:

Liothyronine sodium, calcium sulfate, hydroxypropyl cellulose, and α-tocopherol are wet granulated and blended with sodium bicarbonate, calcium carbonate, POLYOX® N80, POLYOX™ N303, succinic acid, Cab-O-Sil®, and magnesium stearate to obtain a uniform pull layer blend.

B. Push Layer Blend:

POLYOX™ N60, sodium chloride, red pigment, and magnesium stearate are blended into a uniform push layer blend.

C. Bilayered Tablet Core:

The two layers from Steps A and B are pressed horizontally to form a bilayered tablet core.

D. Coating System:

Bilayered tablets from Step C are coated with a seal coat comprising OPADRY® II, clear; a functional coat comprising triethyl citrate and EUDRAGIT® RL PO, and talc; a cosmetic coat comprising OPADRY® II, Pink; and a final coat comprising OPADRY® EZ, clear.

E. Laser Hole Drilling:

A laser hole in fluid communication with the pull layer is drilled into the coating system (before application of the cosmetic coat and the final coat described in Step D, above).

Example 10: Extended Release Metaxalone Tablets, 400 mg

The present example provides formulation of extended release metaxalone tablets as outlined in Table 7.

TABLE 7

| Ingredients | Tablet 15 (mg/dose) | Tablet 16 (mg/dose) |
|---|---|---|
| Pull layer blend | | |
| Metaxalone | 400.0 | 400.0 |
| POLYOX ™ N 80 | 148.0 | 148.0 |
| POLYOX ™ N 303 | 3.0 | 3.0 |
| Hydroxypropyl cellulose | 8.0 | 8.0 |
| Succinic acid | 50.0 | 50.0 |
| Sodium chloride | — | — |
| α-tocopherol, | 0.50 | 0.50 |
| Sodium bicarbonate | 100.0 | 100.0 |
| Calcium carbonate | 25.0 | 25.0 |
| Parteck M200 | — | — |
| Cab-O-Sil | 3.5 | 3.5 |
| Magnesium stearate | 10.0 | 10.0 |
| Push layer blend | | |
| POLYOX ™ N 60 | 220.0 | 220.0 |
| Sodium chloride | 25.0 | 25.0 |
| Oxide Pigment Black (PB-177003) | 2.0 | 2.0 |
| Magnesium stearate | 3.0 | 3.0 |
| Tablet Core Weight | 1000.0 | |
| Tablet Core with Coating System | | |
| OPADRY ® II clear | 40.0 | |
| EUDRAGIT ® RL PO | 111.2 | 148.20 |
| Triethyl citrate | 16.65 | 22.50 |
| Talc | 22.20 | 29.60 |
| OPADRY ® II, Pink | 15.0 | 15.0 |
| Opadry EZ Clear | 10.0 | 10.0 |
| Total | 1215.0 | 1245.0 |

Tablet 15 contains about 15% coating weight gain of the functional coat, and Tablet 16 contains about 18% coating weight gain of the functional coat. The tablets are made according to the following manufacturing procedure.

Manufacturing Procedure:

A. Pull Layer Blend:

Metaxalone, POLYOX™ N 80, POLYOX™ N 303, succinic acid, α-tocopherol, and hydroxypropyl cellulose are wet granulated and blended with sodium bicarbonate, calcium carbonate, Parteck® M200, Cab-O-Sil®, and magnesium stearate to obtain a uniform pull layer final blend.

B. Push Layer Blend:

POLYOX™ N 60, sodium chloride, red pigment, and magnesium stearate are blended into a uniform blend.

C. Bilayered Tablet Core:

The pull layer blend from Step A and push layer blend from Step B are pressed horizontally, using a suitable tablet press, into a bilayered tablet core.

D. Coating System:

Bilayered tablet cores from Step C are coated with a seal coat comprising OPADRY® II, Clear, a functional coat comprising EUDRAGIT® RL PO, triethyl citrate, and talc, a cosmetic coat comprising OPADRY® II, Pink, and a final coat comprising OPADRY EZ clear.

E. Laser Hole Drilling:

A laser hole in fluid communication with the pull layer is drilled into the coating system (before application of the cosmetic coat and the final coat described in Step D, above).

Example 11: Extended Release Tetracycline/Amoxicillin/Ampicillin/Clindamycin Tablets The present example provides formulation of extended release tetracycline/amoxicillin/ampicillin/clindamycin tablets as outlined for Tablets 17-20 in Table 8.

TABLE 8

| Ingredients | mg/dose | | | |
|---|---|---|---|---|
| Pull layer blend | 17 | 18 | 19 | 20 |
| Tetracycline Hydrochloride | 500.0 | 0.0 | 0.0 | 0.0 |
| Clindamycin | 0.0 | 300 | 0.0 | 0.0 |
| Ampicillin | 0.0 | 0.0 | 500 | 0.0 |
| Amoxicillin | 0.0 | 0.0 | 0.0 | 500 |
| Hydroxypropyl cellulose | 8.0 | 8.0 | 8.0 | 8.0 |
| α-tocopherol, | 0.5 | 0.5 | 0.5 | 0.5 |
| POLYOX™ N750 | 148.0 | 148.0 | 148.0 | 148.0 |
| POLYOX™ N60 | 3.0 | 3.0 | 3.0 | 3.0 |
| Sodium bicarbonate | 50.0 | 50.0 | 50.0 | 50.0 |
| Calcium carbonate | 75.0 | 75.0 | 75.0 | 75.0 |
| Succinic acid | 125.0 | 125.0 | 125.0 | 125.0 |
| Cab-O-Sil® | 3.5 | 3.5 | 3.5 | 3.5 |
| Magnesium stearate | 10.0 | 10.0 | 10.0 | 10.0 |
| Push Layer Blend | 0.0 | 0.0 | 0.0 | 0.0 |
| POLYOX™ N60 | 220.0 | 220.0 | 220.0 | 220.0 |
| Sodium chloride | 25.0 | 25.0 | 25.0 | 25.0 |
| Red pigment blend (PB1595) | 2.0 | 2.0 | 2.0 | 2.0 |
| Magnesium stearate | 3.0 | 3.0 | 3.0 | 3.0 |
| Tablet Core Weight | 1173 | 973 | 1173 | 1173 |
| OPADRY® II, clear | 40.0 | 40.0 | 40.0 | 40.0 |
| EUDRAGIT® RL PO | 111.15 | 111.15 | 111.15 | 111.15 |
| Triethyl citrate | 16.65 | 16.65 | 16.65 | 16.65 |
| Talc | 22.20 | 22.20 | 22.20 | 22.20 |
| OPADRY® II, Pink | 15.0 | 15.0 | 15.0 | 15.0 |
| Opadry EZ, Clear | 10.0 | 10.0 | 10.0 | 10.0 |
| Tablet Weight | 1388 | 1188 | 1388 | 1388 |

Manufacturing Procedure:

A. Pull Layer Blend:
Tetracycline hydrochloride/clindamycin/ampicillin/amoxicillin, POLYOX™ N 750, POLYOX™ N 60, succinic acid, α-tocopherol, and hydroxypropyl cellulose are dry granulated using roller compaction; the resulting granules are milled, and blended with sodium bicarbonate, calcium carbonate, Parteck® M200, Cab-O-Sil®, and magnesium stearate to obtain a uniform pull layer final blend.

B. Push Layer Blend:
POLYOX™ N 60, sodium chloride, red pigment, and magnesium stearate are blended into a uniform blend.

C. Bilayered Tablet Core:
The pull layer blend from Step A and push layer blend from Step B are pressed horizontally, using a suitable tablet press, into a bilayered tablet core.

D. Coating System:
Bilayered tablet cores from Step C are coated with a seal coat comprising OPADRY® II, Clear, a functional coat comprising EUDRAGIT® RL PO, triethyl citrate, and talc, a cosmetic coat comprising OPADRY® II, Pink, and a final coat comprising OPADRY EZ clear.

E. Laser Hole Drilling:
A laser hole in fluid communication with the pull layer is drilled into the coating system (before application of the cosmetic coat and the final coat described in Step D, above).

Example 12: Extended Release Domperidone/Odansetron/Ranitidine Hydrochloride/Metformin Hydrochloride Tablets The present example provides formulation of extended release domperidone/odansetron/ranitidine hydrochloride/metformin hydrochloride tablets as outlined for Tablets 21-24 in Table 9.

TABLE 9

| Ingredients | mg/dose | | | |
|---|---|---|---|---|
| Pull Layer Blend | 21 | 22 | 23 | 24 |
| Domperidone | 10.0 | 0.0 | 0.0 | 0.0 |
| Odansetron | 0.0 | 8.0 | 0.0 | 0.0 |
| Ranitidine Hydrochloride | 0.0 | 0.0 | 300 | 0.0 |
| Metformin Hydrochloride | 0.0 | 0.0 | 0.0 | 500 |
| Hydroxypropyl cellulose | 8.0 | 8.0 | 8.0 | 8.0 |
| α-tocopherol, | 0.5 | 0.5 | 0.5 | 0.5 |
| POLYOX™ N80 | 148.0 | 148.0 | 148.0 | 148.0 |
| POLYOX™ N303 | 3.0 | 3.0 | 3.0 | 3.0 |
| Sodium bicarbonate | 50.0 | 50.0 | 50.0 | 50.0 |
| Calcium carbonate | 75.0 | 75.0 | 75.0 | 75.0 |
| Succinic acid | 125.0 | 125.0 | 125.0 | 125.0 |
| Cab-O-Sil® | 3.5 | 3.5 | 3.5 | 3.5 |
| Magnesium stearate | 10.0 | 10.0 | 10.0 | 10.0 |
| Push Layer Blend | 0.0 | 0.0 | 0.0 | 0.0 |
| POLYOX™ N60 | 220.0 | 220.0 | 220.0 | 220.0 |
| Sodium chloride | 25.0 | 25.0 | 25.0 | 25.0 |
| Red pigment blend (PB1595) | 2.0 | 2.0 | 2.0 | 2.0 |
| Magnesium stearate | 3.0 | 3.0 | 3.0 | 3.0 |
| Tablet Core Weight | 683 | 681 | 973 | 1173 |
| OPADRY® II, clear | 40.0 | 40.0 | 40.0 | 40.0 |
| EUDRAGIT® RL PO | 111.15 | 111.15 | 111.15 | 111.15 |
| Triethyl citrate | 16.65 | 16.65 | 16.65 | 16.65 |
| Talc | 22.20 | 22.20 | 22.20 | 22.20 |
| OPADRY® II, Pink | 15.0 | 15.0 | 15.0 | 15.0 |
| Opadry EZ, Clear | 10.0 | 10.0 | 10.0 | 10.0 |
| Tablet Weight | 898.0 | 896.0 | 1188.0 | 1388.0 |

Manufacturing Procedure:

A. Pull Layer Blend:
Domperidone/odansetron/ranitidine hydrochloride/metformin hydrochloride, POLYOX™ N 80, POLYOX™ N 303, succinic acid, α-tocopherol, and hydroxypropyl cellulose are wet granulated; the resulting granules are dried, milled, and blended with sodium bicarbonate, calcium carbonate, Parteck® M200, Cab-O-Sil®, and magnesium stearate to obtain a uniform pull layer final blend.

B. Push Layer Blend:
POLYOX™ N 60, sodium chloride, red pigment, and magnesium stearate are blended into a uniform blend.

C. Bilayered Tablet Core:
The pull layer blend from Step A and push layer blend from Step B are pressed horizontally, using a suitable tablet press, into a bilayered tablet core.

D. Coating System:
Bilayered tablet cores from Step C are coated with a seal coat comprising OPADRY® II, Clear, a functional coat comprising EUDRAGIT® RL PO, triethyl citrate, and talc, a cosmetic coat comprising OPADRY® II, Pink, and a final coat comprising OPADRY EZ clear.

E. Laser Hole Drilling:
A laser hole in fluid communication with the pull layer is drilled into the coating system (before application of the cosmetic coat and the final coat described in Step D, above).

Example 13: Extended Release Metronidazole Tablets

The present example provides formulation of extended release metronidazole tablets as outlined in Table 10.

TABLE 10

Formulation of Metronidazole Tablets

| Ingredients | Tablet 25 mg/dose |
|---|---|
| Pull Layer Blend | |
| Metronidazole | 375 |
| Hydroxypropyl cellulose | 8.0 |
| Alpha tocopherol (Vit-E) | 0.5 |
| POLYOX ™ N80 | 148.0 |
| POLYOX ™ N303 | 3.0 |
| Sodium bicarbonate | 50.0 |
| Calcium carbonate | 75.0 |
| Succinic acid | 125.0 |
| Cab-O-Sil ® | 3.5 |
| Magnesium stearate | 10.0 |
| Push Layer Blend | |
| POLYOX ™ N60 | 220.0 |
| Sodium chloride | 25.0 |
| Red pigment blend (PB1595) | 2.0 |
| Magnesium stearate | 3.0 |
| Tablet Core Weight | 1048.0 |
| OPADRY ® II, clear | 40.0 |
| EUDRAGIT ® RL PO | 111.15 |
| Triethyl citrate | 16.65 |
| Talc | 22.20 |
| OPADRY ® II, Pink | 15.0 |
| Opadry EZ, Clear | 10.0 |
| Tablet Weight | 1263.0 |

Manufacturing Procedure:

A. Pull Layer Blend:

Metronidazole, POLYOX™ N 80, POLYOX™ N 303, succinic acid, α-tocopherol, and hydroxypropyl cellulose are granulated by hot-melt extrusion or wet granulation; the resulting granules are dried, milled, and blended with sodium bicarbonate, calcium carbonate, Parteck® M200, Cab-O-Sil®, and magnesium stearate to obtain a uniform pull layer final blend.

B. Push Layer Blend:

POLYOX™ N 60, sodium chloride, red pigment, and magnesium stearate are blended into a uniform blend.

C. Bilayered Tablet Core:

The pull layer blend from Step A and push layer blend from Step B are pressed horizontally, using a suitable tablet press, into a bilayered tablet core.

D. Coating System:

Bilayered tablet cores from Step C are coated with a seal coat comprising OPADRY® II, Clear, a functional coat comprising EUDRAGIT® RL PO, triethyl citrate, and talc, a cosmetic coat comprising OPADRY® II, Pink, and a final coat comprising OPADRY EZ clear.

E. Laser Hole Drilling:

A laser hole in fluid communication with the pull layer is drilled into the coating system (before application of the cosmetic coat and the final coat described in Step D, above).

The present disclosure is not to be limited in scope by the specific embodiments described herein. Indeed, various modifications of the disclosure in addition to those described herein will become apparent to those skilled in the art from the foregoing description. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

Patents, patent applications, publications, product descriptions, and protocols are cited throughout this application, the disclosures of which are incorporated herein by reference in their entireties for all purposes.

The invention claimed is:

1. An osmotic, floating gastroretentive dosage form comprising:
   a) a multilayer core comprising:
      (i) a pull layer containing an active pharmaceutical agent, an acid, and a gas-generating agent, and
      (ii) a push layer; and
   b) a permeable elastic membrane surrounding the multilayer core, wherein the permeable elastic membrane contains at least one orifice,
   wherein the permeable elastic membrane comprises copolymer of ethyl acrylate, methyl methacrylate, and trimethylammonioethyl methacrylate chloride (1:2:0.2) in powder form and at least one plasticizer,
   wherein the plasticizer is present in amount of from about 10 wt % to about 20 wt % of the amount of copolymer,
   wherein the gas generating agent is present in an amount of from about 10 wt % to about 50 wt % of the pull layer
   wherein the orifice in the permeable elastic membrane is in fluid communication with the pull layer, and
   wherein the dosage form when coming in contact with a dissolution medium, floats in 30 minutes or less, exhibits about 50% volume gain in about 30 minutes and about 250% volume gain in about 4 hours, maintains the volume gain of about 250% from about 4 hours to about 14 hours, and collapses back to about 150% volume gain in about 18 hours.

2. The dosage form of claim 1, wherein the at least one plasticizer is selected from the group consisting of triethyl citrate, triacetin, polyethylene glycol, propylene glycol, dibutyl sebacate, and mixtures thereof.

3. The dosage form of claim 1, wherein the acid is selected from the group consisting of succinic acid, citric acid, acetic acid, malic acid, and tartaric acid, boric acid, and mixtures thereof.

4. The dosage form of claim 1, wherein the pull layer and the push layer each comprises at least one water-soluble hydrophilic polymer.

5. The dosage form of claim 4, wherein the water-soluble hydrophilic polymer in the push layer is a polyethylene oxide polymer having an average molecular weight greater than or equal to 600,000 Da.

6. The dosage form of claim 5, wherein the polyethylene oxide polymer has an average molecular weight of about 700,000 Da, about 800,000 Da, about 900,000 Da, about 1,000,000 Da, about 2,000,000 Da, about 3,000,000 da, about 4,000,000 Da, about 5,000,000 Da, about 6,000,000 Da, about 7,000,000 Da, or intermediate values therein.

7. The dosage form of claim 4, wherein the water-soluble hydrophilic polymer in the pull layer is a polyethylene oxide polymer having an average molecular weight less than or equal to 1,000,000 Da.

8. The dosage form of claim 7, wherein the polyethylene oxide polymer has an average molecular weight of about 100,000 Da, about 200,000 Da, about 300,000 Da, about 400,000 Da, about 500,000 Da, about 600,000 Da, about 700,000 Da, about 800,000 Da, about 900,000 Da, or intermediate values therein.

9. The dosage form of claim 4, wherein the at least one water-soluble hydrophilic polymer in the pull layer is a mixture of two polyethylene oxide polymers having average molecular weights of about 7,000,000 Da and about 200,000 Da, wherein the polyethylene oxide polymers are present in a ratio of from about 1:99 to about 10:90.

10. The dosage form of claim 1, wherein the gas-generating agent is $NaHCO_3$, $CaCO_3$, or a mixture thereof.

11. The dosage form of claim 1, wherein the dosage form provides extended release of the active pharmaceutical agent for a period of at least about 6 hours.

12. The dosage form of claim 1, wherein the active pharmaceutical agent is a moderately soluble drug.

13. A method for treating a condition that requires extended release of an active pharmaceutical agent in upper gastrointestinal tract, the method comprising administering to a subject, a self-regulating, osmotic, floating gastroretentive dosage form comprising:
   a) a multilayer core comprising a pull layer and a push layer, and
   b) a permeable elastic membrane surrounding the multilayer core,
   wherein the pull layer comprises a polyethylene oxide polymer having an average molecular weight less than or equal to 1,000,000 Da, an active pharmaceutical agent, an acid, and a gas-generating agent,
   wherein the push layer comprises a polyethylene oxide polymer having an average molecular weight greater than or equal to about 600,000 Da,
   wherein the membrane comprises a plasticizer and a copolymer of ethyl acrylate, methyl methacrylate, and trimethylammonioethyl methacrylate chloride (1:2:0.2) in powder form,
   wherein the plasticizer is present in an amount of from about 10 wt % to about 20 wt % of the copolymer,
   wherein the gas generating agent is present in an amount of from about 10 wt % to about 50 wt % of the pull layer,
   wherein the dosage form when coming in contact with a dissolution medium, floats in 30 minutes or less, exhibits about 50% volume gain in about 30 minutes and about 250% volume gain in about 4 hours, maintains the volume gain of about 250% from about 4 hours to about 14 hours, and collapses back to about 150% volume gain in about 18 hours, and
   wherein the dosage form provides a stable plasma concentration of the active pharmaceutical agent for at least about 6 hours.

* * * * *